United States Patent [19]
Mishra

[11] Patent Number: 5,955,594
[45] Date of Patent: Sep. 21, 1999

[54] NUCLEIC ACIDS ENCODING PROTEINS FOR EARLY LIVER DEVELOPMENT

[76] Inventor: Lopa Mishra, 6910 Oakridge Ave., Bethesda, Md. 20815

[21] Appl. No.: 08/841,349
[22] Filed: Apr. 30, 1997
[51] Int. Cl.$^6$ .................................................. C12N 15/12
[52] U.S. Cl. ...................... 536/23.5; 530/350; 530/399; 935/3; 935/9; 935/11
[58] Field of Search ................................ 536/23.1, 23.5; 435/172.1, 172.3, 69.1, 70.1, 71.1, 71.2, 325, 252.3, 320.1, 471; 935/3, 9, 11, 22, 66, 70, 72; 530/350, 399

[56] References Cited

PUBLICATIONS

Devarajan et al., "Identification of a Small Cytoplasmic Ankyrin . . . ", Journal of Cell Biology, vol. 133, No. 4, May 1996, pp. 819–830.
Chang et al., "Cloning of a Portion of the Chromosomal Gene and cDNA for Human . . . ", Genomics 17, 1993, pp. 287–293.
Zagon et al., "Localization of Spectrin in Mammalian Brain", The Journal of Neuroscience, vol. 4, No. 12, Dec. 1984, pp. 3089–3100.
Ryan et al., "Repression of Pax–2 by WT1 during normal kidney development", The Company of Biologists Limited, 1995, pp. 867–874.
Dubreuil et al., "A β–Spectrin Isoform from Drosophila ($β_H$) Is Similar in Size to . . . ", The Journal of Cell Biology, vol. 111, Nov. 1990, pp. 1849–1858.
Kotula et al., "The Exon–Intron Organization of the Human Erythrocyte α–Spectrin Gene", Genomics 9, 1991, pp. 131–140.
Wang et al., "The association of the C–terminal region of βIΣII spectrin to . . . ", Biochemical and Biophysical Research Comm., vol. 217, No. 2, Dec. 14, 1995, pp. 608–615.
Lombardo et al., "βII–Spectrin (Fodrin) and βIΣ2–Spectrin (Muscle) . . . ", The Journal of Biological Chemistry, vol. 269, No. 46, Nov. 18, 1984, pp. 29212–29219.
Davis et al., "Identification of Two Regions of $β_G$ Spectrin That Bind to Distinct . . . ", The Journal of Biological Chemistry, vol. 269, No. 6, Feb. 11, 1994, pp. 4409–4416.
Nelson et al., "Localization of phospholipase C–γ 1 to mouse Chromosome 2", Mammalian Genome 3, 1992, pp. 597–600.
Mayer et al., "A novel viral–oncogene with structural similarity to phospholispase C", Nature, vol. 332, Mar. 17, 1988, pp. 272–275.
Saraste et al., "Pleckstrin homology domains: a fact file", Current Opinion in Structrual Biology 1995, 5, pp. 403–408.
Rhee et al., "Studies of Inositol Phospholipid–Specific Phospholipase C", Science, vol. 244, May 5, 1989, pp. 546–550.
Prescott, "A Thematic Series on Phospholipases", The Journal of Biological Chemistry, vol. 272, No. 24, Jun. 13, 1997, pp. 15043–15047.
Bennett et al., "Molecular cloning and complete amino–acid sequence of form–I . . . ", Nature, vol. 334, Jul. 21, 1988, pp. 268–272.
Rhee et al., "Regulation of Inositol Phospholipid–specific Phospholipase C Isozymes", The Journal of Biological Chemistry, vol. 267, No. 18, Jun. 25, 1992, pp. 12393–12396.
Lee et al., "Promoter Region of the Rat Phospholipase C–γ1 Gene", Biochemical and Biophysical Research Comm., vol. 194, No. 1, Jul. 15, 1993, pp. 294–300.
Touhara et al., "Binding of G Protein βγ–Subunits to Pleckstrin Homology Domains", The American Society for Biochemistry and Molecular Biology, pp. 10217–10220.
Jean et al., "Comparative Assignments of the Genes of the Inter–α–inhibitor Family", Genomics 41, 1997, pp. 139–140.
Salier et al., "Review Article: The inter–α–inhibitor family: from structure to regulation", Biochem. J. (1996), 315, pp. 1–9.
Chan et al., "The three heavy–chain precursors for the inter–α–inhibitor family in mouse . . . ", Biochem. J. (1995) 306, pp. 505–512.
Castillo et al., "Subunit structure of bovine ESF . . . " Federation of European Biochemical Societies, vol. 318, No. 3, Mar. 1993, pp. 292–296.
Zhao et al., "Evidence for the Covalent Binding of SHAP, Heavy Chains of . . . ", The Journal of Biological Chemistry, vol. 270, No. 44, Nov. 3, 1995, pp. 26657–26663.
Chen et al., "Proteins of the Inter–α–trypsin Inhibitor Family Stabilize . . . ", The Journal of Biological Chemistry, vol. 269, No. 45, Nov. 11, 1994, pp. 28282–28287.
Saguchi et al., "Isolation and Characterization of the Human Inter–α–Trypsin Inhibitor . . . ", J. Biochem 119, 898–905 (1996).
Saguchi et al., "Cloning and Characterization of cDNA for Inter–α–Trypsin Inhibitor . . . ", J. Biochem 117, 1995, Nos. 14–18.
Salier et al., "Developmentally regulated transcription of the four liver–specific genes . . . ", Chem. J. (1993) 296, pp. 85–91.

(List continued on next page.)

*Primary Examiner*—Prema Mertz
*Attorney, Agent, or Firm*—Larson & Taylor

[57] ABSTRACT

Early developing stage-specific liver proteins and the genes coding for them that have been isolated and sequenced are provided, and these genes and proteins can be utilized to diagnose and/or treat a wide variety of liver disorders and other ailments. Included in the proteins identified and isolated in the present invention are the proteins known as elf 1–3, liyor-1 (145), pk, protein 106, and praja-1, along with the nucleic acid sequences coding for these and other proteins. Since the early developing liver proteins of the invention arise during embryogenesis when the liver and other organs are in transition from an undifferentiated state to a differentiated one, these proteins are involved in tissue differentiation and thus can be utilized in methods of diagnosing and treating a variety of liver diseases and other disorders including those relating to oncogenesis and tissue repair. Accordingly, the isolated early developing liver proteins in accordance with the present invention should have implications for diagnosis and treatment of a range of diseases from end stage cirrhosis to hepatocellular carcinoma and many other disease conditions.

2 Claims, 25 Drawing Sheets

OTHER PUBLICATIONS

Bhalerao et al., "Molecular Cloning, Characterization, and Genetic Mapping . . . ", The Journal of Biological Chemistry, vol. 270, No. 27, Jul. 7, 1995, pp. 16385–16394.

Salier et al., "Homologous Chromosomal Locations of the Four Genes for . . . ", Genomics 14, 1992, pp. 83–88.

Pu et al., "Purification and Characterization of PK–120, a Novel Substrate . . . ", Biol. Pharm. Bull. 18(6), 1995, pp. 837–841.

Perantoni et al., "Induction of tubules in rat metanephrogenic mesenchyme in the absence . . . ", Differentiation 1991, 48:25–31.

Palazzolo et al., "Use of a New Strategy to Isolate and Characterize . . . ", Neuron, vol. 3, Oct. 1989, pp. 527–539.

Nakayama et al., "A Novel RING–H2 Motif Protein Down-regulated by Axotomy . . . ", The Journal of Neuroscience, Jul. 1995, 15(7), pp. 5238–5248.

Kanno et al., "mel–18, a Polycomb group–related mammalian gene, . . . ", The Embo Journal, vol. 14, No. 22, 1995, pp. 5672–5678.

Bouchard et al., "The Drosophila melanogaster developmental gene g1 encodes . . . ", Gene, 125, 1993, pp. 205–209.

Borden et al., "The RING finger domain: a recent example of a sequence–structure family", Current Opinion in Structural Biology, 1996, 6:395–401.

FIG. 1A

```
   1 TCGGGAAANGATTGATTTGGCCNCCTCGGNAAGGCNTTTTATTTTGCNNCAAGGAGGGCCCGGGGGGTTTCCAACCNAAATAAAATT   87
  88 TTTTTTCGGATCCCGGGGGTTTCCTCAGGGAGTTGGGGAATTTTACTTTGAAAGCAGATNTTTCNGAGNTCCGGGTAGCTNTCCAAT  174
 175 AACTNTTTGTCATCATTGCCAGACGGCAGATCAAGGATGCCTTCGGTTTACCCGTGCTGTTCAGAGAACGGCTTTTGGAAGATTGAT  261
 262 TTTAAGTTATTTAACAGTCACAGACAGGTGTCATNTNTGGAGAATAGAGGCAAGTCCGCGGTGAGGGATGAAGCAGGAGAGATAGGG  348
 349 GAAGGCAGACAGGACTGCTGGGCCAAGGAAGCTGTGCTGATTTGAGCACAGTGGGAATTCACGTACGCAATTTCAAAGGCTTTAGTG  435
 436 GTAAATTCTGAAGCTCAGATGCAGGCAAGACCCAAGAGGATAGTGTACACAGAGAGAAGAGGGTCNTCAGGATCGTGCGTAGAGTGG  522
 523 AGAGAGCCCCAAAGGCAGGAGGGAAGAGCCTCAGTGGATTACTTAGGGATGAGGGAGAGAAGAAAAAAGGTTCTTGCAAGGTGTGGG  609
 610 GTCTTCCAAATTCAGGAGTTCACTGAACTATAGAGAAGGTGTAGCGGGTGAAAGGGGCCATGTGATGAGGATGGCAAGCAAGGCTGT  696
 697 GGCGCAGATGACGAGATGCCTGGGTCGGGAGGTCAGGGGAGACCCAGGATTGGGGTCACCTGTGTCTGCGCAGAGGGGAAGCCACCC  783
 784 TGCAACTGGCCCAGCACTGAGTCCAGAGGAAAATGAGGCAGAGGACAAACCAGAGCTTCGGAGACTAAGTGCAGGTAGGGCGCGGGC  870
 871 GGAGCGTGAGGAGGGCAGCGGACCACGCGAGAGGCNTCGAAGGCCACCGGACCCGCGTCCGAGAGTCTGAGGGCCCTGCCCACACCT  957
 958 GCGRGGCCCCCTCCCCAGAGGCCACACTCCAAGGCCACCCTAGAACCCGTCTGTCTGCTCAAGCCCTTGCAAAAGACGTCTGCGCAG 1044
1045 AGGGGGCGTGGCAGGCGTGCTGTCACTCACGGCCTGTTAGCCAATCCACGAGTGCGCCCCTCCCCGGAGAGGGTGCGCGGAGGGCCC 1131
1132 GCCCCCGCCGCCACCGCGGGTGTGAGGAGGCCAGGCTGGCGCGGCTCCCTCCGCCCGGCAGCCTTGCCAGGTAACCGGGTTCGGCGG 1218
1219 GAGGGCTGGGGGTCGCGCAGCCCCCTCGCTCCCTGGGAGGCGTGCACACTGCCGCGGCGGGTCCCGTGTGGGCCGGAGGCCCGTGCG 1305
1306 CGCGTCGGACCGACGGGCCGCAGCCTGTGGGCGGGGTTGCGTGCGTGACGGGCGGCCGTGCCCCGCGTTGTGTCAGGCCTGCGCGGG 1392
1393 GAAAGCTCGGCCGAACCGAGGTGTCCAGGTCCGCCCGCTGCGGCCTGCCCCGGGTTGCGGGGCGCAGGCGCGGCGGTGGGCGGGGGT 1479
1480 CGTCCCCAGGAGCGTCTTTGTTCCCGGCGCGCTGAGGGCGGAGCCTCACCCCGCCCCGCCCCCGCGCTCAGTCCCCGCCCCGCGTCC 1566
1567 GCCCGCAGGAGCTGCCACCGGGTCCCGCTGGCCTCCCCGGCCGCCGCCACCGCCTCCGCCTCCGCCGCTCCGGGCCCGCCGGCTTGC 1653
1654 GTCGCCGAGGTCGCTGCAGCATGGCGNGCGTCGCGACCCCCTGCGCCAACGGCTGCGGGCCTGGCGCACCCTCCGAAGCCGAGGTGC 1740
                        M  A  ?  V  A  T  P  C  A  N  G  C  G  P  G  A  P  S  E  A  E  V  L

1741 TGCACCTCTGCCGCAGCCTCGAGGTGGGCACCGTCATGACTTTGTTCTACTCCAAGAAGTCGCAGCGGCCAGAACGGAAGANCTTCC 1827
      H  L  C  R  S  L  E  V  G  T  V  M  T  L  F  Y  S  K  K  S  Q  R  P  E  R  K  ?  F  Q

1828 AGGTCAAGTTGGAGACGCGCCAGATCACATGGAGCCGCGGCGCGGACAAAATCGAGGGGTCCAGTAAGTGCGCCCCACTCCGGCCTG 1914
       V  K  L  E  T  R  Q  I  T  W  S  R  G  A  D  K  I  E  G  S  S  K  C  A  P  L  R  P  A

1915 CCTCGCGCCTGCCCGCCTCCCAAACACTTGGGCAAACTTTCGGGCCTCGCGCCTGGCGCCCCGTCTCCGCCCAGTCCCTGGTGGTCA 2001
       S  R  L  P  A  S  Q  T  L  G  Q  T  F  G  P  R  A  W  R  P  V  S  A  Q  S  L  V  V  T

2002 CTCTGGGGCGGGTGGAGGGGGGCATCCGGGTCTTGGATCACCTGATAGGACACCCCCTCCCCCAGTAGGGGGGGAGTGTTCCAGGCA 2088
       L  G  R  V  E  G  G  I  R  V  L  D  H  L  I  G  H  P  L  P  Q  *

2089 CTTTGCCCTGAGGCCTAAGAGTCCTCACTGGTTGGACAAGTGGAGTGGGATTCCGGCCCTTAGCATCGGGCGGCTGTCAGTGGCTGT 2175
2176 GAGGGGAAGCCAAGCAGGGACCCCCTCATCCAACCTGAGAACCTGGGGAACCGACAAGATCTTCCTGCCCACTGCCATTTCTCCAG 2262
2263 AGTGTGCTGTCTGTGAAAACTCCTAAGAGCTCCGGGATGGGCTTATTGGCGCAAGAACCTTTGGAATCCTCATGTAGAACTTAGGCA 2349
2350 GATGTTGGGGTAGGGCTGGTGGTGAAGCAGAGCCCTACTCATCTCCCCTCTTCTTTGGGAGGATGGGGTATGAAAGCTAAAACCGTG 2436
2437 ACTGCTTCCCCCTCCCATGTCCCGTGGATGGGTTTTTTTTTTTTTTTTTTTGCCCCAGATCTGAATTTTGGAGGTCCATGGTGCTA 2523
2524 GGCAGCCATCCAAAGCTAGAGCCATGGCTCCTTTGCCCTTGCAGCATATAACAAGGAGCTTGCATTCAGAAAGGTTCCCTGGCCTTG 2610
```

FIG. 1B

```
2611 GGTTTTGGGGTCCAGCCCTTTGTGTTGGATGTTCTCGTGACCACAGGGTAGCCCANAGTTGCTCCTCTGGTTTCCTGTCGTACCCTT 2697
2698 CCCAAACCTGAGTGTGGTGGGTTTACACACAAGTCTCTGGTGGGAGAAGTAAGTCAGGAGTTTTGAGAAACCTCGGCTCTTTGTGAT 2784
2785 AGTCATTTTCCTCGGTGTGAGGCAGGATGAGGAGTCTTTGCAACTCCAGGCTTTGAGATGTTTCTTACAAGAACCCCCAAAGAGTCT 2871
2872 ATGGTTGAAGGGACCTAGCCTAAGAGCCAGGTCTGTGTTAGAGAAGGGGGGGTGGTGTCAGGAAGTAACAACGGCGAGAAGGTCCCA 2958
2959 CAGATCTTCCTGGGGATGGTGTACATGTGTGTCGATGGGTGAGGAGATGAGGAGGAAGGAAGGTTTCTGTGGTAAGACAGCCATCCT 3045
3046 CAACTACAAACTTCAGGTCTGACAGAATTGGCCCTTAACCATCACCAGTGCCCATCAGCCCTGGCCTCCGCTGGAAGAACATTTCAG 3132
3133 TGATTTTCAGTGTTGGGGATGGAACTGCAGACAGTTCCGGTAGTCCTGAGACATCACTCAGACATCAGGTTGCAGGCATGGCATTT 3219
3220 TACGTTTGTAGTATTTCCTGTGTTTAAGTGGTGGCATTAGTTCCCCGGTAGCTAGCTCTTGGTAACAGCTGCACTGTAAACCGTGTG 3306
3307 TGTAGCCCAGTAGTGGAAGATAGCTATGGTATTTGAAGCCAGTGTGTTAGCTGTACGTCACCCAGCCAGGTGCTTTCCCTCTCGGAG 3393
3394 CCTCGGTTCCTCTGTAAGTTAGCAGAAGTATATTTACTATAAATGGTCACTTTTGGAAGTGAGATAGTTGGTGTAAAGTAAGCAAAC 3480
3481 TAAATATGTAATAGATGCGAGCAGAGACGTTACAGAAGTTTAAGAACCAGTTATTAGTAGCAGTAGCTATGGTAGATGCTTGTCCTC 3567
3568 CTAGACCCTGGGATGGGGCTTCTGAGGGAGGTCTAATGTGGCTGTTAGAAAAAGAAAGGGCTCTGAGGGAGGAGGGCCGAGAGAGGG 3654
3655 TCCCGTTCTCCTTAATTGCATTACCCAGGATAAAAGAGGGAAACTCTTGTTTTGCCGTACATCGTTTACCCTTCTGTTCACCTGTCAT 3741
3742 GTAAGATGAGTTTCTATGTTTGGAATTTTGTACATTGGATGCCATTGTGAGTTGGGGCCTGGACAGAAAGAAGGGACTTAGAGACAG 3828
3829 AACCATCCAGTCCGTTTTGTCTCACTTGGGTCTTTGAGGATGGGTGGCAGGAATACAGAGGACGTCACCTTTCCAGACCCAGAAAAG 3915
3916 TCACCCAGAGATATGCATGTTTTCATTGGGCCCGACCCTGTGATTTTTGGGGTCCAGAATGAAGGCTGCAGACTAGCCTGTGTGGAC 4002
4003 TTCATACCTTGTAAATGGAGCCCACCACCGAAGCCCTGCCCCACTTCTGCTGGAATGCACCTCACTGCCTTTGTGGGTTCCCAAACC 4089
4090 TGCAGCCTCCTGCAGATTGTGAAAAGGCTTGAGTTGCCAGCTCCCTCCCTACTGTCTGGTCTCTTGTTCAGATGCCTCAGGTATTTG 4176
4177 ACTTTTTGCTGATAACCTTATCCCTACCTGAAGCCAGGCCAGAGAGAAAGACTGCCGCTGTCTGCCCTCAGGGTGCTCACGGAACAC 4263
4264 AACGACAGGCTGACTGCCATTTCCTAAATCTTGAGTTCTCTCACTGTGACACCTGTGAAACTAGTTAGCACCTTCTGATGTCTAAGG 4350
4351 CAGCGGTCTACTTGAGAAGTGCTTTGGTGCTGTTTGGTTGTGTGACTGAAGTCAGGCTGGTGTCTGGCATTTATGTTGCAGAATTTA 4437
4438 GTGAGTTAAAAGCAGCCATAGACTTCCTGCCCAGTGCTAAACAGACTTTTCACTCTGCTGCAGGCTAGTCCTCAGAGGACTCTGCTC 4524
4525 CCAGGTTGTGTTGGTGGTAGGCCTTGGTCTCCTGTTTTCTGTAGCCTTTGTTGCCCCTTGTGAAGAGAAACCTCCATGTTTAGGTGG 4611
4612 TATTTACAGGCAGAGACCTCCATCTTCATCAAAGACGCCTTCCTAGGCTTTCCATATGTAATGCCTGTAGTGAGATGGCTCAGACCT 4698
4699 ATTCTTCGTGAGGTTGTCCAGTTAAGGACCACTGTTGGCATAGTAGCTCCAGTAGAGACTCTAAAGCTATGTTGTTATTGTGGTGAG 4785
4786 GATTGCAGTACCAAGGGGCTGGCTCTGAGAGTAGGTCCGTGGCACCTAAGAATTGTCTGCACATGTCCCTCAAGGATTCCTTTTNGC 4872
4873 TGGCCCACAGTGAGAGAGCAGCAGAAAGCATGCGCCTGGATCTAAGAAAGGTTAATGAAACCATGGTACCTATGGGAGCTTTACAAC 4959
4960 CTGGGCTTCTGTCTCCGGTAGCCATTTCTAAAAGANATTATGAAATTGTGGTAGATTGAAAGATGTTCCTTACTATTCCTTTACATC 5046
5047 CTGAGGATCACGAAAGATTTGCTTTCAGTATTCCTACTATTAATTTTAAAGAACCTATGAAAAGATATCAATGGACAGTTCTTCCAC 5133
5134 AAGGCATGGCTAATAATCCTACCTTATGTCAAANTTGTGGCACAACCATTCACCTGTGAGACACAATGACTATGACTACTCNTCNTG 5220
5221 ATGATGATGANGATGATGAGATGATGATGATGATGATGATGACACACAMGATAGAGATGATTCTAANGCGGAAANATCCCGACTGCT 5307
5308 TTNCTTAAAATTACCNNCCTNCGAAAAGATTAAACCCGAAAGGTCACCGATCTATATTTNGTTTAANTNATACCGTTTCCCAAAATT 5394
5395 TTNCGGACCTNAANTTTNATCAATTTTGTNTATGNTCCCC 5434
```

```
ACCTTGGCAATGACCTGGCAGGTGTCATGGCCCTGCAGTGCAAGCTGACTGGCATGGAACGAGACTTGGTAGCCATTGAGGCGAAGCTGAGTGACCTGCAGAAAGAAGCTGAGAAGCTGG 3360
 L  G  N  D  L  A  G  V  M  A  L  Q  C  X  L  T  G  M  E  R  D  L  V  A  I  E  A  K  L  S  D  L  Q  K  E  A  A  K  L  E  1010
AGTCCGAGCACCCTGACCAGGCTCAAGCTATCCTGTCTCGGCTGGCCGAGATCAGTGATGTGTGGGAGGAAATGAAGACAACCCTGAAGAACCGAGAGGCCTCCCTGGGAGAGGCCAGCA 3480
 S  E  H  P  D  Q  A  Q  A  I  L  S  R  L  A  E  I  S  D  V  W  E  E  M  K  T  T  L  K  N  R  E  A  S  L  G  E  A  S  K  1050
AGCTGCAGCAGTTTCTGCGGGACTTGGACGACTTCCAGTCTTGGCTCTCCAGGACCCAGACTGCTATCGCCTCAGAGGACATGCCCAATACCCTCACTGAGGCAGAGAAGCTTCTCACAC 3600
 L  Q  Q  F  L  R  D  L  D  D  F  Q  S  W  L  S  R  T  Q  T  A  I  A  S  E  D  M  P  N  T  L  T  E  A  E  K  L  L  T  Q  1090
AGCACGAGAATATCAAAAATGAGATCGACAATTATGAGGAAGACTACCAGAAGATGCGGGACATGGGCGAGATGGTCACCCAGGGGCAGACTGATGCCCAGTATATGTTTCTGCGGCAGC 3720
 H  E  N  I  K  N  E  I  D  N  Y  E  E  D  Y  Q  K  M  R  D  M  G  E  M  V  T  Q  G  Q  T  D  A  Q  Y  M  F  L  R  Q  R  1130
GGCTGCAGGCCTTAGACACTGGCTGGAATGAGCTCCACAAAATGTGGGAGAACAGGCAAAACCTCCTCTCCCAGTCCCATGCCTACCAGCAGTTCCTTAGGGACACCAAACAAGCTGAAG 3840
 L  Q  A  L  D  T  G  W  N  E  L  H  K  M  W  E  N  R  Q  N  L  L  S  Q  S  H  A  Y  Q  Q  F  L  R  D  T  K  Q  A  E  A  1170
CTTTTCTTAATAACCAGGAGTATGTTTTGGCTCATACTGAAATGCCCACCACCCTGGAAGGAGCTGAAGCAGCCATTAAAAAGCAGGAGGACTTCATGACCACCATGGATGCCAACGAGG 3960
 F  L  N  N  Q  E  Y  V  L  A  H  T  E  M  P  T  T  L  E  G  A  E  A  A  I  K  K  Q  E  D  F  M  T  T  M  D  A  N  E  E  1210
AGAAGATCAATGCTGTTGTGGAGACTGGCCGAAGACTGGTGAGCGATGGGAACATCAACTCCGACCGCATCCAGGAGAAGGTGGACTCTATTGACGACAGACACAGGAAGAATCGAGAAG 4080
 K  I  N  A  V  V  E  T  G  R  R  L  V  S  D  G  N  I  N  S  D  R  I  Q  E  K  V  D  S  I  D  D  R  H  R  K  N  R  E  A  1250
CAGCCAGTGAACTTCTGATGAGGTTAAAGGACAACCGTGATCTACAGAAGTTCCTGCAAGATTGTCAAGAGCTGTCCCTCTGGATCAATGAAAAGATGCTTACAGCTCAAGACATGTCTT 4200
 A  S  E  L  L  M  R  L  K  D  N  R  D  L  Q  K  F  L  Q  D  C  Q  E  L  S  L  W  I  N  E  K  M  L  T  A  Q  D  M  S  Y  1290
ATGATGAAGCCAGAAATCTGCACAGTAAATGGTTAAAGCATCAAGCATTTATGGCGGAACTTGCATCCAACAAAGAATGGCTTGACAAAATTGAGAAGGAAGGAATGCAGCTTATTTCAG 4320
 D  E  A  R  N  L  H  S  K  W  L  K  H  Q  A  F  M  A  E  L  A  S  N  K  E  W  L  D  K  I  E  K  E  G  M  Q  L  I  S  E  1330
AAAAGCCAGAAACAGAAGCTGTGGTAAAGGAAAAACTCACTGGTTTACATAAAATGTGGGAAGTCCTTGAATCCACAACCCAGACCAAGGCCCAGCGGCTCTTTGATGCAAATAAGGCTG 4440
 K  P  E  T  E  A  V  V  K  E  K  L  T  G  L  H  K  M  W  E  V  L  E  S  T  T  W  T  K  A  W  R  L  F  D  A  N  K  A  E  1370
AGCTTTTCACACAAAGCTGCGCAGATCTTGACAAATGGCTACATGGCCTGGAGAGCCAGATTCAATCTGACGACTATGGCAAAGACCTTATTAGTGTCAATATTCTTCTGAAAAAGCAAC 4560
 L  F  T  Q  S  C  A  D  L  D  K  W  L  H  G  L  E  S  O  T  W  S  D  D  Y  G  K  D  L  T  S  O  N  T  L  L  K  K  Q  Q  1410
AGATGCTGGAGAATCAGATGGAAGTTCGGAAGAAAGAGATCGAGGAACTGCAGAGCCAAGCCCAGGCGCTGAGTCAGGAGGGGAAGAGCACAGATGAGGTGGACAGCAAACGCCTTACTG 4680
 M  L  E  N  Q  M  E  O  R  K  K  E  I  E  E  L  Q  S  Q  A  Q  A  L  S  Q  E  G  K  S  T  D  E  V  D  S  K  R  L  T  V  1450
TGCAGACCAAGTTCATGGAGCTTCTGGAGCCCTTGAGTGAGAGGAAGCATAACCTGTTAGCTTCCAAGGAGATCCATCAGTTCAACAGGGATGTGGAGGACGAAATCCTATGGGTTGGCG 4800
 Q  T  K  F  M  E  L  L  E  P  L  S  E  R  K  H  N  L  L  A  S  K  E  I  H  Q  F  N  R  D  V  E  D  E  I  L  W  V  G  F  1490
```

```
   1 CCTGCGTCCT TCCTCCTTTT CCTCCTTCCC TCCTCCCTCC CGGGTAATTT
  51 ATTTCTAGCT TCCAGGCAAG GGCCACACAA GGAAGGAAAT CCACAGGGGA
 101 TTAGATGCCG GGGTGGTAAC TCCACCAGGA TAGGTTGGAC TCTGCAGCCA
 151 ACTTCCTATC AGATCACCCT GCACCTATTT CCGACCCGAC CGGAATGCGA
 201 CTGGCTTGAG GTCCAGCCCT TTCGCCTGGG CGGGAGCAGA GCCGCGGAAG
 251 CTFCTTGGAG TTGGATGGGG GTAGGAAGGG GCTGGAGCGG GAATCCTACG
 301 ATGCAACTGG CCTGGGCCTA AGGTTGGGCA TAATGGAGTT GCAGAGGACA
 351 TCCAGCGTTT CAGGGCCGCT GTCGCCGGCC TACACCGGGC AGGTGCCTTA
 401 CAACTACAAC CAACTGGAGG GAAGATTCAA ACAGCTCCAA GATGAGCGTG
 451 AAGCTGTACA GAAGAAGACC TTCACCAAGT GGGTCAATTC CACCTTGCA
 501 AGAGTGTCCT GCCGAATCAC AGACCTGTAC ACGGACCTTC GAGATGGACG
 551 GATGCTCATC AAGCTACTGG AGGTCCTCTC TGGAGAGAGG CTGCCTAAAC
 601 CCACTAAGGG ACGGATGCGG ATCCACTGTC TGGAGAATGT CGACAAGGCT
 651 CTTCAATTCC TGAAAGAGCA GAGAGTCCAT CTTGAGAACA TGGGCTCCCA
 701 TGACATTGTG GATGGAAACC ACCGGCTGAC CCTCGGCCTC ATCTGGACAA
 751 TTATTCTGCG CTTCCAGATC CAGGATATTA GTGTGGAGAC TGAAGATAAC
 801 AAAGAGAAAA AGTCTGCTAA GGATGCATTG CTGCTGTGGT GCCAGATGAA
 851 GACAGCTGGG TACCCCAATG TCAACATTCA CAATTTCACC ACTAGCTGGA
 901 GGGATGGCAT GGCCTTCAAT GCACTGATAC ATAAACATCG GCCTGACCTG
 951 ATAGATTTTG ATAAACTGAA GAAATCTAAT GCACACTACA ATCTGCAGAA
1001 TGCATTTAAC CTGGCAGAGC AGCACCTTGG CCTCACTAAA CTGTTAGACC
1051 CTGAAGATAT CAGTGTGGAC CACCCTGATG AGAAGTCTAT CATCACATAC
1101 GTGGTGACTT ACTACCACTA CTTCTCCAAG ATGAAGGCCT TGGCTGTCGA
1151 AGGAAAGCGC ATTGGAAAGG TGCTTGATAA TGCTATAGAA ACAGAGAAAA
1201 TGATTGAGAA GTACGAGACA CTTGCTTCTG ACCTTCTGGA GTGGATTGAA
1251 CAAACCATCA TCATCCTAAA CAACCGCAAA TTTGCTAATT CACTGGTTGG
1301 GGTCCAACAG CAGCTCCAAG CATTCAACAC GTACCGCACA GTGGAGAAAC
1351 CACCTAAGTT TACTGAGAAG GGGAATTTGG AGGTGCTCCT TTTCGCGATT
1401 CAGAGCAAGA TGCGAGCGAA TAATCAGAAG GTCTACATGC CCCGCGAGGG
1451 GAAGCTCATC TCTGACATCA ACAAGGCCTG GGAAAGACTG GAAAAGCAG
1501 AACATGAGAG AGAACTGGCT CTGCGGAATG AGCTCATACG GCAGGAAAAA
1551 CTGGAACAAG TCGCCCGAAG ATTTGATCGC AAGGCAGCTA TGAGGGAGAC
1601 ATGGCTGAGT GAAAACCAGC GTCTTGTGTC TCAGGACAAC TTTGGATTTG
1651 ACCTTCCCGC TGTTGAGGCT GCTACCAAAA AACACGAGGC CATTGAGACA
1701 GACATCGCTG CATATGAAGA ACGAGTTCAG GCCGTGGTGG CTGTGGCCAG
1751 GGAACTTGAA GCCGAGAACT ACCATGACAT CAAGCGCATC ACAGCGAGGA
1801 AGGACAATGT CATCCGGCTC TGGAATACT TGCTGGAACT GCTCAGGGCC
1851 AGGAGGCAGC GTCTTGAGAT GAACCTGGGA TTGCAAAAGA TATTCCAGGA
1901 AATGCTTTAT ATTATGGACT GGATGGATGA AATGAAGGTG CTATTGCTGT
1951 CTCAAGACTA TGGCAAACAC TTACTTGGTG TTGAAGACCT GTTACAGAAG
```

FIG. 2G

```
2001 CATGCCCTGG TTGAAGCAGA CATTGCAATC CAAGCAGAGC GTGTAAGAGG
2051 TGTGAATGCC TCTGCCCAGA AGTTTGCAAC AGATGGGGAA GGCTACAAGC
2101 CATGTGACCC CCAGGTAATT CGAGACCGTG TTGCCCACAT GGAGTTCTGC
2151 TATCAAGAGC TTTGTCAGCT GGCTGCCGAG CGTAGGGCTC GCCTGGAAGA
2201 GTCCCGTCGC CTCTGGAAGT TCTTCTGGGA GATGCCAGAA GAGGAAGGCT
2251 GGATACCAGA GAAGGAAAAG ATCCTGTCCT CTGATGATTA CGGGAAAGAC
2301 TTGACCAGTG TCATGCGCCT GCTGAGCAAG CACCGGGCAT TTGAGGATGA
2351 GATGAGTGGC CGTAGTGGCC ATTTTGAGCA GGCCATTAAA GAAGGTGAAG
2401 ACATGATTGC AGAGGAACAC TTTGGATCGG AAAAGATCCG TGAGAGAATC
2451 ATTTATATCC GGGAGCAGTG GGCCAACCTG AACAGCTCT CAGCCATTAG
2501 GAAGAAGCGC CTAGAGGAAG CCTCATTACT GCACCAGTTC CAGGCTGATG
2551 CTGATGATAT TGATGCTTGG ATGTTAGATA TACTCAAGAT TGTCTCCAGC
2601 AATGATGTGG GCCATGATGA GTACTCCACG CAGTCTCTGG TCAAGAAGCA
2651 TAAAGATGTA GCAGAAGAGA TCACCAACTG CAGGCCCACT ATTGACACAC
2701 TGCATGAGCA AGCCAGTGCC CTTCCACAAG CACATGCAGA GTCTCCAGAT
2751 GTGAAGGGCC GGCTGGCAGG AATTGAGGAG CGCTGCAAGG AGATGGCAGA
2801 GTTAACACGG CTAAGGAAGC AGGCTCTGCA GGACACCCTG GCCCTGTACA
2851 AGATGTTCAG TGAGGCTGAT GCCTGTGAGC TCTGGATTGA CGAGAAGGAG
2901 CAGTGGCTCA ACAACATGCA GATCCCAGAG AAGCTGGAGG ACCTGGAAGT
2951 CATCCAGCAC AGATTTGAGA GCCTAGAACC AGAAATGAAC AACCAGGCTT
3001 CCCGGGTTGC TGTGGTGAAC CAGATTGCAC GGCAGCTGAT GCACAATGGC
3051 CACCCCAGTG AAAAGGAAAT CAGAGCTCAG CAAGACAAAC TCAACACGAG
3101 GTGGAGTCAG TTCAGAGAAC TGGTGGACAG GAAAAAGGAT GCTCTTCTGT
3151 CTGCCCTGAG CATCCAGAAC TACCACCTCG AGTGCAATGA AACCAAATCC
3201 TGCATCCGGG AGAAGACCAA GGTCATCGAG TCTACCCAAG ACCTTGGCAA
3251 TGACCTGGCA GGTGTCATGG CCCTGCAGTG CAAGCTGACT GGCATGGAAC
3301 GAGACTTGGT AGCCATTGAG GCGAAGCTGA GTGACCTGCA GAAAGAAGCT
3351 GAGAAGCTGG AGTCCGAGCA CCCTGACCAG GCTCAAGCTA TCCTGTCTCG
3401 GCTGGCCGAG ATCAGTGATG TGTGGGAGGA AATGAAGACA ACCCTGAAGA
3451 ACCGAGAGGC CTTCCTGGGA GAGGCCAGCA AGCTGCAGCA GTTTCTGCGG
3501 GACTTGGACG ACTTCCAGTC TTGGCTCTCC AGGACCCAGA CTGCTATCGC
3551 CTCAGAGGAC ATGCCCAATA CCCTCACTGA GGCAGAGAAG CTTCTCACAC
3601 AGCACGAGAA TATCAAAAAT GAGATCGACA ATTATGAGGA AGACTACCAG
3651 AAGATGCGGG ACATGGGCGA GATGGTCACC CAGGGGCAGA CTGATGCCCA
3701 GTATATGTTT CTGCGGCAGC GGCTGCAGGC CTTAGACACT GGCTGGAATG
3751 AGCTCCACAA AATGTGGGAG AACAGGCAAA ACCTCCTCTC CCAGTCCCAT
3801 GCCTACCAGC AGTTCCTTAG GGACACCAAA CAAGCTGAAG CTTTTCTTAA
3851 TAACCAGGAG TATGTTTTGG CTCATACTGA AATGCCCACC ACCCTGGAAG
3901 GAGCTGAAGC AGCCATTAAA AAGCAGGAGG ACTTCATGAC CCACATGGAT
3951 GCCAACGAGG AGAAGATCAA TGCTGTTGTG GAGACTGGCC GAAGACTGGT
```

FIG. 2H

```
4001 GAGCGATGGG AACATCACCT CCGACCGCAT CCAGGAGAAG GTGGACTCTA
4051 TTGACGACAG ACACAGGAAG AATCGAGAAG CAGCCAGTGA ACTTCTGATG
4101 AGGTTAAAGG ACAACCGTGA TCTACAGAAG TTCCTGCAAG ATTGTCAAGA
4151 GCTGTCCCTC TGGATCAATG AAAAGATGCT TACAGCTCAA GACATGTCCT
4201 ATGATGAAGC CAGAAATCTG CACAGTAAAT GGTTAAAGCA TCAAGCATTT
4251 ATGGCGGAAC TTGCATCCAA CAAAGAATGG CTTGACAAAA TTGAGAAGGA
4301 AGGAATGCAG CTTATTTCAG AAAAGCCAGA AACAGAAGCT GTGGTAAAGG
4351 AAAAACTCAC TGGTTTACAT AAAATGTGGG AAGTCCTTGA ATCCACAACC
4401 CAGACCAAGG CCCAGCGGCT CTTTGATGCA ATAAGGCTG AGCTTTTCAC
4451 ACAAAGCTGC GCAGATCTTG ACAAATGGCT ACATGGCCTG GAGAGCCAGA
4501 TTCAATCTGA CGACTATGGC AAAGACCTTA CCAGTGTCAA TATTCTTCTG
4551 AAAAAGCAAC AGATGCTGGA GAATCAGATG GAAGTTCGGA AGAAAGAGAT
4601 CGAGGAACTG CAGAGCCAAG CCCAGGCGCT GAGTCAGGAG GGGAAGAGCA
4651 CAGATGAGGT GGACAGCAAA GCGGTTACTG TGCAGACCAA GTTCATGGAG
4701 CTTCTGGAGC CCTTGAGTGA GAGGAAGCAT AACCTGTTAG CTTCCAAGGA
4751 GATCCATCAG TTCAACAGGG ATGTGGAGGA CGAAATCCTA TGGGTTGGCG
4801 AGAGGATGCC TTTGGCAACT TCCACAGATC ATGGCCATAA CCTTCAAACT
4851 GTGCAGCTGT TAATAAAGAA AAACCAGACC CTCCAGAAAG AAATCCAGGG
4901 ACACCAGCCT CGTATTGATG ACATCTTTGA GAGGAGTCAA AACATCATCA
4951 CAGATAGCAG CAGCCTCAAT GCCGAGGCTA TCAGGCAGAG GCTCGCTGAC
5001 CTGAAGCAGC TGTGGGGGCT CCTCATTGAG GAAACTGAGA AACGCCATAG
5051 ACGGCTGGAG GAGGCACACA AGGCGCAGCA GTACTACTTT GATGCAGCTG
5101 AAGCCGAGGC ATGGATGAGT GAACAGGAGT TGTACATGAT GTCTGAGGAA
5151 AAGGCCAAGG ATGAGCAGAG TGCTGTCTCT ATGTTGAAAA AGCACCAGAT
5201 TTTAGAGCAA GCTGTTGAGG ACTATGCAGA GACAGTACAC CAGCTCTCCA
5251 AGACTAGCCG GGCGCTGGTG GCTGACAGCC ATCCCGAAAG TGAGCGTATT
5301 AGCATGCGGC AGTCAAAGGT CGACAAGCTG TATGCTGGCC TGAAGGACCT
5351 TGCTGAGGAG AGGAGAGGAA AACTTGATGA GAGGCACAGG CTGTTCCAGC
5401 TCAACAGAGA GGTGGATGAC CTGAACAGT GGATCGCTGA GAGGGAAGTG
5451 GTCGCAGGCT CCCATGAGTT GGACAGGAC TATGAGCATG TCACGATGTT
5501 ACAAGAACGG TTCCGAGAAT TTGCTCGAGA CACAGGAAAC ATTGGGCAGG
5551 ACGCTGTGGA TACAGTTAAT AACATGGCAG ATGAACTCAG CAACTCTGGA
5601 CATTCAGATG CTGCCACCAT TGCTGAGTGG AAAGATGGTC TCAATGAAGC
5651 CTGGGCTGAC CTCCTGGAGC TCATTGACAC AAGAACACAG ATTCTTGCTG
5701 CCTCATATGA ACTTCATAAG TTTTACCATG ATGCCAAGGA GATCTTTGGC
5751 CGAATCCAGG ACAAACACAA GAAACTCCCT GAGGAGCTTG AAGAGATCA
5801 AAACACTGTG GAAACTTTAC AGAGAATGCA CACCACCTTT GAGCACGACA
5851 TCCAAGCTCT GGGCACTCAG GTGAGGCAGC TGCAGGAGGA TGCAGCTCGC
5901 CTCCAGGCAG CCTATGCAGG GGACAAGGCT GATGACATCC AGAAGCGTGA
5951 GAATGAGGTC CTGGAAGCCT GGAAGTCCCT GCTGGATGCT TGTGAGGGTC
```

FIG. 21

```
6001 GCAGGGTGCG GCTGGTAGAC ACAGGAGACA AGTTCCGSTT CTTCAGCATG
6051 GTGCGTGACC TCATGCTCTG GATGGAAGAT GTCATCCGGC AGATCGAGGC
6101 CCAGGAGAAA CCACGGGATG TGTCATCTGT TGAACTGTTA ATGAATAATC
6151 ATCAAGGTAT CAAAGCTGAA ATTGATGCTC GTAATGACAG CTTTACAGCC
6201 TGCATTGAGC TTGGGAAATC CCTGCTGGCA CGGAAACACT ATGCTTCTGA
6251 GGAGATCAAG GAAAAGTTAC TGCAGCTGAC AGAGAAAAGA AAAGAAATGA
6301 TTGACAAGTG GAAGACCGG TGGGAGTGGT TAAGACTGAT TTTGGAGGTC
6351 CATCAGTTCT GAAGGGATGC CAGTGTGGCA GAGGCTTGGC TGCTTGGACA
6401 GGAACCATAC CTATCCAGCC GTGAAATTGG CCAGAGTGTA GACGAAGTGG
6451 AGAAGCTTAT TAAGCGCCAT GAGGCGTTTG AAAAGTCTGC AGCGACCTGG
6501 GATGAGAGAT TCTCTGCTCT GGAAAGGCTG ACAACGTTGG AGCTACTGGA
6551 AGTGCGCAGA CAGCAAGAGG AAGAAGAAAG AAAGAGGCGG CCACCTTCTC
6601 CGGACCCAAA CACGAAGGTT TCAGAGGAGG CTGAGTCCCA GCAATGGGAT
6651 ACTTCAAAAG GAGACCAAGT TTCCCAGAAT GGTTTGCCGG CTGAGCAGGG
6701 ATCTCCACGG GTTAGTTACC GCTCTCAAAC GTACCAAAAC TACAAAAACT
6751 TTAATAGCAG ACGGACAGCC AGTGACCATT CATGGTCTGG AATGTGAAGT
6801 TCACTACCAT TTGTCAAGAA CCACTCTGTC CACATCCTTT GACCTTTTGG
6851 CTTCCACGTC ACCCAGAGTG TTAAAATTTT TACTTAATTC ATAGCTGTCC
6901 TTGATTTCAT ATTTGTTTGC ATTTAATTTA TGTTTCTTTG GATCCTCATT
6951 GCCTGAAAGC AGCATACTTA ATTTTTGTTT ATTTATTGTG A
```

```
   1 TTGGAACAGTTACTTCAGTGGAGGCAGCAGAAATGAGGCTAGTCCAGACTCACAGGAATAGGGTTCCATTCTCAAGAAGATGATTTA

88 AAGTAATTATCCTTTACGCATAGTTATCATCACCACAAAAAAAGATTCCAACCTTTTCCACAGAACTATTATGATTTATTTTTATAT

175 GAATGTATGTATTTATTATTATATGAACTCCTATAATGATCACCTTTACATATTCACATTTTCTTAATAATTAGTTTAGCCGCGTCC
         ──→ W57358, W47742

262 GGAGGTCCGACAGCTCTGCAGCTCCGAGCGCGCGACTAGCCAGAAAGTTTCAGGCCATCCATGAGCCACCAGGAAAGGATTGCCAGC
                                                                   M  S  H  Q  E  R  I  A  S

349 CAGAGGAGGACAACAGCCGAAGTCCCAATGCACAGATCAACTGCCAATCAAAGCAAGAGGAGCCGGTCACCATTTGCCAGCACACGT
      Q  R  R  T  T  A  E  V  P  M  H  R  S  T  A  N  Q  S  K  R  S  R  S  P  F  A  S  T  R

436 CGTCGCTGGGATGACAGCGAGAGCTCGGGAGCCAGCCTGGCTGTTGAGAGTGAGGATTATTCCAGGTGGCGGGATGCTGCCGATGCT
      R  R  W  D  D  S  E  S  S  G  A  S  L  A  V  E  S  E  D  Y  S  R  W  R  D  A  A  D  A

523 GAGGAGGCTCATGCCGAGGGCCTAGCCAGAAGAGGCCGAGGTGAGGCTGCCAGCAGCTCAGAGCCAAGGTATGCTGAAGACCAGGAT
      E  E  A  H  A  E  G  L  A  R  R  G  R  G  E  A  A  S  S  S  E  P  R  Y  A  E  D  Q  D

610 GCCAGGAGTGAACAAGCGAAGGCAGACAAAGTGCCAAGACGGCGGCGAACCATGGCAGACCCTGACTTCTGGGCATACACCGACGAT
      A  R  S  E  Q  A  K  A  D  K  V  P  R  R  R  R  T  M  A  D  P  D  F  W  A  Y  T  D  D

697 TACTACCGATACTACGAGGAAGATTCTGACAGCGACAAAGAGTGGATGGCTGCCCTGCGCAGGAAGTACCGAAGCCGAGAGCAACCC
      Y  Y  R  Y  Y  E  E  D  S  D  S  D  K  E  W  M  A  A  L  R  R  K  Y  R  S  R  E  Q  P

784 CAGTCCTCCAGCGGAGAAAGCTGGGAGCTTCTGCCAGGAAAGGAAGAACTGGAACGTCAGCAAGCCGGAGCTGGGAGCCTCGCCAGT
      Q  S  S  S  G  E  S  W  E  L  L  P  G  K  E  E  L  E  R  Q  Q  A  G  A  G  S  L  A  S

871 GCTGGCAGCAATGGCAGTGGTTATCCTGAAGAAGTACAAGACCCATCTCTTCAGGAGGAAGAACAGGCCTCTCTGGAAGAAGGAGAA
      A  G  S  N  G  S  G  Y  P  E  E  V  Q  D  P  S  L  Q  E  E  E  Q  A  S  L  E  E  G  E

958 ATCCCTTGGCTTCGCTACAATGAGAATGAAAGCAGCAGCGAGGGTGATAATGAGTCTACCCATGAGCTCATACAGCCTGGGATGTTC
      I  P  W  L  R  Y  N  E  N  E  S  S  S  E  G  D  N  E  S  T  H  E  L  I  Q  P  G  M  F

1045 ATGCTGGATGGAAACAACAACCTGGAAGATGACTCCAGCGTGAGCGAAGACCTCGAAGTGGACTGGAGCCTGTTTGATGGGTTTGCC
      M  L  D  G  N  N  N  L  E  D  D  S  S  V  S  E  D  L  E  V  D  W  S  L  F  D  G  F  A

1132 GATGGCTTGGGAGTGGCCGAAGCCATCTCCTACGTGGATCCTCAGTTCCTCACCTACATGGCTCTGGAAGAGCGTCTGGCCCAGGCA
      D  G  L  G  V  A  E  A  I  S  Y  V  D  P  Q  F  L  T  Y  M  A  L  E  E  R  L  A  Q  A
                                    ──→ clone CH7
```

FIG. 3B

```
1219 ATGGAGACGGCCCTGGCACACTTGGAGTCTCTGGCCGTTGATGTCGAAGTGGCCAACCCACCAAGCAAGGAGAGCATTGATGCC
      M  E  T  A  L  A  H  L  E  S  L  A  V  D  V  E  V  A  N  P  P  A  S  K  E  S  I  D  A

1306 CTTCCTGAGATCCTGGTCACCGAAGATCATGGTGCAGTGGGCCAGGAAATGTGTGTCCTATCTGTCAGGCGAATATGTGAAGGGG
      L  P  E  I  L  V  T  E  D  H  G  A  V  G  Q  E  M  C  P  I  C  C  S  E  Y  V  K  G

1393 GAGGTGGCAACTGAGCTACCCGGCCACCACTATTTCCACAAGCCGTGCGTGTCCATGTGGCTTCAGAAGTCTGGCACCTGCCCAGTG
      E  V  A  T  E  L  P  G  H  H  Y  F  H  K  P  C  V  S  I  W  L  Q  K  S  G  T  C  P  V

1480 TGCCGGCTGCCATGTTCCCTCCCCCCCTCTAAAAGCCAAGGCTCGTCGTAACAGTCCAGCCTGGTTACATTCCTGTCCGAAACCACAA
      C  R  M  F  P  P  P  L  *

1567 TACTACAGGAGCCCTTGTTGTTACAATGAACAATGAAACCAGTCAGTCAATTAGACTAAAGTTGTTGATTCCTTGTGATTATTGGATC

1654 TGAAAATGGTTGTGTACAATGACATTTAAAAAAAAAATCATCTCGTTTAGAAGGTAGAAGGGGGAAAGGAAACTTTCTAAATGCT

1741 GCTTGAGATTGCAGTAAGACACATACATTTCTAACCTGAAAGTTGAAACAAATCCCACTTGTTCTTGTAGACTGTGTCTCTTCTTACCT

1828 GTTGCCTGTCAGGGTTACCTATCTGCTAAACATGTCGGAAAGACACAAATTACTTTTGTTGCATGTCATGGGTTAATGTTCCTGTATT
                                                                            → primer DI
1915 TGCAGTGGTGTAAAAGCTTATTAAAGTTTTCTTTTGCTTTGACCCCGAA
```

FIG. 4A

```
   1 GGGCAACTGA AGGCAGATGA AGAGCCCTGC CCCTGCCCAC ATGTGGAACC
  51 TTGTGCTGTT CTTGCCTTCA CTGTTGGCTG TGCTTCCGAC CACTACTGCC
 101 GAGAAGAATG GCATCGATAT CTACAGCCTC ACGGTGGACT CCCGGGTCTC
 151 TTCCCGATTT GCCCATACTG TTGTCACCAG CCGGGTGGTC AACAGAGCCG
 201 ATGCTGTTCA AGAAGCGACC TTCCAAGTAG AGCTACCCAG GAAAGCCTTC
 251 ATCACCAACT CTCCATGAT CATCGATGGC GTGACCTACC CAGGGGTTGT
 301 CAAAGAGAAG GCCGAAGCCC AGAAACAATA CAGTGCCGCC GTGGGCAGGG
 351 GAGAGNGTGC TGGCATCGTC AAGACCACTG GGAGGCAGAC AGAGAAGTTT
 401 GAAGTGTCAG TCAACGTGGC CCCTGGTTCC AAGATTACCT TCGAACTCAT
 451 ATACCAGGAA CTGCTCCAAA GGCGACTGGG AATGTATGAG CTACTCCTCA
 501 AAGTGAGGCC TCAGCAGCTG GTGAAGCACC TTCAGATGGA CATCTACATC
 551 TTTGAGCCTC AGGGTATTAG CATCCTGGAG ACAGAGAGCA CCCTCATGAC
 601 CCCGGAGCTG GCAAATGCCC TTACCNCTTC ACAGAACAAG ACCAAGGCTC
 651 ATATCCGGTT CAAGCCGACG CTCTCCCAGC AACAGAAGTC TCAGAGTGAG
 701 CAGGACACGG TGCTGAATGG GGACTTCATC GTCCGCTATG ATGTCAACCG
 751 GTCTGACTCT GGGGGCTCCA TTCAGATTGA GGAAGGCTAC TTTGTGCACC
 801 ACTTTGCTCC AGAGAACCTT CCTACAATGT CCAAGAATGT GATCTTTGTC
 851 ATTGATAAAA GCGGATCTAT GTCAGGCAAG AAAATCCAGC AGACCCGAGA
 901 AGCCCTAGTC AAGATCTTGA AAGACCTCAG CCCCCAAGAC CAGTTCAACC
 951 TCATTGAGTT CAGTGGGGAA GCAAACCAAT GGAAGCAGTC ACTGGTGCAA
1001 GCGACAGAAG AGAATTTGAA CAAGGCTGTA ACTATGCTT CCAGGATCCG
1051 GGCTCACGGA GGGACCAACA TCAATANTGC AGTGCTGTTG GCTGTGGAGC
1101 TGCTGGACAG AAGCAACCAA GCTGAGCTAC TGCCCTCGAA GAGCGTCTCC
1151 CTTATCATCC TGCTCACGGA CGGTGACCCC ACTGTGGGAG AAACCAACCC
1201 CACGATTATC CAGAACAACG TGCGGGAAGC CATCAATGGG CAGTATAGCC
1251 TCTTCTGCCT GGGGTTCGGC TTTGATGTGA ACTATCCTTT CCTGGAGAAG
1301 ATGGCACTGG ACAATGGTGG CCTGGCCAGG CGCATCTATG AGGATTCAGA
1351 CTCTGCACTG CAGCTTCAGG ATTTCTACCA CGAAGTAGCC AATCCACTGC
1401 TCTCATCAGT GGCCTTCGAA TACCCCAGTG ATGCTGTGGA GGAAGTCACT
1451 CGGTACAAGT CCAACACCA CTTTAAGGGC TCAGAGATGG TGGTGGCTGG
1501 GAAGCTCCAg GACCAGGGTC CTGATGTCCT CTTAGCCAAA GTCAGTGGGC
1551 AGATGCACAT GCAGAACATC ACTTTCCAAA CGGAGGCCAG cGTAGCCCAA
1601 CAAGAGAAGG AGTTTAAGAG CCCCAAGTAc ATCTTTCACA AcTTTATGGA
1651 GAGACTGTGG GCAcTGCTGA cTATACAGCA ACAGCTGGAG CAGAGGATTT
1701 CAGCGTCAGG TGCCGAATTA GAGGCCCTCG NGGCCCAAGT TCTGAAcTTG
1751 TCACTCAAGT ACAATTTTGT CACCCCTCTC ACGCACATGG TGGTCACCAA
1801 ACCTGAAgGT CAAGAaCAAT TCCAAGTNGC TGAGAAGCCT GTGGAAGTCG
1851 GTGATGGCAT GNAGAGACTC CCCTTAGCAG CTCAAGCCCA CCCCTTCAGG
1901 CCTCCTGTCA GAGGATCTAA ACTGATGACC GTGCTGAAAG GAAGCAGGTC
1951 CCAGATACCC AGACGCGGTG ATGCCGTTAG GGCATCTAGG CAATACATTN
```

FIG. 4B

```
2001 CTCCCGGATT CCCCGGACCT CCTGGACCTC CCGGATTTCC TGCACCCCCT
2051 GGACCTCCTG GATTNCCTGC ACCCCCTGA CCTCCTCTTG CTTCTGGCTC
2101 TGACTTCAGC CTTCAGCCTT CCTATGAAAG GATGCTAAGC CTGCCCTCCG
2151 TTGCAGCACA ATATCCTGCT GACCCACATC TGGTTGTGAC GGAAAAAAGT
2201 AAGAAAAGCA CCATACCAGA GGAATCCCCN AACCCAGACC ACCCCCAGT
2251 TCCTACTATT ACCTTGCCGC TTCCGGGATC CAGTGTGGAC CAGCTCTGTG
2301 TGGATATCTT ACATTCTGAG AAGCCCATGA AGCTGTTCGT AGACCCCAGT
2351 CAGGGTCTGG AGGTGACTGG TAAGTATGAG AATACTGGGT TCTCGTGGCT
2401 CGAAGTGACC ATCCAGAAGC CTCACCTGCA GGTCCATGCA ACCCCTGAAC
2451 GACTGGTGGT GACACGAGGC AGAAAANACA CTGAATACAA GTGGAAGAAG
2501 ACGCTGTTCT CTGTGTTACC TGGCTTGAAG ATGACCATGA ATATGATGGG
2551 ACTCCTACAG CTCAGTGGCC CAGACAAAGT CACCATCGGC CTCCTGTCCC
2601 TGGATGACCC TCAGAGAGGA CTAATGCTGC TTTTGAATGA CACCCAGCAC
2651 TTCTCCAACA ACTGGAAAGG GGAGCTTGGT CAGTTTTACC GGGACATCGT
2701 CTGGGAGCCA CCCGTCGAGC CAGATAATAC AAAACGGACA GTCAAAGTTC
2751 AAGGAGTTGA CTACCTGGCT ACCACAGAGC TCAAGTTGAG TTACCAAGAA
2801 GGGTTCCCAG GAGCAGAGAT TTCCTGCTGG ACAGTGGAGA TATAGAACTG
2851 TTAGGAGCGC CGCTCCCTGC CATGTTGTCC TCGTACGCAG GCAGATGACA
2901 CCTTATGCCA ACAGGGACGC CTGTGAGGCC GAGACCTTGA TGGGAAGAGG
2951 ATGCTCCCTT GTTACAAATA AAGAAGGGCA GTGTGAACCC GA
```

FIG. 5

```
GGTGGCCAAGAGCAGTTCACCTGCTCTGGGGCAAGCCTTGCTTGTG
TTTTAGTGAGTCAGGGCCTCCCCAGGCAGTAAGATGTTGAGTGTGG
AGGCCCAGGCCGCTGACCTGCAGCCCTGTCCCCACAGGCAGGCTG
CATGCTCTTCCCCACATTTCTCCTTGCGAGGTGCGCGTGCTCATG
CTCCTGTACTCGTCTAAGAAGAAGATCTTCATGGGCCTCATCCCCT
ACGACCAGAGCGGNTTCGTCAACGCCATACGACAGGTCATCACCAC
CCGCAAACAGGTGTGCCAGCTGAGGGTAGNCTGCTCCTGCTCCTAC
CCTTGGTAGACCCACTGNCTCCCACTGGTGTGGAATGTGGCATCAA
GGCTGAGTCGGCGNCTGGGGAGGAGCTGTGACGANGCAGTGCCATA
CCCAAATGGGCTCGAGGGAAACNTAGCTTTATAGGGTTCAGAGGGG
CAGAACTAGAGGGTGGGCCTGGGTGTAGAGGCAGGGCAGGAGTGG
GGTGGCAGGTTTGGCAAGAGGCCCAGAGTCTCTGGAGGGTCACAGT
GTTGATGACATCTTTCTNAGAANCCTGCTACTNGCTTAGNCAGCTG
TGGTCCTCTCTNCCACCTGGGGGATACCTGGCNACAGGCNGTGGGC
NNCGGGGGTGAANACTCTGGACCTGTTNAGANTGTCAACAACAAAT
TCTTGACATGGAGTGGTGTCATGGAGTGGNAGGAGGTGANCTGCCG
GGGACTGTGTGGACTGTTGNCCCTAAGCTGCCCTCCCCTGAAGTGC
CTTCTCGCTCTGCCCCAAAACCCAGACCTGAGCCCAACAGCCGGTC
CAAGAGGTGGCTGCCATCCACGTCTATGTGAACCAAGGGGAGATC
CTGTGATTCCGGGTACCCCGGGTGGCCCATTGACAGTGCCGCCC
CCCTGGGGGAGGACTTCTGACTGATACCTCCTGTCTTGTGTGGCAG
GAGAACAGACCAGTGGCCTCGGAGGCTCTTCATGCAGCTCATTCCC
CAGCAGTTGCTGGTGAGGGTCAGGGGATTCCAGGCTGGGGTGGG
CCAAAGACCCTGTGGTGGCTGGTTCAGAGGCCTGCCTGGCTTCCC
CAGCAAGCTAGGGTTCCATAAGAAGCCCTCGGCCTTCCCCAGAC
CACCCTCGTGCCACTGTTCCGGAATTC
```

FIG. 6A

```
GGCACGAGCTTAACTGTGCTAACTTCTGTGATGATCATGTGTGATGAGTATGTGCTCT
CATTTGATTTGTGGGAAAAAGAAAAGAAAAAAATCCGAAGGACACAAAGAGGACT
AATCTTAAACCAGATATCTAGTAGTCACCAAAGCCACACTTTGAATTCGAAAGCTT
AGCACTGTAGCTTAGCTCATGCTATCTTTTAAAGAGAGAATTTAATTATTTAATATAT
GGAAGGACATTAGGCTAGTGTGTCTGGCACATGGTATAAACTCAATAAATGGTGGAC
GTTATCAGTGCTACTATAATGAGTTTAATAATTTGGTTTCATCTCCTTTAATCAGACC
AGTGTTCACTACTAGCTGGGTCTCTGGAATAGGCACAGATATATTCATCTGGAGTGTC
ACACATACTCTGTGCGCGAAAGAGTTCAGAATAGCCCTTCAATAAGCCAATTACTCTT
GCTGTCATCCTTATTTCTTAACTTTCCCTTAGCGTTGCTTTTATGTATCAAACTTTTCT
TCCTTATTTTACGTAATACTTTTAATGACAACTTTCTAGAAATAAGAACTATACCCTA
AAAGATTGAAATATTCTTAGTTTTCTTTATCTACATCAGAATTGTTTAGCTGATACA
ACATACTTATATTGTTTAAGGAATTCTGTTTAATACCTTGGTATTTATAATTTTCATAA
GTTTATTTGTATTAATAGGAACTCTTACAAAGAATGTATAGAAAATAAGCCCCATCAT
TTGTCAGTGTGACAATTTTCCCAGTGTTTAAATTGTTTAAGCTGTTTGTACCCCTATAT
AAGCTCTGTTCCTTCTTTGGCCCTTTCCCCCTTAGCCTAAATCTCCATTTTGCCTGACG
ATCTCTTCCCTGACAAAATGCCTGCTTCTGCGCACTGAGTCACAGTCTACTAAAATGC
ATTCCATTGTGCCCATGTCCCTCTTAATGTGATGACCCCAGACATGACCAGGGCAGAG
CACAGAGGGAGCATCACTTTCTTTGACCAGAGCATCTATTTCCAGCAATGCAGCCTA
AGGTCACATTAGCATTTTTGGCAGCAAAATACACCCTTGGCTCATGCTGTTATGCTGT
CAACCAAATCCTCCATGACTTTTTCACATGAACTCCCATTAAATAAGGCTTCCCACAT
CCGGTACGAATATAGACAGTAATGTGCAGTCTGGTGAAGTTATTTACATAAGTTCCTA
TTAAACATCAGCTAATCTATATTTATTATTTTAGAATATTGAGACAGATTTCTATTCC
CAGCTATATAGATATGGTTTTAGAATACTTTATTATTATTTTTTTAATGTGTCTTCTCT
GAACCCGATAAGAACATAGTCCCAGACAATCTTTAAGTTCAGAGTCTTACAGTTTGT
ATAGAGACCTAGAGGCTAGCTATATTTCTTTAGACATCAACACATCATCAGATAGGA
TCCACCCAAGGCCTTACAAATCCTGTATACTGAAATGCCTTTTCCTGACGATATTCT
GGAGACTGTTAAGTGAATGCGCAGATCTGAACCGAGCCGAGCCTGTAGTGGGGAAGA
GCTAAAGCATGGCAGTTGTCTTCATCAATGATGGAGTCTTTCATTATGTTGTCTCAAA
AGACACATGCTTCAGCCCTGGGTCTCAAAACTCTCATGCTTCGGCCCTGGGTCTCACA
CTCCTGGCTTCCCGAGTGGTCATAGCTAAGACCTTCTCACACTAAATCCCAGGATGAG
CTCATGTTGATGTTCCTGCTTGCTTCTCTGAAATTGGCAGTTCTCGTGGGAAAAAAA
TCTACTTATACTTGTGTGCTTCATAAAGCAACTCGGTAGCAGGGCTTAGGGGTGCTTC
GAGTGTGGCAGTGATAGAGAAGACCGATAAAGCGAAATCTATGATATCTCATACATC
ATTTTAATTATTTAAATTACTTTTGTTAGTACACAAAGTATTTGTTAGTACACCCTG
TTTATCTATGTGTATACTCTACCTTTCGCATACACTGACTTCATTTCTTTTTCTCCTCA
CCCATCCTGATGAGCTGCTCTCCTCCAGACAAGCTCTGGCAGTTTTAAAGTCACGTG
TGTATCTTTTAACTCTAGCTTCTGCCTATTAGACAAAACAAGATACTTGTCTTTCTCCC
CATCTCCCTCCTTTTGTTTAATTCTCCTCCAGCCCTACATGGATCCCCCTTGACCTCGT
GTCATATATCTAAATCTGTATAAATAAGAGATGATTTAATCTACGTTCTATGTACAA
AAGAGAATATAAATGCTCGTCTTTCTGAATCTGTCTTATTTGGTTTCACACAATATCT
```

FIG. 6B

```
GCTCTCTTTTACCGCAAATGGTATCATCCGTTCCCTTTACACGTTGAAGAAAATTTC
ATTTGTGTGTGTGTGTGTGTGTGAACTATATATTTTACGCTATCTGGTG
AGGAACATCAAGGCCAAGATATGGATCTTGGCTATTGTAAAGAGTGTAGTAAGAAAC
ACAACCGTATAATCATCTTCTGTGTGCATGCTGGCTACAATCCTCACCTGTG
TACCCAGAGTGAGAGCTGGACCACATGGTAATGCAACCTGTAGTTATTATTTAATGT
GTACTTCTTGTTTAATGTTTAAAGATACTACTTATTTAAGTGTATGTGTATGGATGTT
TTATCTATGTGTTTGTCTGTATATAGTGGGCACGTACTGGTCTCAGACGCCAGAGGAAG
GCATCAGAGTCCCTGGGTTGGAATTAAAGATGTTTGTGAGTACCTGCCGTATCCTG
GACTTCAAACCCGGGTCTCTTCAAGAGCAGCCAGTGCTCTTAACCACTGAGGATCTC
TCCAGCCTCATCGCTGATTTAGGAAGGACTTTTACTGATTTGGAGTAGCTGTAGGCAA
TGCAGTCTATGACGATTCCTTTAGCAGTTCTTGTTTTCTTAATGATAGCCATA
CTGATTGCTGAGATTACAGCAGCACTAGCAAGCTGGAA
```

FIG. 7

```
CTCGAGTTTTTTTTTTTTTTT GGAGAAGGGNAACATTTATTCATTC          50
AACAAATNTTGATGACCTGATGGGGNAGATAACTGAGCTAGTCAGCGCGT       100
AGGTAGCAAACATAAGGNTATAGTACCCCAGNTAATGGTCTNCCCACATG       150
TCACTGAAGGAGTGTCAGTTCTCAGCATTTACCTTTAATTTAATTTTT         200
ACCTCTAAATGCGCTTAGGAGGCTACCCACAGTTGATGACAAACAGTGT        250
AGCCAGGCATGCCAGAGAACTGTTACCAGCAGAACTTTTGCCGACTGTAGC      300
TGGCAGTGTTCTCAGTAGTGCAGTTCATGCCTGGTGGGTGTAACTAGGGT       350
ACAACGAAGTCACTTTGAACTCTTTTGCTAACTAAATAAGCCAAATAAAC       400
AAATCATGAAATACTGATTAGCAATGCAATATTTCATGGCATGGAAGAG        450
CTTCGACTTCTCCATCGGTGACAAGGAGCAGCTTCTGAAGGAAGGTCTG        500
GAGAAAACAAGTGACGGGGAGCTCCGAGAGCCCTGAACACGTCACTCAA        550
CAGCACTGGCGGTTGACACAGTCTGTGTTCCAGCAGTCAGTCTCAGTGGAG      600
AGTGCCAAAGGGTGGGCAGACAGNCAGNCCTACTCTTCTTCATCTCCAGAT      650
GGCACTTCCAGGCCCACGGTTCTTAGCACTACAGATGTTGCAGTATTGTG       700
CAGGAGCATTCATGCTCCGGCATAGGCAGGCACTCCTTGTGGAACATGTGC      750
CGGCAGTGGAAGACCACCACGCTGAAGGGCTTCNCTGCATCTGTTGGGAG       800
GATGGGAGAAAGGCATGATTCACAGATATTCTTCATCAACCAGAACGC         850
CTTTCATTTGGGTTCGGNGCATTTTTCACACCAACGACAATGAGTCA          900
GCTACGAGGATTTCTTGCAGCCCTTCCCGAAGCAGAATCTTCAAGTTATA       950
ATCTTGCAGAATTTAACCAAGGAATCTCTCAAATTGGGAATCTCCATTC       1000
CTTCCTTAATTCGGTGGATAAGTAGAATCGGTCCACATGTGTGCCAATG       1050
TTGTTCAACAAGCCAGTGATAAATGGTGGTTTGTCGATGGAGTATAGAAT      1100
CAGATCTTCTCGTGCCGAATTC                                  1122
```

FIG. 8

```
CTCGAGAGATGCCCCACAGTCCCTCAGGACCCGAGTCAGGTAATCTGCCT      50
TTGCCTTAGTGACCTCCTTTCTGGGCGAGTATACCATCCACTTTCCTC       100
CCTGACAGGCAGTTCAGTAACCAACCCTTTCATTCCTCCTTCAGTTGTC      150
AAAGACAAGTTAACATCCAAGACTAACAAGCAAGATGACTCAGGAGCATG     200
GNCTCTGGGTTCCCCTGGCACCATGCTGGATAGCTTAAGCTCCTAGTTAAGGCTGAC    250
TTAGCTCTTAGCAACCTTGGTTGGGATAGCTTAAGCTCCTCATCTCCACTTTC 300
CTACCAAACAGAAAAGAATTTGAGTCCTCTTGCTATGAGGCTCTCGCTCC     350
CATCTCAGGCGAGCTTCCCTGCCCCTCACCCAAGCTTGGGAGGTAGAGTTA    400
TGGAGAGGCAAGGAAGCAGGACTGGAAAGATAGACTTATGGATCCACCA      450
CTCATAAAGTCACAAAGTCCCCTCACCTGCTAGACTTAGACTCTAAAT       500
CATTACGTTGTCAACAGAGGTGACTCCTCAACCACAAGAGCCTGTAG        550
TGAGCTTCAAGAGAAGAGGACAAGNCAGACCTGGACTGCATGACCTTG       600
CACCTGTGATGAAGTCACAGCAATAGGTGATGCTCAAAAGCCCAATAA       650
AATGCAAGACAGNCAAACAGAAGCCCTGTCTGTCCCCATTGGTGGGTAAT     700
GTAGCTGATGTGGCTGGTTCCTCCCTTCCTTGACTTCACCCTGACTATGGGA   750
ATTGTCCTTCAGTGCCTCGTGCCGAATTC                          779
```

FIG. 9

```
CTCGAGAGGTGAAGGCAGAGAAGTATCACAAGTTCAAGTTCAAGGNCAGCCT        50
GGGCTTCACAAGACCCAAAAAAATAAATATGAGGNCAGTCCAGGCTGGA          100
CTCAGGTCACTGCTGTGCTGAGCCATCGTCAGAGAAGTTTCTTTNNT            150
TTTGATAGGAGCTAACAGCCACCCACANCTGACAGNCTGCAGTGAGT            200
GAGTGAGTAAGTGACCTAAAAGTGATGCTTCATTAATCTCCCCTCCCA           250
GGCNTCAGGGAGCTCTGAGGAAGAGGCAGAAAGATGGTGAGAGCCAG            300
CAGGGATGGAGGAAGCCAAGAAGCAGTGTCTTCCGACACAGGACTG             350
GCATTTAGGAAGTCACAGAGGCTGTGCTGAGAGAGCAGACAATTCAACACGGNCTCCCA 400
AGCTGGCTGAGATTCCAGTGCTATCTCCAACTGATATCCACTTGCAAAGAAAAA     450
CCCCTAGNCAAGAAGTTCAGTGGNTAGAGAGATGGCTCAGTGGNTAAGAGCACTGACT 500
ATTAGGGGNTAGAGAGATGGCTCAGTGGNTAAGAGCACTGACT.........       544
................................................           600

.....TANAAAATAGAAATNGCANATTNGNTNNGANGTTNGCNAAATNGC         1200
TGAGAAATGGCCAATTGCTGGAAAACTTGCAACATTGCCTGGAGAACTG          1250
CCAAATTGCCTGGAGAGCTGCCAAATTGGCTGGAGAGCTGCCTACATGG          1300
CCTGGAGAGCTGCCCACATGTCCTGGAGATCTGCCTACATGTCCTGGAGA         1350
GCTGCCAACATGTCCTGGAGATCTGCCTACATGCCTGGAGAACTGCCTA          1400
CATGACCTGGAGAGCTGCCACATGGCCTGGAGAGCTGGCTACATGACCT          1450
GGAGAGCTGNCTACATGCCTGGAGAGCTGGCTACATGCCTGGAGAGCT           1500
GGCTACATGCCTGGAGAGCTGGCTACATGGCCTGGAGAGCTGGCTACAT          1550
GGCCTGGAGAGCCTCCCAGCAAGCCCTCTCTAAGCCCGAATTC                1592
```

FIG. 10

| | |
|---|---|
| CTCGAGATGCATTAAAGCTTTGNTGCAAGGATCCGAGTGTCCTGTG | 50 |
| TGTGTCCTCACTGGCGAGACCCTTATCACACAGGGACACCCCTTAGG | 100 |
| TTGGAGTTTCCTTGTAATGTCCACTATACGTCTGCTTTATACAATAATA | 150 |
| TTGNTTAAATTGNCTCTATGAAATACCTCACTTTCCTTATCTGTAT | 200 |
| TGATTGAAAGTTTTGGTGGATGTAATAGTTTGGGCTTGGATCTGAAGTCT | 250 |
| TTTAGAGTTTATTGGACATGTGCCTNGATTCATTGGNTTNAAATCNTCC | 300 |
| ACNACTTGGGGTGTAAAGGTTACCCACNCNATTANTGGAGGTTCTTCTG | 350 |
| AGTTCAGAGANAANGANTGAGCCACCNGGAATTCT . . . . . . . . . | 400 |
| . CCCTAAACACACTTTGATCATTCCTGCCTAACCCTGCCAGAGGAAATAT | 1550 |
| TAATACCCTGTAGTACCAAAGAATACAAATAAGAAGAAGACTGNTCTCT | 1600 |
| CATGTCTGGAGGAAGTTTGGTGAAGGAGTCTTCTGTTTGCTCACATAGGA | 1650 |
| GAGATCTAATACAGCCACTATCCATAATTAAAAATCTCTGTGAGAGAGGC | 1700 |
| ATGACGAGGTTCCCAGTCTGTCAAGGATGTGAATATGTGTTNCCCTG | 1750 |

FIG. 11

```
GAATTCNGCNTTGGGTACATGGACCNGGAGAGCTTGGNTACATGGCCTG        50
GAGAGCTGGNTACATGGCCCGGGAGCTGGTTNATAAACCTGGGANGT         100
TGGGTTNAATGGCCCCGGGANGTNGGTTNAATANACCNGGGGAGG.....      146
.........TGTCTGAAANAGTGGNCACGTACT                       200
GTTCTCAGACCCAGNGAAGNCATCAGAGTCCCCTGGGGTTGGAATTAAA       250
GATGTTTGTGAGTCNCTGCGTGTATCCTGGACTTCAAACCCGGTCTTCT       300
TCAAGAGCAGCCAGTGCTCTTAACCACTGAGGGATCTCTCCAGCCTCATC      350
GCTGATTAGGAAGGACTTTACTGATTTGGAGTANCTGTAGCCAATNCA        400
GTCTATGACGATTCCTTTAGCAGTTCTTGTTCTTTCTTAATGATAG          450
CCATACTGATTGCTGAGATTACAGCAGCACTAGCAAGCTGGAACTCGAG       500
```

FIG. 12

```
CTCGAGNTTTTTTTTTTTTTTTTTTTTTTTTTTTTTTTTTTTTTTTTTTTT                 50
TTTTTTTTTTTTTTNNNNAANAAANTTTAAAGTTTTTTTTTTTAT                      100
NAAANNTTCCAAGGGGGANGGGTTAGAAGANAGCCANAGCCTGGNC                     150
CCCCTGCCAGAAAAACCAGAGGGGGTTGATGTCCCCAAGTCCAGTTG                    200
CCCCCCCTGAAGAAGTTCCCCACGATTCCCTGGTGGCCCCCGGAGTAC                   250
TCACCCTGAAGAAGTTCCCCACGATTCCCTGGTGGCCCCCGGAGTAC                    250
GTCCAGAGTGTCACCCTTCCATTGGGAGCTGTGGGAAGGGNGTGGGNT                   300
CCCTCCCCAGNGGGCCCCAAACCCTCTCCTGAACAGNTCCTGATTTCTG                  350
aCCATCTTTCCAATTCCACGGATTCAAAGAGCATGACCCTAGGTAAGCAA                 400
GCCAGGTCAAGAGCATTGTCTGNAGGAAAAGGAAGGGTCCCTG                        450
GCCTCGTGCCGAATTCC                                                  467
```

NUCLEIC ACIDS ENCODING PROTEINS FOR EARLY LIVER DEVELOPMENT

FIELD OF THE INVENTION

This invention relates to proteins isolated during early liver development and the genes coding for them, and to methods for their use in diagnosing and treating liver disease and other disorders.

BACKGROUND OF THE INVENTION

In the United States and other countries, end stage liver disease due to infection, genetic defects or alcoholic consumption is a major cause of widespread morbidity and mortality, causing great potential hardship and economic loss to millions of people throughout the world. In addition, numerous other diseases, including biliary problems and blood disorders, are associated with disruptions in the many functions carried out by the liver, including iron transport, hepatocyte formation and hematopoiesis. In general, severe problems associated with a breakdown of liver function are practically untreatable, and require a liver transplant as the only cure. However, in light of the great disparity between the number of patients needing liver transplants and the number of donors, thousands upon thousands of people are denied this operation, and transplantation is at the present time not a practical approach to the problem.

At the same time, the precise nature of liver development and the role of early developing liver proteins has not been well understood. To date, no growth factors specific to the liver have been identified or isolated, and the precise molecular mechanisms behind hepatocyte (liver cell) formation remain to be elucidated. There thus has been a long felt need to identify and understand the changes in gene regulation and expression in the developing liver, including the determination as to which genes are switched on and off as a hepatocyte forms and a liver develops. Accordingly, isolating and identifying the genes and proteins which play critical roles in early liver development would be beneficial in understanding the effect of gene regulation and expression in the differentiating liver, and in diagnosing and treating many diseases states involving the liver and liver functions.

SUMMARY OF THE INVENTION

Accordingly, it is thus an object of the present invention to provide genes comprising the nucleic acid sequences encoding early liver developmental proteins, including the liver proteins known as elf 1–3, liyor-1 (145), pk, protein 106, and praja-1.

It is further an object to provide isolated and purified early developing liver proteins encoding by the above genes.

It is still further an object to use the early developing liver proteins of the present invention to provide liver-specific growth factors for application in diagnosis and treatment of liver disorders.

It is still further an object to provide methods of diagnosing and treating end stage liver disease using the early developing liver proteins of the present invention. It is even further an object to provide methods of diagnosing and treating other liver disorders and other diseases, including carcinoma, degenerative neurological disorders, anemia, and ataxia, using the early developing liver proteins of the present invention.

These and other objects are achieved by virtue of the present invention which provides genes coding for various proteins which are involved in the differentiation of the developing fetal liver, including the proteins known as elf 1–3, liyor-1 (145), pk, protein , praja-1, and a number of other stage-specific genes coding for early-developing liver proteins, and methods for their use in diagnosis and treatment of a variety of liver diseases and other disorders.

BRIEF DESCRIPTION OF THE DRAWINGS

The present invention will now be described in detail with respect to preferred embodiments thereof, which are to be taken together with the accompanying drawings, wherein:

FIGS. 1A–1B represent the nucleic acid sequence encoding the liyor-1 (145) protein (SEQ ID NO:1 and SEQ ID NO:2) in accordance with the present invention.

FIGS. 2A–2E represent the nucleic acid sequence encoding the elf-1 protein (SEQ ID NO:3 and SEQ ID NO:4) in accordance with the present invention.

FIGS. 2F–2I represent the nucleic acid sequence encoding the elf-2 protein (SEQ ID NO:5) in accordance with the present invention.

FIG. 2J represents the nucleic acid sequence encoding the elf-3 protein (SEQ ID NO:6 and SEQ ID NO:7) in accordance with the present invention.

FIGS. 3A–3B represent the nucleic acid sequence encoding the praja-1 protein (SEQ ID NO:8 and SEQ ID NO:9) in accordance with the present invention.

FIG. 4A–4B represent the nucleic acid sequence encoding the pk protein (SEQ ID NO:10) in accordance with the present invention.

FIG. 5 represents the nucleic acid sequence encoding the 106 protein (SEQ ID NO:11) in accordance with the present invention.

FIGS. 6A–6B represent the nucleic acid sequence encoding gene 20 (SEQ ID NO:12) in accordance with the present invention.

FIG. 7 represents the nucleic acid sequence encoding gene 36 (SEQ ID NO:13) in accordance with the present invention.

FIG. 8 represents the nucleic acid sequence encoding gene 41 (SEQ ID NO:14) in accordance with the present invention.

FIG. 9 represents the nucleic acid sequence encoding gene 112 (SEQ ID NO:15) in accordance with the present invention.

FIG. 10 represents the nucleic acid sequence encoding gene 114 (SEQ ID NO:16) in accordance with the present invention.

FIG. 11 represents the nucleic acid sequence encoding gene 118 (SEQ ID NO:17) in accordance with the present invention.

FIG. 12 represents the nucleic acid sequence encoding gene 129 (SEQ ID NO:18) in accordance with the present invention.

DETAILED DESCRIPTION OF THE PREFERRED EMBODIMENTS

In accordance with the present invention, early developing liver proteins and the genes coding for them have been isolated and sequenced, and these genes and proteins can be utilized to diagnose and/or treat a wide variety of liver disorders and other ailments. In general, the present invention arose from the investigation of liver formation during embryogenesis when the liver and other organs are in transition from an undifferentiated state to a differentiated one. This setting captures the phases of liver formation beginning with ordinary sets of endodermal cells. In addition, the early steps in tissue differentiation are closely related to the process of oncogenesis and tissue repair, and thus the isolated early developing liver proteins obtained in accordance with the present invention should have implications for diagnosis and treatment of a range of diseases from end stage cirrhosis to hepatocellular carcinoma and many other disease conditions.

In the identification and isolation of the liver proteins of the present invention which are useful in early hepatocyte formation, the first step that was taken was to "capture" and analyze gene expression at different stages of early liver formation, particularly at those stages that emerge in the range of about days 9 through 14.5 in the mouse. In this regard, four embryonic liver cDNA libraries were constructed, such as at days 10.0, 11.5, 12.5 and 14.5 post coitus, and after subtractive hybridization, isolation of a group of stage-specific, liver restricted clones were isolated. As will be set forth in more detail below, sequence analysis has revealed that these clones encode a series of early developing liver proteins, which are generally "stage specific", i.e., they appear only at specific stages of development and not other stages, including elf proteins 1–3, liyor-1 (145), pk, protein 106, proteins coded for by genes 20, 36, 41, 112, 114, 118 and 129, and praja-1, as will be described further herein.

The initial project to identify and isolate developing liver proteins had four main objectives: (1) to construct early embryonic liver libraries; (2) to screen and characterize these early embryonic liver libraries with a group of probes comprising known growth factors (IGF-I, IGF-II, and IGFBP-2) and transcriptional activators (C/EBP and LFB1), known to be expressed in the developing liver; (3) to carry out subtractive hybridization utilizing these cDNA libraries and analyze subsequent subtracted clones for stage specificity by southern blot hybridization, sequence, transcript size, abundance, and tissue distribution; and (4) to develop a functional assay for these subtracted genes using embryonic liver explant cultures.

With regard to the main objectives of the invention, it was decided to focus on the four stages of liver development, particularly around days e10, e11, e12 and e14 (embryonic days post coitus) in developing mice. These four stages are defined developmental time points representing phases of liver development from undifferentiated mesodermal/endodermal cells to a well developed and differentiated fetal liver. These stages have generally been categorized as follows: (1) at around e9–10, a change in cell polarity occurs; (2) at around e10.5–11, invasion and migration of endodermal cells into surrounding mesenchyme occurs; (3) at around e11.5–12, pseudolobule formation, cords of hepatocytes form together with early sinusoids; and (4) at around e12.5–e14.5, the liver is marked by hematopoietic foci and fully differentiated fetal hepatocytes. cDNA libraries representing these stages would therefore represent "captured" mRNA species expressed in greater abundance during critical time periods for hepatocyte formation, enabling their isolation and providing a method for analyzing the changing pattern of gene expression during liver development.

Another aspect of the present invention is the development of useful methods of diagnosis and treatment of liver disorders and other diseases made possible by the identification and isolation of the genes for early developing liver proteins of the invention and the expression of those genes. In accordance with the investigations made regarding these early developing liver proteins, it is clear that the different genes and proteins identified are important for different aspects of liver development and can thus be utilized in treatments of the appropriate disease. During embryogenesis, the liver generally develops from a foregut diverticulum, and comprises four main cell types: the first is the hepatocyte, or endodermal lineage; the second are biliary tree canalicular cells or bile duct cells, the third are hematopoietic cells, and the fourth are the Kupffer cell/Ito cells. As will be set forth below, of the early developing proteins isolated and obtained in accordance with the present invention, it is believed that the elf proteins are important for the formation of the biliary tree, as shown by antisense experiments; praja-1 appears to be important for iron transport and essential for hepatocyte formation as well as hematopoiesis; liyor-1 (145) and pk appear to be important in Ito cell formation and fibrosis.

Accordingly, in accordance with the invention, it is contemplated that elf proteins 1–3 will be useful in the treatment of disorders such as cholestasis, biliary stones, hepatic obstruction, stricture, primary biliary cirrhosis and primary sclerosing cholangitis. In addition, the proteins praja-1, liyor-1 (145) and pk will be useful in treating end stage liver disease, anhidrotic ectoderm dysplasia, hepatocellular carcinoma, as well as anemia, such as sideroblastic anemia, ataxia, e.g., spinocerebellar ataxia, degenerative neurological disorders, anhidrotic ectoderm dysplasia, and hemochromatosis.

Even further, it has also been discovered that the protein praja-1 has been identified in cancerous colon tissue, which normally does not produce this protein. Accordingly, it is contemplated that in accordance with the present invention, a method of detecting and diagnosing colon cancer is provided wherein colon cells or tissues are taken from a patient being tested, and these cells or tissues are screened to determine the presence or absence of the praja-1 protein. Identification of praja-1 in the colon cells or tissues will allow for a determination of whether the cells are cancerous since praja-1 will generally not be detectable in non-cancerous colon cells.

In the preparation of cDNA libraries in conjunction with this invention, it was necessary to utilize the four developmental stages discussed above in order to isolate key early developing liver proteins that affect the formation of hepatocytes and the liver. Although these studies were performed on mice, the relevance of the stages of liver formation to human development is shown in the following summary of these investigations:

(1) Day 10 post coitus (e10, 34–39 somites) (Human day 27):

In the mouse, the primary liver diverticulum appears during the 10th day of gestation. It develops from a foregut indentation in the endoderm which arises at e7, at the boundary between the embryonic and extraembryonic region, anterior to the developing heart rudiment. At this stage, although the cells are committed to the formation of fetal hepatocytes, they are still epithelial in nature and the liver diverticulum is not viable in the absence of the surrounding heart mesenchyme. As this is the earliest stage possible when hepatocytes are undifferentiated, it was considered to be of great importance: some cells are poised to differentiate into hematopoietic cells and others into hepatocytes. Accordingly, a day 10.0 library was constructed in lambda Unizap, and no prior group had ever constructed a cDNA liver library at this stage.

(2) Day 11.5 post coitus (e11.5. 40–44 somites) (Human day 32):

This stage is characterized by rapid growth of the liver. Soon after the formation of the hepatic bud, the endodermal cells proliferate, disrupting the membrane separating the epithelium from the septum transversum, with the epithelial cells migrating into the mesenchyme. The liver at e11.5 consists of broad hepatic cords separated by large sinusoids containing nucleated erythrocytes. Hematopoietic foci are found intermingled with the hepatic cords. A cDNA library was constructed in lambda gt1O and lambda Zap from embryonic livers obtained at this stage, since although cells are proliferating rapidly, they still have not attained a fully differentiated fetal state.

(3) Days 12.5–13.0 post coitus (e12.5, Human days 35–45) (Embryo size: 7–9mm):

This stage is easily recognized by early signs of finger development as well as by the anterior indentation of the footplate. At this stage, the liver is well developed, all lobes being clearly visible; it contains many megakaryocytes as well as cells with erythropoietic activity. A CDNA library at e12.5 was constructed in lambda gt10 and lambda Zap as this was the earliest stage where fully differentiated fetal hepatocytes are seen.

(4) Day 14.5 post coitus (e14.5, Human days 51–57) (Embryo size: 20–32mm):

At this stage, individual, separated forefoot fingers can be seen; hair follicles in the skin can be recognized and the umbilical hernia is very conspicuous. This stage represents a well differentiated fetal liver containing scattered blood-forming foci. A cDNA library of this stage was constructed in lambda Unizap in order to facilitate subtraction with the day 10 library which was also constructed in lambda Unizap (Stratagene).

(5) Adult mouse liver:

At birth, day 19, there is a major "switch" in the expression of a large number of genes. From now until the stage at which adult liver is formed, enzyme synthesis of the urea cycle and gluconeogenesis are upregulated. Adult liver is no longer a center for hemopoietic activity except in pathological situations and hepatocytes do not enter de-differentiated states, though the liver still has regenerative capacity as seen in partial hepatectomy.

In conjunction with each of these stages of development, RNA was recovered from each stage, and the quality of the RNA obtained following dissection was assessed by Northern blot analysis using mouse Beta Actin from the Chiba Cancer Center Research Institute, Chiba, Japan. Table 1 shows the RNA yields obtained. The CDNA library construction at days e11.5 and e12.5 of the embryonic liver was carried out by conventional techniques, and the libraries of the day e10.0 and adult mouse liver were obtained using the Stratagene Unizap cDNA library kit. RNA yields and cDNA library size fractionation are shown in Tables 1 and 2, below.

TABLE 1

RNA yields obtained for each stage

| STAGE | NUMBER OF LIVERS | TOTAL RNA (RNA per embryo) | POLYA + RNA (% of total RNA) |
|---|---|---|---|
| e10.0 | 608 | 63 mg (1.04 mg) | 26 mg(4%) |
| e11.5 | 48 | 60 mg (6.7 mg) | 16.8 mg(3%) |
| e12.5 | 28 | N.D. | 40 mg(approx) |
| e4.5. | 20 | N.D. | N.D |

TABLE 2

Early embryonic liver cDNA libraries and adult mouse liver library

| LIBRARIES | INITIAL SIZE | SIZE AFTER AMPLIFICATION OF 2X106 CLONES | VECTOR |
|---|---|---|---|
| e10.0 Unizap | 6.1 × 106 | 2.0 × 1010 | Lambda |
| e11.5 | 5.2 × 106 | 1.6 × 1010 | Lambda Zap |
|  | 4.1 × 107 | 2.0 × 1011 | Lambda gt10 |
| e12.5 | 8.0 × 106 | 1.6 × 1011 | Lambda Zap |
|  | 1.6 × 107 | 4.0 × 109 | Lambda gt10 |
| e14.5 Unizap | 7.0 × 106 | 2.0 × 1011 | Lambda |
| Adult Unizap | 5.0 × 106 | 2.1 × 1010 | Lambda |

The cDNA inserts for e10.5, e11.5, e12.5, e14.5 post coitus stage mice and the adult mouse liver were size selected on a Biogel A150 column (>500 bp) prior to ligation to the vector. Actin frequencies for the libraries are given in Table 3.

Qualitative analysis of cDNA libraries utilizing known developmentally regulated cDNAs were carried out in order to establish developmental profiles of important "early" genes that are significant in development, and these libraries were then screened with a specific number of probes. The following probes were obtained and used for screening these libraries, including: Insulin like growth factor I (IGF I), obtained from Dr. Derek le Roith (NIH); Insulin like growth factor II (IGF II) and IGF II binding protein –2(BP- 2) both obtained from Dr. Matt Rechler of NIH; LFB 1 obtained from Drs. Monaci, Nicosia and Cortese of EMBL in Heidelberg, and the C/EBP probe from Dr. Darnell of the Rockefeller University in New York, N.Y.

TABLE 3

Clone frequencies for day 10.0, 11.5 and 12.5 libraries
(Carried out on Duplicate Screens)
Positive cDNA clones per 100,000 poly A+ containing cDNA clones

| Probe | e 10.0 | e11.5 | e 12.5 | Adult |
|---|---|---|---|---|
| IGF I | N.D. | Nil | Nil | N.D. |
| IGF II | 3 | 0 | 4 | 0 |
| BP 2 | 1 | 1 | 0 | 7 |
| LFB I | Nil | Nil | 1 | N.D. |
| C/EBP | N.D. | 2 | 5 | N.D. |
| Beta Actin | 120 | 130 | 246 | 270 |

N.D. = Not Done

The data shows that IGF I was not detected in any of the embryonic libraries, while IGF II was detected in increasing clone frequency from e6.5 to 8.5 (8 at e6.5, 8 at e7.5 and 38 at e8.5—data not shown) and was also detected in the e10.0 and e12.5 libraries (3 at e10.0 and 4 at e12.5—see Table 3). IGF II was not detected in the adult liver library. Interestingly, BP2 clone frequencies are similar to IGF II in the early e6.5, e7.5 and e8.5 libraries (data not shown), but in the liver cDNA libraries the clone frequencies differed, for BP2 only one clone per 100,000 being detected at e10.0 and e11.5, while 7 were detected in the Adult Liver Library compared to the greater numbers for IGF 11. This implied that its temporal and spatial expression in the embryo and fetus is different from IGF 11 and this was subsequently confirmed by in situ studies. LFB I was detected in the e12.5 library, but at one clone per 100,000 screened, which implied that it is not present in mitogenic cells, but that its level was regulated and increased from birth onwards.

C/EBP was not present in the e6.5, e7.5, e8.5 or e10.0 libraries (data not shown) but was suddenly detected at day e11.5 and e12.5 in low abundance (about 2 clones/100,000 at e11.5 and 5 at e12.5), implying that while it is expressed, its level also may be regulated, albeit downward, in embryonic stages. Lastly, Beta Actin was used as a reference: all seven libraries had similar Beta Actin frequencies from 120–300/100,000 clones which is considered representative of such embryonic libraries.

Next, identification of stage specific clones by subtractive methods was carried out, and two subtracted libraries were then constructed. Two rounds of subtraction were carried out, and the resulting subtracted libraries comprised 64 clones (e11.5–12.5), and 174 clones (e10.5–14.5). Further characterization of these clones was carried out as follows: (1) Southern hybridization; (2) sequencing; (3) Northern analysis; (4) Zoo blot analysis; and (5) In vitro translation of protein.

In the Southern blotting of these clones, thirty-four clones were shown to be stage specific and not containing mitochondrial, ribosomal and globin sequences. DNA sequencing of these thirty-four stage specific clones was carried out in order to identify clones bearing homology to known developmental genes (such as cell polarity genes, homeobox genes, etc.), and the first 400 base pairs of each clone were sequenced. A detailed analysis was then carried out with respect to some of the clones which form a part of the present invention, including liyor-1 (145), protein 106, pk, and praja-1, since these clones exhibit true stage specificity and appear to belong to a set of genes encoding signal transduction proteins, which are of great interest in development currently, due to studies demonstrating their importance in cell lineage. Other stage-specific proteins which are coded for by genes in accordance with the invention are discussed further below. Studies carried out with regard to proteins such as praja-l and elf, as well as other early developing liver proteins, have elucidated the sequence of these proteins, as will be set forth in more detail below.

As an example of the tests used to elucidate the developmental expression of these liver proteins, the protein liyor-1 (145) was tested to determine whether these transcripts are differentially expressed during development, specific for mesoderm or endoderm derived tissues, or are expressed in adult mouse and human organs. Accordingly, tissues from mid-gestational embryos were analyzed to determine the role of 145 in liver development. In these tests, tissues were dissected from day 11 onwards, as it was at this stage that discrete hepatic, cardiac and other tissues could be dissected with ease, with subsequent RNA isolated being of good quality.

RNA hybridization with liyor-1 (145) DNA in different mouse tissues was studied by using polyA RNA obtained at various developmental stages using a 32P-labeled 1.1 Kb insert representing protein 145. The specificity of the developmental changes in the steady state levels of 145 was evaluated by also measuring the relative levels of Actin. This revealed a 2.4 Kb transcript at high stringency washes. Scanning densitometry of the respective bands revealed that maximal expression of 145 occurred in liver and heart, less so in other tissues, but specifically on day 11 and in decreasing abundance at days 12.5 and 14.5 (when Northerns were developed 1–2 months later).

Further characterization of the distribution of protein 145 RNA in adult tissues and its conservation in evolution has involved RNA analysis of adult mouse and human tissues. The protein 145 hybridizes to adult liver, kidney and testis as a 2.4 Kb transcript in liver and kidney and a 2.6 Kb transcript in adult testis, in very low abundance: both blots were developed after being exposed to film for over a month at $-70°$ C. Similar tests conducted with regard to the elf protein and the nucleic acid coding for it showed that elf DNA is generally conserved across many different species, including human, monkey, rat, mouse, dog, cow, chicken and yeast, and is represented in all species studied except rabbit.

Finally, in accordance with the invention, a functional assay was established for subtracted genes with the goal to establish mouse embryonic liver explant cultures in the laboratory, as this is usually considered the major hurdle for antisense experiments due to the need to dissect extremely small tissue sections at day 9.5 when the liver bud is 0.2 mm. In this regard, the interactions of the neighboring cardiac mesoderm and foregut endoderm were studied and the subsequent changes in cell type specific gene expression were characterized, particularly with respect to alpha-fetoprotein and albumin expression, and partially with respect to epithelial basement membrane components. Methods of culturing liver explants in accordance with the invention are described below. The results obtained in these tests have shown that when cultured in the complete absence of mesodermal derivatives, hepatic endoderm deteriorates rapidly. Only 2 out of 15 such liver explants survived. Hematoxylin and eosin staining showed a necrotic endoderm with no apparent signs of hepatic differentiation. When associated with the surrounding mesoderm particularly cardiac mesoderm (en bloc dissections), the endodermal cells had proliferated and invaded the mesodermal strands. Hepatocytes were seen to be organized in cords separated by sinusoids with pseudo-lobule formation. All 15 out of 15 cultures from en bloc dissections were completely viable. These studies confirm prior explant studies demonstrating the necessity of surrounding mesoderm for liver formation.

Accordingly, cDNA libraries have been constructed for the four main stages of liver development, e10, e11.5, e12.5, e14.5 and for adult liver in the mouse. These have been shown to be truly representative of their respective mRNA species, by meticulous analysis utilizing initial RNA blot analysis, size fractionation, quantitative, and qualitative analysis. Northern analysis confirmed the stage specificity, and restricted expression of their transcripts: for 145 this comprised a 1.35, and 2.37 Kb transcript restricted to midgestational brain and liver tissue, and adult mouse and human Northern blot analysis revealed 145 transcripts in extremely low abundance in liver, kidney, testis. Further tests with regard to protein 145 reveals its sequence identity of 53% (20 S.D.'s) to rat Phospholipase C-$\gamma$ (PLC-$\gamma$), and amino acid alignment of conserved section of 145 to PLC-$\gamma$ identifies a split pleckstrin homology (PH) domain. Protein 145 (liyor-1) bears 99% identity at the amino acid level to the PH domain at the amino terminus of PLC-$\gamma$. The PH domain is an area of 100 amino acids that has been found in a number of proteins including serine/threonine kinases, GTPase activating proteins, phospholipases and cytoskeletal proteins, and is thought to be involved in signal transduction. Nuclear magnetic resonance spectroscopy has revealed that the PH domain of P- fodrin is an electrostatically polarized molecule containing a pocket which may be involved in binding of a ligand. Of immense interest is the fact that this pocket is related to the peptidyl-prolyl-cis-trans-isomerase FKBP in which this pocket is involved in the binding of the macrocyclic compound FK506. Accordingly, it is contemplated that protein 145 may indeed bear a pocket for 'natural' ligand similar to FK506 and thus appears to be a potential factor for hepatocyte differentiation.

PLC-γ is regulated by a combination of SH2- domain dependent complex formation with tyrosine phosphorylated receptor tyrosine kinases, and its subsequent phosphorylation on tyrosine residues. An unique feature of PLC-γ and protein 145 is that both contain a split PH domain, which in the case of the PLC fills the gaps between the SH2-SH2-SH3 region and the surrounding X and Y catalytic domains. The SH2 domains mediate the high affinity interaction of PLC-γ with activated growth factor receptors such as epidermal growth factor (EGF) or platelet derived growth factor (PDGF) receptor. The PH domain similarly may be utilized as a specialized noncatalytic domain directing complex formation between protein kinases and their presumptive targets during liver development. In addition, the area of complete identity and split PH domain in 145 and PLC-γ is conserved in a number of other proteins through to TOR2, an essential yeast PI 3 kinase, and to v-abl. A parallel can be drawn to the SH2 domain: that proteins associating with activated growth factor receptors have quite distinct enzymatic properties, are structurally unrelated within their catalytic domains, yet contain a similar noncatalytic domain of approx 100 amino acids, called the src homology (SH) region 2. The SH2 domain was first identified in non receptor protein tyrosine kinase like Src and Fps, by its apparent ability to interact with the kinase domain and phosphorylated substrates. It is believed that during the evolution of cellular signaling mechanisms, the acquisition of SH2 domains conferred on PLC-γ and GAP the capacity to interact with transmembrane tyrosine kinases and therefore couple growth factor stimulation to PI turnover and the kinase pathway. PH domains are similarly conserved and may be utilized in the same way that SH2 domains are.

As indicated above, the protein liyor-1 (145) appears to be important in Ito cell formation and fibrosis, and is thus thought to be useful in treating end stage liver disease as well as other conditions including hepatocellular carcinoma, anemia, ataxia, and hemochromatosis. It is contemplated that the use of the protein Liyor-1 will be by administering to a suitable patient an amount of this liver protein effective to treat the specific condition of that patient, and this would be carried out using conventional means and regimens well known to one skilled in this art. The sequence of Liyor-1 which has been determined using the cDNA libraries of the present invention is shown in FIG. 1A and 1B (SEQ ID NOS:1 and 2), and suitable amounts of the liyor-1 (145) protein may be prepared in a conventional manner by expressing by recombinant or other means the nucleic acid coding for the 145 protein, after which the protein can be isolated and/or prepared into substantially pure form as needed. In addition, the 145 protein may be administered with any other suitable compound normally utilized for administration into a patient, such as a suitable pharmaceutically acceptable carrier.

As indicated hereinbelow in the examples, other genes for early developing liver proteins in accordance with the present invention have been isolated and sequenced, including the genes coding for the elf proteins, praja-1, pk protein, protein 106, and genes 20, 36, 41, 112, 114, 118 and 129. With regard to the elf proteins, these proteins were studied by analyzing mRNA from tissues from mid-gestation embryos. Tissues were dissected from day 11 onwards, as it was at this stage that discrete hepatic, cardiac and other tissues could be dissected with ease, and the subsequent RNA that was isolated was of good quality. RNA hybridization with elf DNA in different mouse tissues was studied by using polyA RNA obtained at various developmental stages using a $^{32}$P-labeled 1.1 Kb insert representing elf. The specificity of the developmental changes in the steady state levels of elf was evaluated by also measuring the relative levels of Actin. This revealed a 2.4 Kb transcript at high stringency washes. Scanning densitometry of the respective bands revealed that maximal expression of elf occurred in liver and heart, less so in other tissues, but specifically on day 11, and in e12.5 and e14.5 in decreasing abundance (when Northerns were developed 1–2 months later).

In situ hybridization was then used to confirm elf expression in 11.5 heart and liver as well as to determine its expression pattern during earlier liver development, as will be set forth below in the Examples. The liver bud, which originates from foregut endodermal cells, grows into the septum transversum at the 9th day of gestation (13–20 somite stage). Between days 10.5 to 11.0 post coitus, a considerable degree of differentiation occurs: The liver enlarges substantially over this period, this increase in volume being due to the invasion of the mesenchyme of the septum transversum by the hepatic cords, and the initiation of hematopoietic activity in the liver. At day 9.5, a strong labeling of elf becomes apparent in the heart, and the pattern appears to be trabecular, including the wall of the cardiac anlage. A section of the sino-atrial chamber wall also shows a high intensity of elf expression. The surrounding tissue, particularly the caudal liver bud region does not show the presence of silver grains.

At the next stage, day 10.5, silver grains clearly highlight the developing liver, which appears as a horizontal structure (L) in this section. At this stage, the signalling is weakening in the developing heart tissue. The surrounding tissues are remarkable for the absence of silver grains. At day 11.5, a strong labeling of elf becomes apparent in the liver, which is larger in size. The heart at this stage only shows a weak signal posteriorly. As a control, in addition to sense probes, a riboprobe to alpha fetoprotein outlines the developing embryonic liver at days 11–12.

A comparison of the day 9.5 and 10.5 embryos, demonstrates a temporal and spatial expression of elf: the temporal gradient of a rise and fall of elf expression in the heart can be inferred from the strong staining in the developing heart at day 9.5 followed by a weaker staining at the next stage (day 10.5). Simultaneously, liver expression increases. The spatial gradient is apparent where silver grains increase in density on moving from the developing heart to the liver: at day 10.5, antisense RNA probes from elf cDNA hybridized specifically to day 9.5 cardiac mesenchymal tissue; expression at day 10.5 being restricted to cardiac and hepatic tissue, with elf expression finally being restricted to the liver in later 11.5 day embryos. Of note, elf expression was seen in embryonic livers at later stages (days 12.5, 14.5 p.c.), but only in decreasing abundance: the message being detected in these later stages when Northerns and in situs were developed a considerable time later. Sense probes to elf did not hybridize to any tissues. This indicates that ELF expression is not a sudden "on" "off" phenomenon, but more of a gradient pattern: consistent with the expression pattern of brain beta spectrin.

Alpha fetoprotein antisense RNA probes hybridized specifically to 11.5, 12.5, 14.5 embryonic mouse liver tissue, which is in agreement with previous studies of mRNA isolated from embryonic liver samples. The earliest stage that we were able to detect alpha-fetoprotein mRNA by in situ hybridization was at 10.5–11.0 days of gestation. Similar experiments with albumin mRNA have shown it to be expressed at day 9.5 in clusters of cells arising from foregut epithelium and in cords of cells seen to be invading the septum transversum. In experiments with alpha-fetoprotein, the liver was labeled at all subsequent stages (day 11 onwards), and, upon histological examination appeared to occur primarily in the endothelial cells. Hematopoietic cells appeared retractile but did not contain the hybridization grains that were visible over the alpha-fetoprotein positive cells. These experiments show that elf mRNA is localized to early embryonic heart, and then moving to e11 liver.

Next, it was determined that elf was a marker for the mesodermal component of liver formation. As Northern analysis had revealed elf expression to occur in day 11.5 heart and liver tissue, in situ localization was performed to investigate whether elf expression was restricted specifically to mesodermal tissue from the heart and the liver and was then compared to the endothelial expression of alpha fetoprotein. The main regions of mesoderm in the developing embryo are dorsal (somitic), intermediate, and lateral. Specifically, lateral plate mesoderm comprises somatic tissues (pleura, pericardium, peritoneum and limb bud), and splanchnic tissues (heart, epicardium, myocardium, connective tissue and smooth muscles of viscera and blood vessels, hemangioblastic tissue, adrenal cortex and spleen). The developing heart, at day 9 (13–20 somites), appears to be only region within the embryo where the endothelial elements of the circulation are surrounded by a vessel wall. The walls of the common ventricular and atrial chambers show an increasing degree of trabeculation. The space between the endothelial and myocardial elements is filled with loose mesenchyme called cardiac jelly. In situ hybridization of days 9 and 10 embryonic heart tissue using elf antisense riboprobes showed high levels of labeling to both the atrial and ventricular regions, highlighting the trabeculation.

Hepatic mesenchyme also originates from lateral plate mesoderm. The septum transversum part of the hepatic mesenchyme originates from the splanchnic mesoderm of the precardiac area and this is considered to be responsible for the subsequent differentiation of hepatocytes. However, tissue explant experiments have demonstrated that all derivatives of the lateral plate can replace hepatic mesenchyme for these later events. The initial experiments have shown that migrating endoderm must interact with mesenchyme for the former to differentiate into hepatocytes and recent studies investigating albumin mRNA expression, an indicator of hepatocyte differentiation, have confirmed these features; Initial expression of albumin mRNA occurs during the invasion of the septum transversum, when foregut endodermal cells clearly contact cardiac mesenchymal tissue. Similarly, primer extension analysis of albumin transcription has shown that the start site of transcription to occur at day 10.5 with a 15–20 fold increase in albumin mRNA upon liver organ formation by day 12.5. In our experiments using alpha fetoprotein as a marker for differentiated hepatocytes, it was obvious that while alpha fetoprotein expression is restricted to the later endodermal component of liver development, elf expression seems to occur in the loosely organized, lighter staining mesenchymal cells, initially cardiac mesenchyme (at day 9.5), then in both cardiac and hepatic tissue (at day 10.5) and then restricted to liver tissue (day 11.5 onwards); elf expression then decreases in abundance upon full embryonic liver formation. Examination of later histological sections (days 11 onwards) demonstrated a diffuse distribution of grains, and the hybridization signal with elf appeared to be localized in the perisinusoidal cells, but not in the hepatocytes.

That elf is expressed in early cardiac mesoderm, with subsequent expression being limited to hepatic mesoderm, indicates that this is a novel marker for the mesodermal component of liver development. Molecular markers have been invaluable in the dissection of inductive events in embryological studies. For instance, in Xenopus, vg-1, a member of the TGF-Beta family, now considered to be the strongest candidate for dorsal mesoderm induction, was in fact originally isolated by differential screening of mRNAs localized in the vegetal hemisphere of developing Xenopus eggs. Activins and other genes belonging to the TGF-Beta family such as vg-1, as well as wnt and BFGF families, represent components of the cascade leading to the commitment to particular mesodermal fate and all are strong candidates as mesoderm-inducing factors. Yet of these, only vg-1 has been demonstrated to be localized to the vegetal cells, the blastomeres responsible for mesoderm induction in vivo. Specific localization of vg-1 was vital and responsible for the persistence required in investigating its role as the inductive agent in mesoderm formation. Similarly, in isolating putative inductive agents required for liver formation, a key step is the localization of a new mRNA isolated from the embryonic livers. Accordingly, it is contemplated that elf and its associated regulatory genes will be of enormous potential benefit as a liver growth factor.

Further characterization of elf has involved RNA analysis of adult mouse and human tissues, and it was determined that elf hybridizes to adult liver, kidney and testis as a 2.4 Kb transcript in liver and kidney and a 2.6 Kb transcript in adult testis, in very low abundance: both blots were developed after being exposed to film for over a month at −70° C. Genomic DNA analysis of elf expression in DNA (genomic) from human, monkey, rat, mouse, dog, cow, rabbit, chicken and yeast indicates that elf is conserved across the species, being represented in all except rabbit DNA.

In vitro transcription and translation of elf, the latter using nuclease-treated rabbit reticulocyte lysate (promega) has revealed a 34 Kd protein, which is as predicted by the elf insert size and indicating that this insert is in frame for the coding sequence for a specific protein. These studies have established the principle that specific mesodermal mRNAs are localized in a way that guarantees their subsequent segregation to specific mesodermal tissue, in this case the presumed mesodermal component of the liver as shown by embryonic explant studies.

Figure 2A:
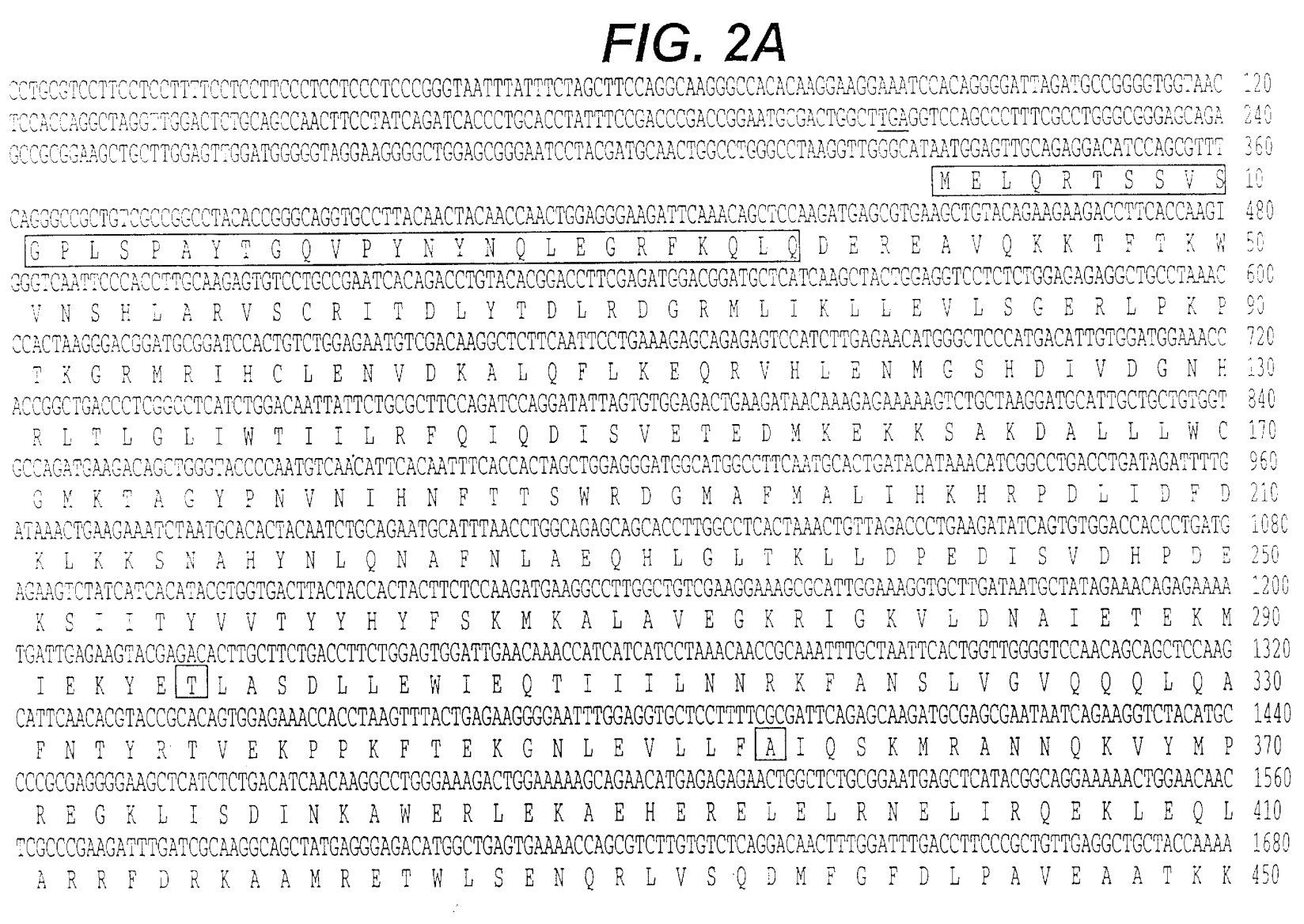
Figure 2B:
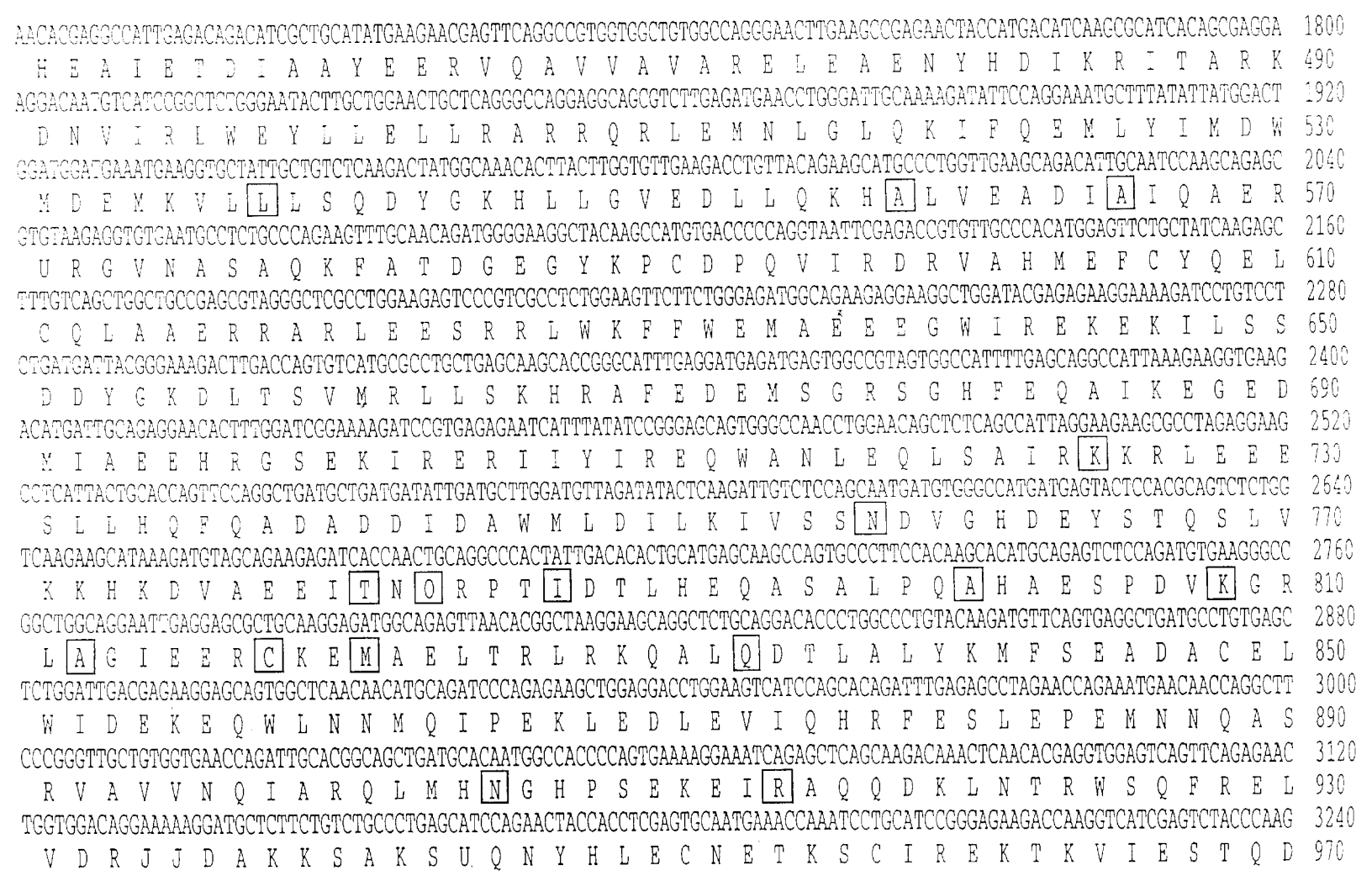
Figure 2D:
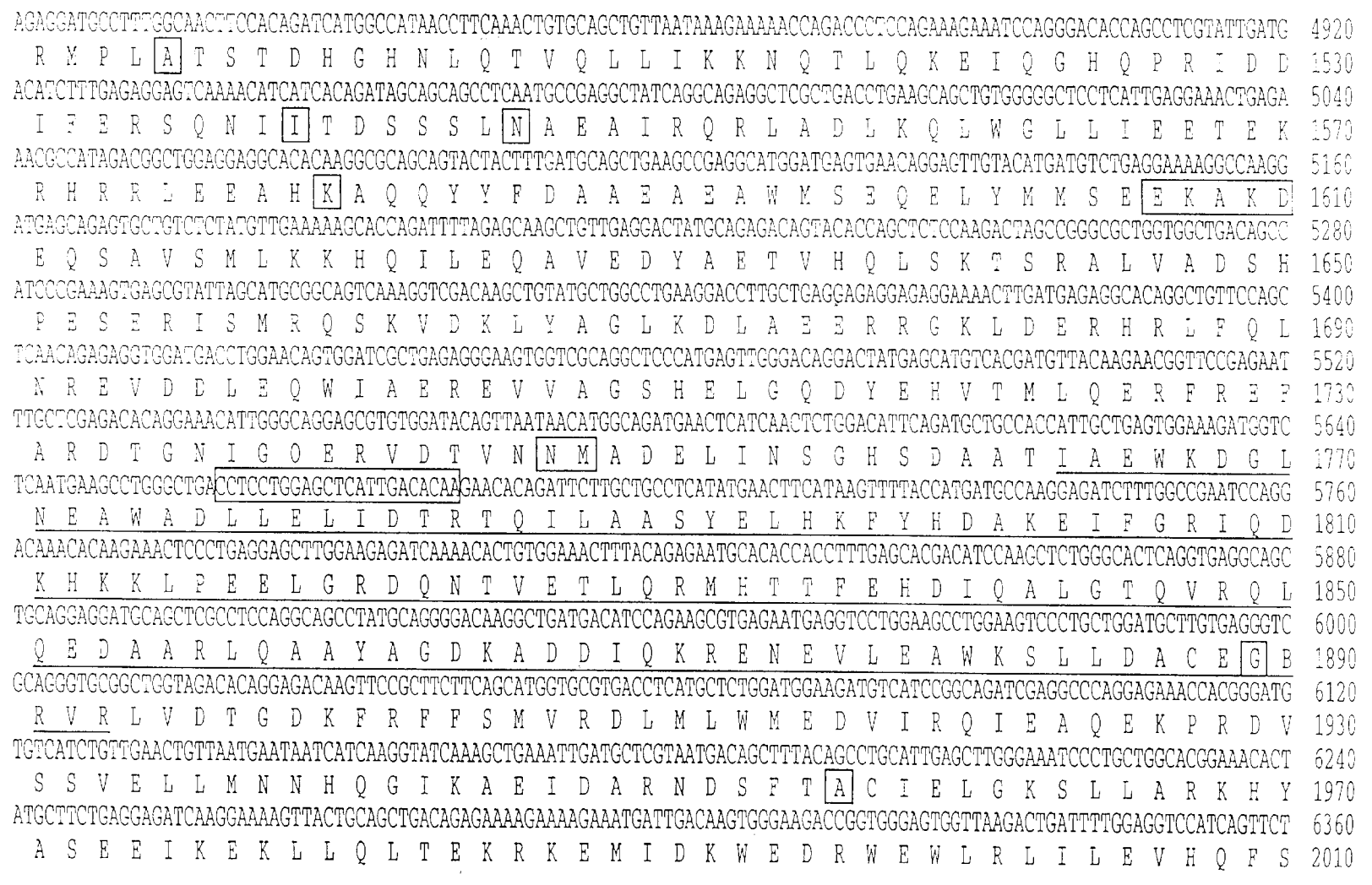
Figure 2E:
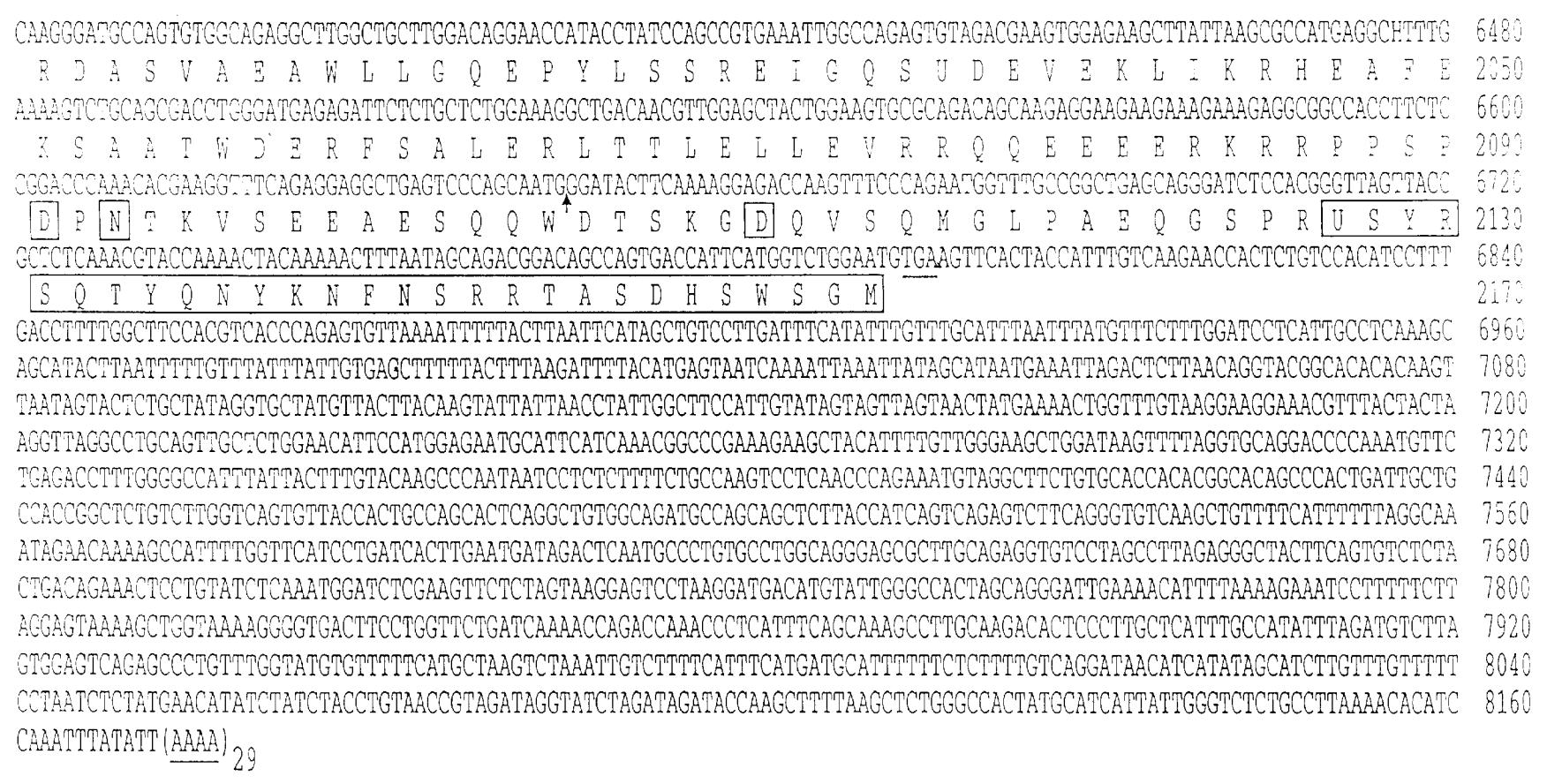
Figure 2J:
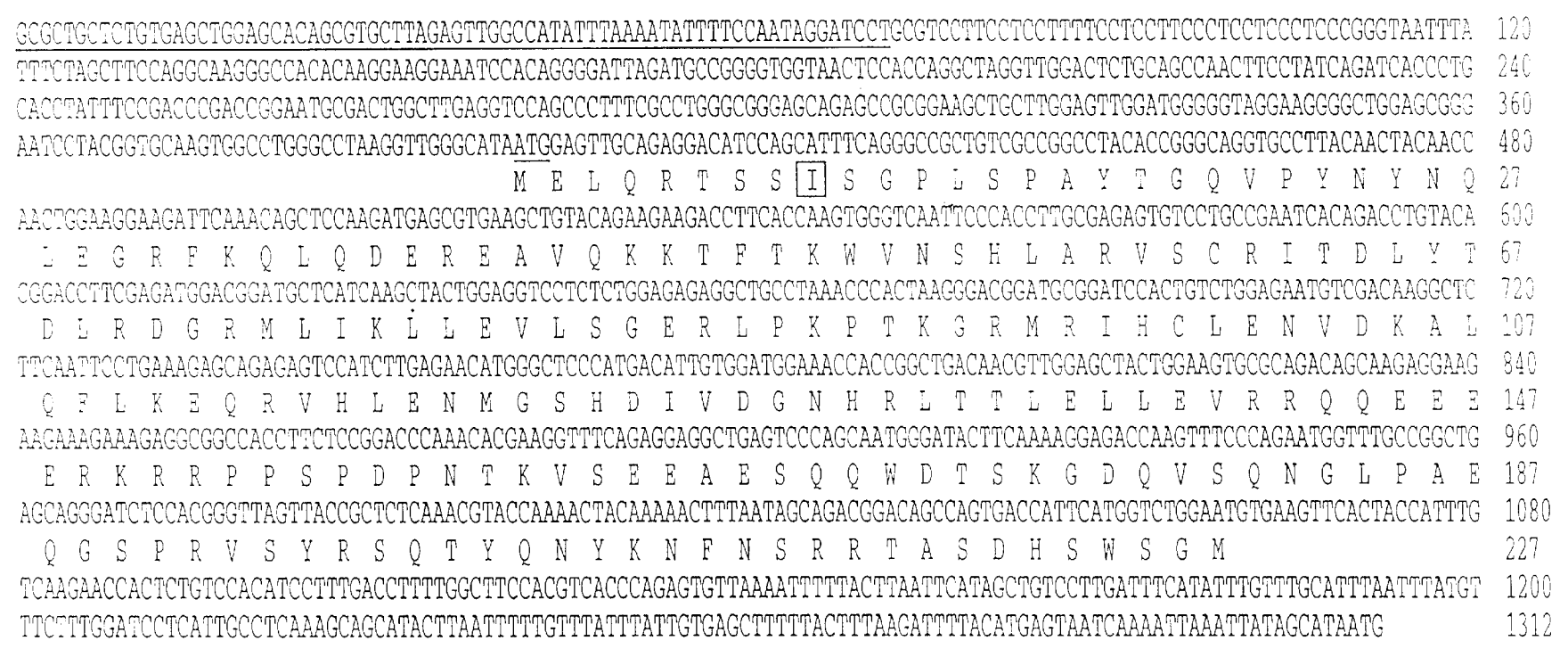

The elf protein has been sequenced, and it has been determined that at least three specific elf protein genes can be identified during early liver development. The sequences for these genes, known as elf-1, elf-2, and elf-3, are shown in the FIGS. 2A–2E (SEQ ID NOS:3 and 4), 2F–2I (SEQ ID NO:5) and 2J (SEQ ID NOS:6 and 7), respectively. As indicated above, it appears that the elf proteins 1–3 are probably important for the formation of the biliary tree during early liver development. Accordingly, it is contemplated that in accordance with the present invention, the elf proteins will be useful in treating various disorders associated with liver function, including cholestasis, biliary stones, obstruction, stricture, primary biliary cirrhosis, and primary sclerosing cholangitis. As would be readily apparent to one skilled in the art, methods of treatment using the elf proteins would comprise administration of an amount of an isolated elf protein that is effective to treat the specific disease condition described above. As also would be apparent, the elf proteins themselves can be prepared in a number of suitable ways by expression from the nucleic acid sequences indicated at FIGS. 2A–2J, including recombinant methods of producing these proteins, followed by separation, isolation and/or substantially purifying the elf proteins. The elf proteins once obtained in this manner can be put into any suitable form that is acceptable for use with patients. In addition, any of these three elf proteins may be administered with any other suitable compound normally utilized for administration into a patient, such as a suitable pharmaceutically acceptable carrier.

Another protein that has been identified and isolated in accordance with the present invention and which is contemplated to be used in a variety of therapeutic methods is known as praja-1. Praja-1 has now been studied in conjunction with the examination of early developing liver proteins, and an analysis of the amino acid translation revealed the presence of a COOH-terminal RING-H2 motif, which is a zinc finger variant. Additionally, Northern blot analysis of RNA from adult mouse showed expression of 3.1, 2.6, and 2.1 kb transcripts in liver, brain, and kidney, and an additional 2.3 kb transcript in testis. Expression of praja-I is also apparent in a colon cancer cell line, SW 480, and as set forth below, it is also contemplated that the praja-1 protein will be a useful marker in early detection of colon cancer.

It has also been learned that praja-1 maps to chromosome X, at about the 36 cM position. Other genes mapping to this general region include moesin (Msn), androgen receptor (Ar), interleukin-2 receptor gamma (IL-2rg), X-linked zinc finger protein (Zfx), and tabby (Ta). The syntony and conserved gene order between mouse and human X chromosomes allows comparison with human disease genes in the region. Human diseases in this region with mesodermal involvement include anhidrotic ectoderm dysplasia (eda) and sideroblastic anemia with spinocerebellar ataxia (asat), and it is thus contemplated that in accordance with the present invention, praja-1 will be useful in treating these disease conditions, as well as degenerative neurological disorders.

In vitro expression of praja-1 has shown that the translational product, which ran as two closely spaced bands of Mr=55.6 and 56.9 kD, is larger than the predicted ORF size of 47.4 kD. One possible explanation is that the expression product is very acidic, and acidic proteins such as granins are known to give anomalously high Mr on SDS-PAGE. The presence of two products suggests translation initiation at a second, internal ATG codon, such as at Met-19.

In addition, antisense studies to praja-I demonstrated that praja-I is essential for liver architecture formation. Preliminary antisense studies were performed at 1.25, 2.5 and 5 mfn concentrations, utilizing two different ODNs to praja-1. In these tests, liver and block explants were treated with these antisense ODNs compared with control (scrambled, sense or no ODNS). The results showed that control livers were generally larger than the antisense-treated livers, and control blocks showed early hepatocyte growth, cartilage growth, and very preserved bile ducts. Both livers and blocks treated with either antisense ODN to praja-1, showed minimal hepatocyte growth, cell necrosis, yet preservation of cartilaginous tissue, in a dose dependent manner.

In praja-1, aside from the RING-H2 finger, the stretch of thirty-four COOH-terminal amino acids just past this motif is especially rich in proline residues (17.6%); and, as stated, the protein in general is very acidic. Proline-rich domains are found in several mammalian transcription factors, such as that at the COOH-terminus of transcription factor CTF. Proline-rich regions and also acidic regions are likely to function in contacting other proteins. When considering the praja-I sequence as a whole, the rat Neurodapl gene has the highest similarity. Neurodapl is expressed abundantly in rat brain, with much smaller amounts in heart and skeletal muscle. Though praja-I likewise shows expression in brain, unlike Neurodapl (which is a larger 4.8 Kb transcript), it also expresses in liver and kidney. The subcellular localization of Neurodapl was shown to be concentrated around the endoplasmic reticulum (ER) and golgi of the cerebral cortex and facial nucleus, and especially in the postsynaptic density region of axosomatic synapses. Based on its subcellular localization, plus the presence of the RING-H2 finger, Neurodap I is probably linked to the secretory or protein sorting. This similarity to Neurodapl indicates that praja-I is most likely involved in protein-protein interactions, possibly in a protein sorting or secretary pathway involved during hepatocyte formation.

The gene coding the praja-l protein has been sequenced, and this nucleic acid sequence is depicted in FIGS. 3A–3B (SEQ ID NOS:8 and 9). As indicated above, it appears that the praja-1 protein is probably important for iron transport, and essential for hepatocyte formation as well as hematopoiesis. Accordingly, in accordance with the present invention, praja-1 can be used in methods of diagnosing and treating diseases such as end stage liver disease, iron storage disorders, hepatocellular carcinoma, as well as anemia, such as sideroblastic anemia, ataxia, such as spinocerebellar ataxia, and hemochromatosis. As would be recognized by one skilled in the art, these methods of treatment would involve administering of an effective amount of the praja-1 protein to the patient afflicted with one of the disease conditions set forth above. In addition, the isolation of the praja-1 protein could be obtained by expression of the nucleic acid sequence indicated at FIGS. 3A–3B which codes for the praja-1 protein, and this protein can be produced from its nucleic acid sequence in any suitable manner well known in the art such as recombinant means. Once isolated in this manner, the praja-1 protein can be obtained in a desired form, such as in substantially purified condition, and can be incorporated into any suitable mode of treatment that would be compatible with the patient in need of such treatment. In addition, the praja-1 protein may be administered with any other suitable compound normally utilized for administration into a patient, such as a suitable pharmaceutically acceptable carrier.

Even further, as indicated above, it has also been discovered that the protein praja-1 has been identified in cancerous colon tissue, such as in colon cancer cell line SW 480, which normally does not produce this protein. Accordingly, it is contemplated that in accordance with the present invention, a method of detecting and diagnosing colon cancer is provided wherein colon cells or tissues are taken from a patient being tested, and these cells or tissues are screened in any suitable manner which would identify the presence or absence of the praja-1 protein in the tested cells or tissues. In this manner, the identification of praja-1 in the colon cells or tissues from the patient will be indicative of a cancerous condition in the colon cells or tissues, and thus the present invention will provide a simple and effective method for determining at an early stage, when the disease is still in a treatable condition, if the patient appears to have contracted colon cancer. Conversely, the absence of praja-1 will generally be indicative of a non-cancerous state in the colon cells tested.

Still other genes coding for early developing liver proteins in accordance with the present invention have been identified and sequenced, and these proteins will also be useful in various methods of diagnosis and treatment of disease conditions associated with the liver or liver function. Included in these additional genes are those nucleic acids coding for a protein identified as pk, as depicted in FIGS. 4A–4B (SEQ ID NO:10), nucleic acids coding for a protein identified as protein 106, as shown in FIG. 5, and genes 20, 36, 41, 112, 114, 118 and 129, as shown in FIGS. 6–12. These proteins also appear to useful in hepatocyte formation and in treating liver diseases in a similar manner to many of the proteins discussed above, and in a manner similar to known growth factors should be useful in treating a variety of conditions. For example, protein pk appears to be important in Ito cell formation and fibrosis and thus appears to be useful in the same manner as protein liyor-1 (145). Accordingly, the protein pk, as prepared from the nucleic acid sequence indicated at FIGS. 4A–4B, will likely be useful in treating end-stage liver disease, hepatocellular carcinoma, as well as other disease conditions including anemia, ataxia, and hemochromatosis. As in the above cases, these early developing liver proteins may be administered with any other suitable compound normally used for administration to patients, such as suitable pharmaceutically acceptable carriers.

It is thus submitted that the foregoing embodiments are only illustrative of the claimed invention, and alternative embodiments well known or obvious to one skilled in the art not specifically set forth above also fall within the scope of the claims.

In addition, the following examples are presented as illustrative of the claimed invention, and are not deemed to be limiting of the scope of the invention, as defined by the claims appended hereto, in any manner.

EXAMPLE 1

In accordance with the cloning strategy of the present invention to identify genes involved in early mouse liver development, the gene Praja-1 has now been isolated, a gene with similar sequences to the Drosophila melanogaster gene goliath (gl), and which is involved in the fate of mesodermal cells ultimately forming gut musculatures, fat body, and the heart. Praja-1 is a 2.1 kb gene encoding a putative 423 amino acid ORF and includes a COOH-terminal RING-H2 domain. Using the Jackson Laboratory BSS panel, the praja-1 gene was localized on chromosome X at 36 cM, near the X inactivation center gene, Xist. Northern blot analysis demonstrated three transcripts (3.1, 2.6 and 2.1 kb) in mRNA from adult mouse tissues brain, liver, and kidney as well as in mRNA from developing mouse embryos (days 7, 11, 15 and 17 post coitus, or p.c.). In vitro transcription/translation yielded two products with a Mr of 55.6 and 56.9 kD. The presence of the RING-H2 domain, a proline-rich region at the COOH-end, and regions rich in acidic amino acids, leads to the hypothesis that the Praja-1 product is involved in mediating protein-protein interactions, possibly as part of a protein sorting or transport pathway. This is strengthened by the similarity of praja-1 to rat Neurodap1, whose product has been shown to localize to the endoplasmic reticulum and golgi in brain.

The molecular mechanisms underlying hepatocyte differentiation are not well understood, and thus identifying the genes underlying the control of liver development will provide powerful tools for understanding liver function and development, and will allow the use of inducing liver differentiation for therapeutic purposes. As part of a strategy to clone such genes, a new RING-H2 finger gene, praja-1, was isolated. RING-H2 fingers, a type of zinc finger, are similar to RING fingers except that Cys4 is replaced by His (see Freemont, *Ann. N.Y. Acad. Sci.* 684:174–192 (1993); Lovering et al., *P.N.A.S.* 90:2112–2116 (1993)). Here it is shown that praja-1 possesses a RING-H2 motif near the COOH terminal. The RING-H2 motif is similar to that of the Drosophila melanogaster gl gene (Bouchard et al., *Gene* 125:205–209, 1993), and to the rat Neurodap1 gene (Nakayama et al., *J. Neurosci.* 15:5238–5248, 1995). Praja-1, which localizes to chromosome X, is expressed in mouse brain, liver, and kidney. The presence of the RING-H2 motif, plus the acidic, hydrophilic nature of the translation product, leads to the hypothesis that praja-1 plays a role in protein transport.

Materials and Methods cDNA preparation and 3'-RACE PCR: RNA was isolated from livers of day 11 p.c. embryonic mice (ICR, Harlan Sprague-Dawley) using guanidine thiocyanate (Chomczynski et al., *Ann. Biochem.* 162:156–159, 1987). Poly(A)+ mRNA was isolated from total RNA using Dynabeads, as per manufacturer's instructions. First strand cDNA was made from poly(A)+ mRNA using the Promega Reverse Transcriptase System and the 3'-RACE primer 5'- (Frohman, In: M. A. Innis et al. (eds.), *PCR protocols: a guide to methods and applications*, Academic Press, San Diego, pp. 28–38., 1990). The 3'-RACE primer was also used as the reverse primer in the PCR reaction. The forward PCR primer, originally designed to amplify a conserved region of a clone 145/PH (pleckstrin homology) domain, was 5'. The PCR reaction mix contained cDNA from about 10 ng of poly(A)+ mRNA, 25 pmol of each primer, I mM DNTP mix, and 2.5 units of AmpliTaq DNA polymerase (Perkin-Elmer) all in 10 mM Tris, 1.5 mM $MgCl_2$, and 75 mM KCl, pH 9.2 in a final volume of 50 ml. The temperature program comprised 35 cycles of denaturation (94° C., I min), annealing (55° C., 1 min), and extension (72° C., 3 min), followed by an additional 8 minute extension. One of the resulting PCR products (CH7) comprised a 725 bp fragment, which was cloned into vector PCRII using the Invitrogen TA Cloning Kit for sequencing, and found by sequence analysis to possess a RING-H2 finger. The portion of the final cDNA clones which correspond to CH7 is indicated in FIGS. 3A–3B.

Library screening: The PCR product CH7 was labeled with [a-32P]-dCTP (3000 Ci/mmol, Amersham) via primer extension using the reverse PCR primer plus AmpliTaq polymerase at 72° C. in PCR buffer (Konat et al., in *PCR Technology: Current Innovations* (H. G. Griffin and A. M. Griffin, Eds.), CRC Press, Boca Raton, pp. 37–42, 1994). The resulting antisense probe was used to screen plaque lifts of a whole embryonic mouse (day 11 p.c.) cDNA library in vector λZap (Stratagene). Positive plaques were picked and purified, and DNA was isolated from lysates using standard procedures (Silhavy et al., *Experiments with gene fusions*, Cold Spring Harbor Laboratory Press, Cold Spring Harbor, New York, 1984). Inserts were excised from λZap DNA using EcoRI, and were subcloned into pGEM3Zf(-) (Promega) for sequencing and subsequent manipulations.

DNA sequence analysis: DNA sequence comparisons to existing sequences were performed utilizing BLAST searches in Genbank. Alignments were performed using the GCG program PILEUP.

Chromosomal mapping: Southern blot analysis of genomic DNA from C57BL/6J (B6) and Mus spretus (SPRET/Ei) using [32P]-labeled CH7 as a probe revealed a restriction fragment length polymorphism for the enzyme TaqI. This polymorphism was used to follow the inheritance of the praja-1 gene using the (B6×SPRET/Ei)×SPRET/Ei backcross panels (BSS) from The Jackson Laboratory Backcross DNA Panel Map Service (Rowe et al., *Mammalian Genome* 5:253–274, 1994). Linkage and order relative to other markers was determined by minimizing the number of multiple recombinants within each haplotype.

Northern blot analysis of Praia-l expression: Northern blots containing 2 micrograms of poly(A)+ mRNA from mouse tissues (Clontech) were probed with [32P]labeled CH7 antisense strand using Express Hyb hybridization solution (Clontech) at 68° C., washed according to manufacturer's instructions, and subjected to autoradiography. A [32P]-labeled b-actin probe supplied with the Northern blots was used as a control to normalize RNA levels in each lane.

In vitro transcription/translation:

A transcription/translation-coupled rabbit reticulocyte lysate system (Promega) was used, as per manufacturer's instructions for [35S]methionine labeling. Clones of praja-1 in pGEM3Zf(−) plus a luciferase control clone were used with T7-RNA polymerase (sense direction). Each reaction comprised 12.5 ml rabbit reticulocyte lysate, 1 ml reaction buffer, 0.5 ml 1 mM amino acid mix minus methionine, 0.5 ml T7-RNA polymerase, and 20 units RNasin, all in 25 ml final volume. After a 90 min incubation at 300° C., products were lysed in SDS/mercaptoethanol treatment buffer and separated on a 10% SDS-polyacrylamide gel according to Laemmli, *Nature* 227:680–685 (1970). Proteins were electroblotted onto a BAS-NC membrane (Schleicher & Schuell) using a BioRad Trans-Blot apparatus according to manufacturer's instructions. Labeled products were visualized by autoradiography.

Results:

Isolation and sequence analysis of the novel gene. praja-1:

As part of the analysis of genes involved in liver development and function, we amplified the 3' end of a previously undescribed gene, CH7. We used the CH7 probe to screen a mouse embryonic cDNA library and isolated two overlapping clones, praja-1-5 and praja-1-6. Sequence analysis of the consensus overlap region revealed an open reading frame (ORF) of 424 amino acids, with a predicted size of 47.4 kD. Hydropathy analysis (Kyte et al. *J. Mol. Biol.* 157:105–132, 1982; not shown) shows that the translation product is highly hydrophilic, with no hydrophobic leader or membrane-spanning regions. The translation is also very acidic, with a pI of 4.6 and containing 17.7% acidic residues (Asp plus Glu). The putative ATG start codon indicated in FIGS. 3A–3B was selected because it is the upstream-most ATG that is in-frame with the ORF, and is preceded 21 bp upstream by a TAG stop codon. The context of this ATG, however, is only a weak fit to the consensus Kozak recognition sequence GCCACCatgG in that it does not have a purine at −3 nor a G at +4 (reviewed by Kozak, *Genome* 7:563–574, 1996). Sequence analysis of the amino acid translation revealed the presence of a COOH-terminal RING-H2 motif, which is a zinc finger variant (Freemont, supra). those of several other RING-H2 containing proteins.

Linkage analysis places Praia-l on mouse chromosome X:

A restriction fragment length polymorphism for praja-1 was identified using CH7 as a probe on a Southern blot containing DNA from the two parental strains digested with several restriction enzymes (TaqI, BglII, EcoRI, EcoRV, HindIII, HincII, KpnI, PstI). For every enzyme used, C57B16/J had only a single restriction fragment, while two fragments were always observed within the SPRET/Ei lane. A polymorphism obtained using TaqI was used to type the inheritance of the C57B1/6J allele in the BSS panel. There are two Spretus bands S1 and S2 and one C57B1/6J band B1. After comparison of the praja-1 genotypes to other genes typed within the database, it was determined that praja-1 maps to mouse chromosome X at about the 36 cM position. The S1 band is the praja-1 allele on X chromosome of SPRET/Ei. The S2 TaqI fragment appears in every backcross animal. Since all males from the backcross contain this allele, it is not localized to the X chromosome. Since females also have the S2 band, it is not Y-linked. Therefore S2 is an autosomal locus that contains sequence homology to the praja-1 probe sequence. Other genes mapping to this general region include moesin (Msn), androgen receptor (Ar), interleukin-2 receptor gamma (Il2rg), X-linked zinc finger protein (Zfx), and tabby (Ta). This area is also 1.1 +/− 1.1 cM from the Xist locus. Further studies are needed to determine if praja-1 is not expressed on inactivated X-chromosomes and if it plays a role in X-inactivation. The syntony and conserved gene order between mouse and human X chromosomes (Herman et al., *Genome* 6:S317–S330, 1996) allows comparison with human disease genes in the region. Human diseases in this region with mesodermal involvement include anhidrotic ectoderm dysplasia (eda) and sideroblastic anemia with spinocerebellar ataxia (asat).

In vitro expression produces a protein product larger than the predicted size. An autoradiogram of the in vitro transcription/translation products of clones praja-1-5 and praja-1-6 showed that only praja-1-5 produced a significant product. The product, which ran as two closely spaced bands of Mr=55.6 and 56.9 kD, is larger than the predicted ORF size of 47.4 kD. One possible explanation is that the expression product is very acidic, and acidic proteins such as granins are known to give anomalously high Mr on SDS-PAGE (Huttner et al., *Trends Biol. Sci.* 16:27–30, 1991). The presence of two products suggests translation initiation at a second, internal ATG codon, such as at Met-19.

Praja-1 transcripts are present in embryonic and in mouse tissues. Northern blot analysis of RNA from adult mouse showed expression of 3.1, 2.6, and 2.1 kb transcripts in liver, brain, and kidney, and an additional 2.3 kb transcript in testis. The praja-1 protein is unlikely to be a membrane receptor, since it lacks a hydrophobic transmembrane domain. The uniform hydrophilicity suggests a soluble protein. The praja-1 RING-H2 motif is shown aligned with those from several other proteins. RING fingers are generally thought to function in protein-protein interactions (Borden et al., *Curr. Opinion Struct. Biol.* 6:395–401, 1996; Saurin et al., *Trends Biochem. Sci.* 96:208–214, 1996). To cite a specific example, if either of the two cysteines that comprise the Zn++ binding site of the RING finger of acute promyelocytic leukemia protooncoprotein PML are mutagenized, then the nuclear multiprotein complex, or so-called nuclear bodies, fail to occur (Borden et al., *EMBO J.* 14:1532–1541, 1995). The authors conclude that the PNM RING domain, and probably other RING finger domains, are involved in protein-protein interactions.

In praja-1, aside from the RING-H2 finger, the stretch of thirty-four COOH-terminal amino acids just past this motif is especially rich in proline residues (17.6%); and, as stated, the protein in general is very acidic. Proline-rich domains are found in several mammalian transcription factors, such as that at the COOH-terminus of transcription factor CTF, and proline-rich regions and also acidic regions are likely to function in contacting other proteins (Mitchell et al., *Science* 245:371–378, 1989). A BLAST search of the proline-rich COOH-terminus revealed no significant matches to any protein in the available databases, however, when considering the praja-1 sequence as a whole, the rat Neurodap1 gene has the highest similarity; the alignment is presented in FIG. 15.

Neurodap1 is expressed abundantly in rat brain, with much smaller amounts in heart and skeletal muscle. Though praja-1 likewise shows greatest expression in brain, unlike Neurodap1 it also expresses in liver and kidney. The subcellular localization of Neurodap1 was shown to be concentrated around the endoplasmic reticulum (ER) and golgi of the cerebral cortex and facial nucleus, and especially in the postsynaptic density region of axosomatic synapses (Nakayama et al., supra). Based on its subcellular localization, plus the presence of the RING-H2 finger, the authors concluded that Neurodap1 is probably linked to the secretory or protein sorting. Praja-1 does differ from Neurodapl in several respects, however. In addition to being expressed in some different tissues than Neurodap1, praja-1 encodes for a product that is smaller (47.4 kD, based on the composite of the clones in vs. 77.9 kD for Neurodap1. The difference in size is at the N-terminus of the proteins. The largest transcript we observed for praja-1 was 3.1 kb, whereas Neurodapl exists as a single 4.8 kb transcript on Northern blots of rat brain mRNA.

In light of the fact that BRCA1, which possesses a RING finger, has an acidic pI, and is a secretory protein, also has properties of the granin family of proteins (Jensen et al., *Nature Genet.* 12:303–308, 1996), we examined praja-1 for a granin signature. We found no region in the praja-1 translation that gave a perfect match to the consensus E[N/S]LX[A/D]X[D/E]XEL, though two regions matched five of the seven conserved residues. We were also unable to demonstrate the presence of clear coiled-coils, which are present in BRCA1 and proteins with the previously-mentioned tripartite structures. In these respects, praja-1 is more similar to Neurodap1 than to proteins such as BRCA1. Also, though the RING-H2 finger in praja-1 shows much similarity to that from the D. melanogaster goliath (gl) protein, the goliath protein possesses an alkaline pI (8.9) and no sequence similarity to praja-1 outside of the RING-H2 finger. The RING-H2 motif plus acidic and proline-rich regions, and similarity to Neurodap1, leads to the conclusion that praja-1 is involved in protein-protein interactions, possibly in a protein sorting or secretory pathway.

EXAMPLE 2

In accordance with the present invention, investigations were made with regard to the induction of differentiation in liver tissues in order to isolate and identify early developing liver proteins for use in therapies involving the liver and liver functions. In the developing fetus, inductive interactions, intercellular communication and the establishment of cell polarity are critical for growth and patterning during development. However, the precise mechanisms by which these effect hepatocyte differentiation or liver development have not previously been elucidated. Mammalian liver development was first recognized to be established through a specific sequence of interactions between mesenchymal and endodermal embryonic tissues. At 9.5 days of mouse gestation, upon signaling from the cardiac mesenchyme, endodermal cells from the liver diverticulum proliferate and migrate into the surrounding septum transversum. This specific area of loose mesenchyme in turn differentiates into hepatic mesenchyme and a liver bud is finally recognizable microscopically at about 10.5 days of gestation. This hepatic mesenchyme is continually responsible for the hepatocyte proliferation which then proceeds throughout embryonic life (Le Douarin, *Med. Biol.* 53:427–455, 1975). Albumin transcription can be detected as early as at day 9.5 (Cascio et al., *Development* 113:217–225, 1991), implying that hepatocyte differentiation begins when hepatic endoderm comes into contact with cardiac mesoderm. As a first step towards the analyses of signal transduction pathways regulating such a restricted pattern of gene expression, molecular markers as well as regulatory genes are required to identify the interactions required for liver development.

The dissection of gene regulatory pathways in the liver has led to the identification and characterization of transcriptional activators, C/EBP, DBP, LFB 1/HNF 1, 3 and 4 (Johnson, *Cell Growth Differ.* 1:47–52, 1990; Kuo et al., *Development* 109:473–481, 1990; Frain et al., *Cell* 59:145–157, 1989), of liver specific genes, such as α-fetoprotein and albumin (Tilghman, *Oxford Surveys on Eukaryotic Genes*, Oxford University Press, 1985). Yet, with the exception of HNF4, 3 α and β (Ang et al. *Development* 119:1301–1315 (1991) and *Cell* 78:561–574, 1994), none of the above have been found to play a definitive role in determining cell-lineage and regional specification of the developing liver. The small volume of liver buds (approximately $4 \times 10^{-2}$ mm$^3$) yields even smaller quantities of proteins, DNA and messenger RNA thus making the molecular analysis of liver development difficult. Therefore, the construction of early embryonic liver cDNA libraries, and performing subtractive hybridization still remains the most plausible and comprehensive method of obtaining an unbiased catalogue of genes required during early mouse liver development (see Harrison et al, *Development* 121:2479–2489, 1995).

The isolation of markers would provide further insight into identifying transcriptional activators and growth factors involved in such a restricted pattern of gene expression, and eventually provide an approach to identifying signal transduction pathways involved in hepatocyte differentiation. In some cases, these pathways have been characters as in patterning and axis formation of the vertebrate head and body (Oliver et al., *Development* 121:693–705 (1995); Kessel et al., *Science* 249:374–379, 1990). For example, in Xenopus, a network involving brachvury, activin and wnt-related genes, is responsible for mesoderm induction, somitogenesis, myogenic and sclerotomal differentiation (see, e.g., Wilkinson et al., *Nature* 343:657–659 (1990); Herrmann et al., *Development* 113:913–917 (1991); Green et al., *Trends Genet.* 7:245–250 (1991); Sokol et al., *Cell* 67:741–752 (1991) ; and Smith et al., *Cell* 67:753–767, 1991), and dorsal ventral axis formation results from Xgsk-3 (the Xenopus homologue of Drosophila zw3/shaggy) phosphorylating its Xenopus homologue of armadillo, β catenin thus regulating the level of β catenin available for dorsal axis formation. However, there are no available molecular markers nor pathways which characterize either earlier liver development, nor its crucial mesodermal component.

In accordance with the present invention, it has been possible to identify and characterize such molecular markers and possible inductive transcripts for liver development. As set forth below, the characterization of the elf protein is described, and the expression of this protein may mark the separate components of liver development. The "bottom up" approach with regard to this characterization in general has led to the identification of a totally unexpected group of genes, and in particular, this is described with regard to the elf protein, which is probably involved in playing a role in establishing cell polarity by interactions at the surface membrane.

Characterization of cDNA libraries:

The four stages in liver development (e10, e11, e12, and e14, where e=embryonic) are defined developmental time points from undifferentiated mesodermal/endodermal cells to a well developed and differentiated fetal liver. A change in cell polarity occurs at e9–10. At e10.5–11, invasion and migration of endodermal cells into surrounding mesenchyme occurs; at e11.5–12, pseudolobule formation, cords of hepatocytes form together with early sinusoids. cDNA libraries representing these stages would therefore, represent "captured" mRNA species expressed in greater abundance during crucial time periods for hepatocyte formation, enabling their isolation and providing a method for analyzing the changing pattern of gene expression during liver development.

Libraries containing $5.0 \times 10^6$–$4.1 \times 10^7$ independent clones were generated from the largest cDNA fractions. Current estimates demonstrate that a library containing $5.0 \times 10^5$ clones (Sambrook et al, *Molecular cloning, a laboratory manual*, Cold Spring Harbor Laboratory Press, Cold Spring Harbor, 1989) is a representative library with a 99% probability that rare transcripts (less than ten copies per cell) are present. Our libraries are therefore likely to be truly representative of their respective mRNA species for that stage.

Qualitative and developmental profiles of the libraries:

These were obtained, utilizing genes, such as IGF-II, IGFBP-2, IGF1, C/EBP, HNF/LFBI known to be expressed at different time points in developing liver. The data in Table 2 below demonstrate that IGF-I was not detected in any of the embryonic libraries, while IGF-H was detected in the e10.0 and e12.5 libraries (3 at e10.0 and 4 at e 12.5). IGF-II was not detected in the adult liver library. Interestingly, BP-2 clone frequencies are similar to IGF-II in the early e6.5, e7.5 and e8.5 libraries (data not shown), but in the liver cDNA libraries the clone frequencies differed, for BP-2 only one clone per 100,000 being detected at el0.0 and ell.5, while 7 were detected in the adult liver cDNA library compared to the greater numbers for IGF-II. This implied that its temporal and spatial expression in the embryo and fetus is different from IGF-II and this was subsequently confirmed by in situ studies. HNF1/LFB I detected in the e12.5 library was suddenly detected at day 11.5 and 12.5 in low abundance (2 clones/100,000 at e11.5 and 5 at e12.5), confirming that while it is expressed, its level also may be regulated, albeit downward, in embryonic stages. Lastly, mouse β-Actin was used as a reference: all seven libraries had similar β-Actin frequencies from 120–300/100,000 clones which is considered representative of such embryonic libraries.

Identification of stage specific clones by subtractive methods:

Two subtracted libraries were then constructed as previously described, comprising 64 clones (e11.5–12.5), and 174 clones (e10.5–11.5). Further characterization of these clones was carried out by Southern hybridization, sequencing, Northern blot analysis, Zoo blot analysis, and in vitro fertilization of protein. Using Southern blotting, thirty-four clones were shown to be stage specific and not containing mitochondrial, ribosomal and globin sequences, and further analysis was carried out on elf.

Identification and developmental regulation of elf transcripts:

Elf mRNA in tissues from mid-gestational embryos were analyzed, and tissues were dissected from day 11 onwards since it was at this stage that discrete hepatic, cardiac and other tissues could be dissected with ease, and the subsequent RNA isolated was of good quality. Using a 32P-labeled 1.1 Kb insert representing elf, the specificity of the developmental changes in the steady state levels of elf was evaluated by also measuring the relative levels of β-Actin. This revealed a 2.1 Kb transcript at high stringency washes. Scanning densitometry of the respective bands revealed that maximal expression of elf occurred in liver and heart, less so in other tissues but specifically on day 11, and in 12.5, 14.5 in decreasing abundance (when Northerns were developed 1–2 months later).

Sequence analysis of elf:

After subtraction hybridization, one stage specific clone was analyzed in detail: sc32. The initial libraries were then screened at high stringency (0.2×SSC, 60°), to obtain overlapping clones for sc32. Positives were picked, and after in vivo excision (Stratagene) into Bluescript, these were sequenced using the dideoxy chain termination method using oligonucleotides corresponding to previously determined sequence. Of the seven clones picked, three were found to be overlapping to sc32 and included sequence encoding elf. Confirmation of the identity of the clones and elf was carried out by Northern blot analysis of mouse embryonic tissues. In the case of elf, this gave rise to the same initial 2.1 Kb transcript with sc32 as a probe. A start codon was not present suggesting that we had not cloned the 5' end of the cDNA. However, the northern blot showed a 2.1 Kb transcript, thus suggesting that we had cloned complete elf and this probably represented a spliced form of β-fodrin. The authenticity of the 3' end of the elf sequence was confirmed by the comparison of the elf sequence with the expressed sequence tags (EST) database. Although no mouse ESTs for elf sequence were found, three different human EST clones were found to span the region of unique last 100 nt and the 5' adjacent sequence, suggesting the existence of elf homolog in human cells.

Prior sequence analysis has shown elf to bear 80% identity to β-fodrin, a non erythroid β-spectrin. Our sequence to elf is located between domains II and III of the β-spectrins. Domain II comprises 17 repeats of a 106 amino-acid motif and an ankyrin binding domain. The ankyrin binding domain is required for the correct subcellular localization of adducin, ankyrin and the Na+,K+ ATPase, without which cell morphology is disrupted. Domain II comprises a C terminal domain which contains varying numbers of residues (52–265) in alternatively spliced forms giving rise to tissue specific expression (Hu et al., *J. Biol. Chem.* 267:18715–18722, 1992), as well as the PH domain.

In situ localization of elf:

In situ hybridization confirmed elf expression in 11.5 heart and liver and determined its expression pattern during earlier liver development, using elf sense probes and alpha fetoprotein antisense probes as controls. The hepatic diverticulum, which originates at the foregut-midgut junction, begins to grow into the septum transversum at the 9th day of gestation (13-20 somite stage). Between days 10.5 to 11.0 p.c., a considerable degree of differentiation is seen in this primitive liver. The liver enlarges substantially over this period: the increase in the overall volume being due to the invasion of the mesenchyme of the septum transversum by the hepatic cords, and the initiation of hematopoietic activity in this organ. At day 9.5, a strong labeling of elf becomes apparent in the cardiac silhouette: the pattern appears to be trabecular, including the wall of the cardiac anlage. A section of the cephalad chamber (sino-atrial chamber) wall also bears a high intensity of elf expression. The surrounding tissue, particularly the caudal liver bud region does not show the presence of silver grains. At the next stage, day 10.5, silver grains clearly highlight the developing liver, which appears as a horizontal oriented structure (L) in this section. At this stage, the signaling is weakening in the developing heart tissue. The surrounding tissues are remarkable for the absence of silver grains. At day 11.5, a strong labeling becomes apparent in the liver, which is larger in size. The heart shows an extremely weak signal: silver grains being visible in only a single streak posteriorly. At this stage, elf expression also appears in the umbilical cord. As a control, in addition to sense probes, a riboprobe to α-fetoprotein outlines the developing embryonic liver at day 11–12.

A comparison of the day 9.5 and 10.5 embryos demonstrates a clear temporal and spatial gradient of maximal tissue staining with silver grains representing elf riboprobe: the temporal gradient of a rise and fall of elf expression in the heart may be inferred from the strong staining in the developing heart at day 9.5 followed by a weaker staining at the next stage (day 10.5). Simultaneously, liver expression increases. The spatial gradient is apparent from the developed patterns of these tissues which showed that silver grains increase in density as one moves from the developing heart to the liver: at day 10.5, antisense RNA probes from elf cDNA hybridized specifically to 9.5 day cardiac mesenchymal tissue; expression at day 10.5 being restricted to cardiac and hepatic tissue; elf expression finally being restricted to the liver in later 11.5 day embryos. Of note, elf expression was seen in embryonic livers at later stages (days 12.5, 14.5 p.c.), but only in decreasing abundance: message being detected in these later stages when Northerns and in-situ were developed a considerable time later. Elf sense probes did not hybridize to any tissues.

Alpha fetoprotein antisense RNA probes hybridized specifically to 11.5, 12.5, 14.5 embryonic mouse liver tissue, in agreement with previous studies of mRNA isolated from embryonic liver samples (Tilghman et al., *P.N.A.S.* 79:5254–5257, 1982). The earliest stage of detection of α-fetoprotein mRNA by in situ hybridization was at 10.5–11.0 days of gestation. Similar experiments with albumin mRNA (Cascio et al., *Development* 113:217–225, 1991) have shown it to be expressed at 9.5d in clusters of cells arising from foregut epithelium and in cords of cells beginning to invade the septum transversum. In the experiments with α-fetoprotein, the liver was labeled at all subsequent stages (day 11 onwards), and, upon histological examination appeared to occur primarily in the endothelial cells. Hematopoietic cells appeared refractile but did not contain the hybridization grains that were visible over the a-fetoprotein positive cells.

ELF mRNA distribution in mesodermal tissues versus Alpha fetoprotein mRNA in endodermal tissue:

Since Northern analysis revealed elf expression to occur in day 11.5 heart and liver tissue, we investigated whether elf expression was restricted specifically to mesodermal tissue from the heart and the liver and compared this to the endothelial expression of α-fetoprotein. Three main regions of mesoderm can be discriminated in the developing embryo: dorsal (somitic), intermediate, and lateral. Lateral plate mesoderm comprises somatic (pleura, pericardium, peritoneum and limb bud), and splanchnic (heart-epicardium, myocardium, connective tissue and smooth muscles of viscera and blood vessels, hemangioblastic tissue, adrenal cortex and spleen). Regarding the developing heart, at day 9 (13–20 somites), this is seen to beat regularly and strongly. At this stage, the heart appears to be the only region within the embryo where the endothelial elements of the circulation are surrounded by a vessel wall. The walls of the common ventricular chamber as well as the common atrial chamber show an increasing degree of trabeculation. Of note, the space between the endothelial and myocardial elements is filled with loose mesenchyme called cardiac jelly. In situ hybridization of days 9 and 10 embryonic heart tissue using elf antisense riboprobes demonstrated high levels of labeling to both the atrial and ventricular regions. Hepatic mesenchyme also originates from lateral plate mesoderm. The septum transversum part of the hepatic mesenchyme originates from the splanchnic mesoderm of the precardiac area and this is thought to be responsible for the subsequent differentiation of hepatocytes. However, tissue explant experiments have shown that all derivatives of the lateral plate can replace hepatic mesenchyme for these later events. While these initial experiments have demonstrated migrating endoderm must interact with mesenchyme for the former to differentiate into hepatocytes (Le Douarin, 1975, supra; Houssaint, *Cell Differ.* 9:269–279, 1980), more recent studies investigating albumin mRNA expression as an indicator of hepatocyte differentiation, have confirmed these features: initial expression of albumin mRNA occurs during the invasion of the septum transversum, when the hepatic precursor cells clearly contact cardiac mesenchymal tissue. Similarly, primer extension analysis of albumin transcription has revealed the start site of transcription to occur at day 10.5 with a 15–20 fold increase in albumin mRNA upon liver organ formation by day 12.5. In our experiments using α-fetoprotein as a marker for differentiated hepatocytes, it was clear under high magnification, that while a-fetoprotein expression is restricted to the later endodermal component of liver development, elf expression seems to occur in the loosely organized, lighter staining mesenchymal cells—initially cardiac mesenchyme (at day 9.5), then in both cardiac and hepatic tissue (at day 10.5) and then restricted to liver tissue (day 11.5 onwards; elf expression then decreasing upon liver formation. Examination of the later histological sections (days 11 onwards) showed a diffuse distribution of grains. The resolution that was attained did not allow one to draw a firm conclusion about the identity of the hybridizing cells, although it seemed that the hybridization signal with elf was localized in the perisinusoidal cells, but not in the hepatocytes.

Distribution of elf RNA in Adult tissues, conservation in evolution:

Further characterization of elf has involved RNA analysis of adult mouse tissues. Elf hybridizes to adult liver, kidney and testis as a 2.1 Kb transcript in liver and kidney and a 2.6 Kb transcript in adult testis, in very low abundance. Genomic analysis of elf DNA from human, monkey, rat, mouse, dog, cow, rabbit, chicken and yeast indicates that elf is conserved across the species, being represented in all except rabbit DNA.

In vitro transcription and translation of elf, the latter using nuclease-treated rabbit reticulocyte lysate (promega), has revealed a 34 Kd protein, which is as predicted by the elf insert size and indicating that this insert is in frame for the coding sequence for a specific protein.

Embryonic liver explants cultures:

One of the goals of the investigations in conjunction with the present invention was to establish a functional assay for determining the developmental roles of elf and ss3 in liver formation. Mouse embryonic liver explants were cultured in our laboratory, in order to overcome the dissection and analysis of extremely small tissue sections at day 10–10.5 when the liver bud is 0.2 mm. When cultured in the complete absence of mesodermal derivatives, hepatic endoderm deteriorates rapidly. Only 2 out of 15 such liver explants survived. Hematoxylin and eosin staining showed a necrotic endoderm with no apparent signs of hepatic differentiation. When associated with the surrounding mesoderm particularly cardiac mesoderm (en bloc dissections), the endodermal cells had proliferated and invaded the mesoderm strands. Hepatocytes were seen to be organized in cords separated by sinusoids with pseudo-lobule formation. All 15 out of 15 cultures from en bloc dissections were completely viable. These studies confirm prior explant studies demonstrating the necessity of surrounding mesoderm for liver formation. Semi-quantitative RT-PCR analyses of elf, other clones ss3, 145, HNF 3β with GAPDH and α-fetoprotein as controls demonstrate increased expression during mesodermal—endodermal interactions.

Early experiments in chick embryos (Le Douarin, 1975, supra) have demonstrated that at the primitive streak stage, the prospective hepatic area is localized in the middle and in the lateral areas anterior to Hensen's node. At the head process stage, prospective liver areas coincide with cardiac areas, being concentrated in bilateral areas extending from the tip of the head process to an area slightly behind the primitive pit. Potential liver areas were tested by transplantation of pieces of tissue on the chorioallantoic membrane; liver differentiation in such explants was dependent upon the presence of cardiac tissue: no liver tissue was found without cardiac cells in the vicinity, whereas some grafts contained heart tissue without liver. After gastrulation is completed, it is during the somitic stage that the liver and heart segregate partially—the presumptive cardiac mesenchyme migrates anteriorly and venally into the cardiac fold, the prospective myocardial cells becoming incorporated in the heart anlage. Another series of experiments using carbon particle labeling, radiodestruction and coelomic transplantation of pieces of blastoderm showed liver endodermal and mesodermal areas which am superimposed during the early embryonic stages evolve differently later on.

Tissue explant studies have revealed that in normal liver development, hepatocyte differentiation and the formation of liver lobes is entirely dependent upon the mesodermal component which then becomes progressively colonized by the growing endoderm hepatic cords (see Le Douarin, 1975, supra). These stimulating properties of the cardiac, and then, hepatic mesenchyme have been demonstrated to begin at the 5 somite stage and last throughout embryonic life. The findings set forth herein show that elf is expressed in early cardiac mesoderm, with subsequent expression being limited to hepatic mesoderm, revealing this to be a novel marker for the mesodermal component of liver development. Of note, in normal development, pure liver mesenchyme is never observed. That these explant studies have demonstrated expression of elf, indicates that the elf protein will be useful in identifying and studying such interactions between mesoderm and foregut endoderm.

| Summary of events during hepatocyte formation indicating a role for elf | | |
|---|---|---|
| Embryonic | | |
| Stage | endodermal cell hypertrophy | |
| day 9.5 | change in cell polarity | elf expression |
| day 10.5 | invasion and migration into surrounding mesenchyme | |
| day 11.5 | pseudolobule formation, cords of hepatocytes, early sinusoidal formation | |
| day 14.5 | hematopoietic foci and fully differentiated fetal hepatocytes | |

Sequence analysis has shown elf to bear 80% identity to β-fodrin, a non erythroid β-spectrin. β-spectrins have been implicated in numerous functions including the maintenance of cell surface polarity of cells (Nelson et al., *J. Cell. Biol.* 108:893–902, 1989); the maintenance of cell-cell junctions (Thomas et al., *Development* 120:2039–2050, 1994, Luna et al., *Science* 258:955–964, 1992); β-spectrins contain binding sites for other proteins, such as ankyrin and actin (Hu et al., *J. Biol. Chem.* 267:18715–18722, 1992; Speicher et al., *Nature* 311:177–180, 1984). Smaller isoforms β-spectrins have been well described. For instance, a 4.0 Kb muscle tissue transcript is thought to encode a previously reported β-spectrin from clustered acetylcholine receptors. Similarly for elf, the missing domains may be replaced through alternate exon usage to generate proteins with unique functions. A function for elf thus appears to be in the assembly and maintenance of specific domains on the cell surface—towards establishing hepatocyte polarity and thus differentiation.

Spectrins have also been shown to be conserved throughout evolution and am developmentally regulated. These results demonstrate that in keeping with brain β-spectrin (β-G spectrin), elf is also expressed in a tissue and stage specific manner and is conserved throughout evolution (Hu et al., *J. Biol. Chem.* 267:18715–18722, 1992; Zimmer et al., *Brain Res.* 594:75–88, 1992; Leto et al, *Mol. Cell Biol.* 8:1–9, 1988). Elf expression occurs in a gradient-like manner and close examination of Brain β-G spectrin has demonstrated similar gradient patterns, suggesting that a sudden on-off phenomenon at specific time points is simplistic. That elf is maximally expressed at day 10–11 suggests that it has an important function at this time, which continues, although to a lesser extent, with the later stages. For instance, it is conceivable that elf by conferring cell polarity mark the first overt sign of hepatocyte differentiation. Therefore, like Drosophila β-H spectrin, elf may play a role in facilitating a "velcro-like" joining of neighboring cell membranes as they extend (Thomas et al., *Development* 120:2039–2050, 1994). In this way elf may mark the polarization of the surrounding mesodermal cells, enabling foregut endodermal cells to invade this area and differentiate into hepatocytes. Molecular markers have been invaluable in the dissection of inductive events in embryological studies (New et al., *Curr. Opin. Genet. Dev.* 1:196–203, 1991; Sive, *Genes Dev.* 7:1–12, 1993). For instance, in Xenopus, Epi 1, an antibody specific for epidermis, has been used to elucidate the role of the blastopore lip in the neural induction process (Savage et al., *Dev. Biol.* 133:157–168, 1989). Similarly activins (regulating keratin) (Asashima et al., *P.N.A.S.* 88:6511–6514, 1991), vg-1 (Thomsen et al., *Cell* 63:485–493, 1990) and other genes belonging to the TGF-β family, as well as wnt and bFGF families represent components of the cascade leading to the commitment to particular mesodermal fate. For instance, vg-1, originally isolated by differential screening is to cells inducing embryonic mesoderm, the posttranslational processing of Vg-I precursor protein on the future side of the embryo being a key step in generating dorsal mesoderm and body axis in Xenopus (Thomsen et al., *Cell* 74:433–441, 1993). Similarly, in isolating putative inductive agents required for liver formation, a key step is the identification of mRNAs localized to cardiac/liver mesenchyme: elf and its regulatory genes will help to elucidate this area.

More recently, cell-cell interactions have been shown to be important for several cell fate decisions. In *C. elegans* for instance, lin-12 and glp-1 have been shown to encode transmembrane proteins mediating intracellular communication, and are required for the specification of several anterior fates. In Drosophila, the establishment of secondary epithelia which are the result of a mesenchymal-epithelial transition, is thought to be dependent upon two separate adhesions systems: direct interactions between the developing midgut endoderm and the visceral mesoderm on one hand and, adhesive interactions between the epithelial cells themselves on the other. While the latter cell-cell interaction is thought to be controlled by shotgun, control of apicobasal polarity is thought to be caused by genes such as crumbs and stardust (Tepass et al, *Cell* 61:787–799, 1990). Although it is known that the biogenesis of cell surface polarity in hepatocyte formation is an early event, implying that the mechanisms for sorting plasma membrane molecules are functional at an early point, genes involved in cell signaling leading to cell fate in liver development have not been defined to date. The identification of such genes would give tremendous insight into the cell-cell interactions involved in foregut endodermal cell migration and subsequent morphogenesis of the liver as an organ. These studies establish the principle that specific mesoderm mRNAs are localized in a way that guarantees their subsequent segregation to specific mesodermal tissue, in this case the presumed mesodermal component of the liver as demonstrated by embryonic explant studies (Le Douarin, 1975).

Cloning and sequencing of elf:

All embryonic liver was obtained from matings of random-bred ICR mice (Harlan). The plug date was designated as Day 0 and embryos collected at days 10.0, 11.5 and 12.5 p.c.; these were staged by morphological criteria (Theiler, *The House Mouse*, New York: Springer-Verlag, 1989). The livers were dissected, pooled and lysed. To prepare cDNA libraries, RNA was isolated (Chomczynski et al., *Analyt. Biochem.* 162:156–159, 1987) and poly(A)+ RNA selected using oligo(dT)-cellulose (Collaborative Research Type 3). 1 to 5 mg of poly(A)+RNA were used in the preparation of oligo(dT)– primed cDNA libraries. cDNA library construction of days 11.5 and 12.5 embryonic liver was carried out by conventional techniques (Gubler et al., *Gene* 25:263–269, 1983), and the day 10.0 and adult mouse liver using the Stratagene Unizap cDNA library kit. Two subtracted libraries were then constructed (Schweinfest et al., *Genet. Anal. Tech. Appl.* 7:64–70, 1990). The resulting subtracted libraries comprised 64 clones (11.5–12.5), and 110 clones (10.5–11.5). The process involved: (a) Biotinylation: fifty micrograms of cDNA from day 12.5 liver library at 10mg/ml were biotinylated in HE buffer (10 mM Hepes, pH 7.5, 1 mM EDTA, Clontech Labs.); (b) Subtraction was then done by the streptavidin-phenol extraction: the streptavidin-biotin hybrid duplexes represent common gene products which selectively partition into the phenol interface, leaving the unique, subtracted single stranded cDNA in the aqueous phase. After synthesis of second strand DNA and overnight precipitation, one tenth of the DNA was used to transform competent XL Blue cells. Transformation using all the subtracted DNA led to the identification of 174 recombinant colonies. Purification of bacteriophages, preparation of DNA were carried out by the stratagene in vivo excision protocol. Plasmid DNA was sequenced using 77 DNA polymerase (Sanger et al., *J. Mol. Biol.* 143:161–178, 1980).

Sequence analysis:

The NCBI non-redundant (nr) and EST databases were searched using the blastp2 and blastn2 programs, which permit gapped alignments (Altschul et al., *Methods in Enzymology* 256:460–480, 1996), with the default parameters and elf protein or nucleotide sequences as queries.

RNA preparation and analysis:

Embryos were collected at day 10.0, 11.5 and 12.5 p.c. Embryonic livers were dissected in Dulbecco's modified Eagle's medium (high glucose) and 20 mM Hepes pH 7.3. The livers for the specific stages were pooled and total RNA isolated (Chomczynski et al., supra). 10 micrograms of RNA were electrophoresed on a 1% formaldehyde gel and transferred onto Hi-bond nylon membrane (Amersham) using standard procedures (Sambrook et al., 1989, supra). Radioactive, $^{32}$P-labeled probes were synthesized by random primer methods (Feinberg et al., *Analyt. Biochem.* 137:266–267, 1984) and hybridized to the Nylon filters. Filters were washed at high stringency with a final wash in 0.2×SSC (30 mM NaCl, 3 mM sodium citrate, pH 7.4) 0.5% Sodium Dodecyl Sulfate at 65° C. for 60 minutes. Filters for each probe were stripped and rehybridized with other probes to confirm that no cross hybridization signals were obtained under initial screening conditions. These filters were then autoradiographed with intensifying screens at −70° C.

In Situ Analysis:

In situ analysis was performed for elf (Cox et al., *Dev. Bio.* 100:197–206, 1989). The RNA probes were synthesized and labeled with $^{35}$S-UTP (400 Ci/mmole) via the T7 or SP6 promoter for RNA polymerase. Sense or antisense probes were added to the appropriate sections, mounted, sealed with rubber cement and incubated at 50° C. overnight. After incubation, sections were washed with 50% formamide/5× SSC/10 mM DTT (50° C.; 2×30 min.) followed by 4×SSC/TE, incubated with RNase A (20 mg/ml) and RNase TI (500 U/ml; 37° C. 30 min), rinsed again with 4×SSC/TE (37° C., 30 min), twice 2×SSC (25° C., 15 min), twice in 0.1×SSC (25° C., 15 min), dehydrated with an ethanol series (containing 0.3 M ammonium acetate) and air dried. For autoradiography, slides were dipped in NTB 2 emulsion diluted 1:1 with 2% glycerol in water and dried. Exposure times were from @ weeks to four months. The emulsion was developed according to manufacturer's directions.

In Vitro Translation of elf:

Bluescript containing elf was transcribed with T7 RNA polymerase using the in Vitro Eukaryotic Translation kit and MCAP mRNA Capping kit (Stratagene). The RNA transcript was translated in vitro into protein for 90 minutes in the presence of [$^{35}$S]methionine using nuclease-treated rabbit reticulocyte lysate (Promega) and run on 4% denaturing polyacrylamide gels.

Liver explant cultures:

Mouse embryos were obtained from Harlan ICR mice. The age of the embryos was determined by days post appearance of the vaginal plug (day 0). The embryos were further characterized by the number of somites. Isolation of mouse hepatic endoderm, liver buds and mesoderm (en bloc dissection) was as follows: during the 10th day of gestation, the liver bud becomes evident as a thickening of the ventral wall of the foregut, near the origin of the yolk stalk. This ventral endoderm was then either taken alone and cultured, or alternatively with the surrounding mesoderm: the portion of the embryo between the otocyst and the umbilical region. Organ culture: Embryos were placed into nucleopore filters in a humid chamber as described (Houssaint, 1980, supra) and cultured for 48 hours or 96 hours. Microscopy: The explants were fixed as in the in situ hybridization protocols, and RNA isolated as described above. 7 mm sections were stained with hematoxylin, eosin and periodic acid schiff (PAS) for glycogen, an indicator of differentiated hepatocytes. For RNA analysis, semiquantitative RT-PCR was performed.

What is claimed is:

1. An isolated nucleic acid encoding an early liver developmental protein, said nucleic acid having a nucleotide sequence selected from the group consisting of SEQ ID NO:1, SEQ ID NO:3, SEQ ID NO:5, SEQ ID NO:6, SEQ ID NO:8, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and SEQ ID NO:18.

2. An isolated nucleic acid encoding a protein having an amino acid sequence selected from the group consisting of SEQ ID NO:2, SEQ ID NO:4, SEQ ID NO:7 and SEQ ID NO:9.

* * * * *

SEQUENCE LISTING

<160> NUMBER OF SEQ ID NOS: 18

<210> SEQ ID NO 1
<211> LENGTH: 5434
<212> TYPE: DNA
<213> ORGANISM: Mus musculus
<220> FEATURE:
<223> OTHER INFORMATION: For all n's in this sequence, n=(a or g or c or t)
<220> FEATURE:
<221> NAME/KEY: CDS
<222> LOCATION: (1674)..(2069)

<400> SEQUENCE: 1

```
tcgggaaang attgatttgg ccncctcggn aaggcntttt attttgcnnc aaggagggcc      60 cgggggggttt ccaaccnaaa taaaattttt tttcggatcc cggggttttc ctcagggagt     120
tgggaatttt tactttgaaa gcagatnttt cngagntccg ggtagctntc caataactnt     180
ttgtcatcat tgccagacgg cagatcaagg atgccttcgg tttacccgtg ctgttcagag     240
aacggctttt ggaagattga ttttaagtta tttaacagtc acagacaggt gtcatntntg     300
gagaatagag gcaagtccgc ggtgagggat gaagcaggag agattagggg aaggcagaca     360
ggactgctgg gccaaggaag ctgtgctgat ttgagcacag tgggaattca cgtacgcaat     420
ttcaaaggct ttagtggtaa attctgaagc tcagatgcag gcaagaccca agaggatagt     480
gtacacagag agaagagggt cntcaggatc gtgcgtagag tggagagagc cccaaaggca     540
ggagggaaga gcctcagtga ttacttaggg atgagggaga aagaaaaaa ggttcttgca     600 aggtgtgggg tcttccaaat tcaggagttc actgccatat agagaaggtg tagcgggtga     660 aagggggccat gtgatgagga tggcaagcaa ggctgtggcg cagatgacga gatgcctggg     720
tcgggaggtc aggggagacc caggattggg gtcacctgtg tctgcgcaga ggggaagcca     780
ccctgcaact ggcccagcac tgagtccaga ggaaaatgag gcagaggaca aaccagagct     840
tcggagacta agtgcaggta gggcgcgggc ggagcgtgag gagggcagcg gaccacgcga     900
gaggcctcga aggccaccgg acccgcgtcc gagagtctga gggccctgcc cacacctgcg     960 tggcccccctc cccagaggcc acactccaag gccaccctag aacccgtctg tctgctcaag    1020
cccttgcaaa agacgtctgc gcagaggggg cgtggcaggc gtgctgtcac tcacggcctg    1080
ttagccaatc cacgagtgcg cccctccccg gagagggtgc gcggagggcc cgcccccgcc    1140
gccaccgcgg gtgtgaggag gccaggctgg cgcggctccc tccgcccggc agccttgcca    1200
ggtaaccggg ttcggcggga gggctggggg tcgcgcagcc ccctcgctcc ctgggaggcg    1260
tgcacactgc cgcggcgggt cccgtgtggg ccggaggccc gtgcgcgcgt cggaccgacg    1320
ggccgcagcc tgtgggcggg gttgcgtgcg tgacggcgg ccgtgccccg cgttgtgtca    1380
ggcctgcgcg gggaaagctc ggccgaaccg aggtgtccag gtccgcccgc tgcggcctgc    1440
cccgggttgc ggggcgcagg cgcggcggtg ggcggggtc gtccccagga gcgtctttgt     1500
tcccggcgcg ctgagggcgg agcctcaccc cgccccgccc ccgcgctcag tccccgcccc    1560
gcgtccgccc gcaggagctg ccaccgggtc ccgctggcct cccggccgc cgccaccgcc    1620 tccgcctccg ccgctccggg cccgccggct tgcgtcgccg aggtcgctgc agc atg     1676
                                                                 Met
                                                                   1 gcg ggc gtc gcg acc ccc tgc gcc aac ggc tgc ggg cct ggc gca ccc     1724
Ala Gly Val Ala Thr Pro Cys Ala Asn Gly Cys Gly Pro Gly Ala Pro
          5                  10                  15
```

| | | |
|---|---|---|
| tcc gaa gcc gag gtg ctg cac ctc tgc cgc agc ctc gag gtg ggc acc<br>Ser Glu Ala Glu Val Leu His Leu Cys Arg Ser Leu Glu Val Gly Thr<br>20 25 30 | | 1772 |
| gtc atg act ttg ttc tac tcc aag aag tcg cag cgg cca gaa cgg aag<br>Val Met Thr Leu Phe Tyr Ser Lys Lys Ser Gln Arg Pro Glu Arg Lys<br>35 40 45 | | 1820 |
| acc ttc cag gtc aag ttg gag acg cgc cag atc aca tgg agc cgc ggc<br>Thr Phe Gln Val Lys Leu Glu Thr Arg Gln Ile Thr Trp Ser Arg Gly<br>50 55 60 65 | | 1868 |
| gcg gac aaa atc gag ggg tcc agt aag tgc gcc cca ctc cgg cct gcc<br>Ala Asp Lys Ile Glu Gly Ser Ser Lys Cys Ala Pro Leu Arg Pro Ala<br>70 75 80 | | 1916 |
| tcg cgc ctg ccc gcc tcc caa aca ctt ggg caa act ttc ggg cct cgc<br>Ser Arg Leu Pro Ala Ser Gln Thr Leu Gly Gln Thr Phe Gly Pro Arg<br>85 90 95 | | 1964 |
| gcc tgg cgc ccc gtc tcc gcc cag tcc ctg gtg gtc act ctg ggg cgg<br>Ala Trp Arg Pro Val Ser Ala Gln Ser Leu Val Val Thr Leu Gly Arg<br>100 105 110 | | 2012 |
| gtg gag ggg ggc atc cgg gtc ttg gat cac ctg ata gga cac ccc ctc<br>Val Glu Gly Gly Ile Arg Val Leu Asp His Leu Ile Gly His Pro Leu<br>115 120 125 | | 2060 |
| ccc cag tag gggggagtg ttccaggcac tttgccctga ggcctaagag<br>Pro Gln<br>130 | | 2109 |
| tcctcactgg ttggacaagt ggagtgggat tccggccctt agcatcgggc ggctgtcagt | | 2169 |
| ggctgtgagg ggaagccaag acagggaccc cctcatccaa cctgagaacc tggggaaccg | | 2229 |
| acaagatctt cctgcccact gccatttctc cagagtgtgc tgtctgtgaa aactcctaag | | 2289 |
| agctccggga tgggcttatt ggcgcaagaa cctttggaat cctcatgtag aacttaggca | | 2349 |
| gatgttgggg tagggctggt tgtgaagcag agccctactc atctcccctc ttctttggga | | 2409 |
| ggatggggta tgaaagctaa aaccgtgact gcttccccct cccatgtccc gtggatgggt | | 2469 |
| tttttttttt tttttttttg ccccagatct gaattttgga ggtccatggt gctaggcagc | | 2529 |
| catccaaagc tagagccatg gctcctttgc ccttgcagca taacaaggg agcttgcatt | | 2589 |
| cagaaaggtt ccctggcctt gggttttggg gtccagccct tgtgttgga tgttctcgtg | | 2649 |
| accacagggg agcccagagt tgctcctctg gtttcctgtc gtaccttcc caaacctgag | | 2709 |
| tgtggtgggt ttacacacaa gtctctggtg ggagaagtaa gtcaggagtt ttgagaaacc | | 2769 |
| tcggctcttt ctgatagtca ttttcctcgg tgtgaggcag gatgaggagt ctttgcaact | | 2829 |
| ccaggctttg agatgtttct tacaagaacc cccaaagagt ctatggttga agggacctag | | 2889 |
| cctaagagcc aggtctgtgt tagagaaggg ggggtggtgt caggaagtaa caacggagag | | 2949 |
| aaggtcccac agatcttcct ggggatggtg tacatgtgtg tcgatgggtg aggagatgag | | 3009 |
| gaggaaggaa ggtttctgtg gtaagacagc catcctcaac tacaaacttc aggtctgaca | | 3069 |
| gaattggccc ttaaccatca ccagtgccca tcagccctgg cctccgctgg aagaacattt | | 3129 |
| cagtgatttt cagtgttggg ggatggaact gcagacagtt ccggtagtcc tgagacatca | | 3189 |
| ctcagacatc aggttgcagg catggcattt tacgtttgta gtatttcctg tgtttaagtg | | 3249 |
| gtggcattag ttccccggta gctagctctt ggtaacagct gcactgtaaa ccgtgtgtgt | | 3309 |
| agcccagtag tggaagatag ctatggtatt tgaagccagt gtgttagctg tacgtcaccc | | 3369 |
| agccaggtgc tttccctctc ggagcctcgg ttcctctgta agttagcaga agtatattta | | 3429 |
| ctataaatgg tcacttttgg aagtgagata gttggtgtaa agtaagcaaa ctaaatatgt | | 3489 |
| aatagatgcg agcagagacg ttacagaagt ttaagaacca gttattagta gcagtagcta | | 3549 |

```
tggtagatgc ttgtcctcct agaccctggg atggggcttc tgagggaggt ctaatgtggc      3609
tgttagaaaa agaaagggct ctgagggagg agggccgaga gagggtcccg ttctccttaa      3669
ttgcattacc caggataaaa gaggaaactc ttgttttgcc gtacatcgtt taccttctg       3729 ttcacctgtc atgtaagatg agtttctatg tttggaattt tgtacattgg atgccattgt      3789
gagttggggc ctggacagaa agaagggact tagagacaga accatccagt ccgttttgtc      3849
tcacttgggt ctttgaggat gggtggcagg aatacagagg acgtcacctt tccagaccca      3909
caaaagtcac ccagagatat gcatgttttc attgggcccg accctgtgat ttttggggtc      3969
cagaatgaag gctgcagact agcctgtgtg gacttcatac cttgtaaatg gagcccacca      4029
ccgaagccct gccccacttc tgctggaatg cacctcactg cctttgtggg ttcccaaacc      4089
tgcagcctcc tgcagattgt gaaaaggatt gagttgccag ctgggtccct actgtctggt      4149
ctcttgttca gatgcctcag gtatttgact ttttgctgat aaccttatcc ctacctgaag      4209
ccaggccaga gagaaagact gccgctgtct gccctcaggg tgctcacgga acacaacgac      4269
aggctgactg ccatttccta aatcttgagt tctctcactg tgacacctgt gaaactagtt      4329
agcaccttct gatgtctaag gcagcggtct acttgagaag tgctttggtg ctgtttggtt      4389
gtgtgactga agtcaggctg gtgtctggca tttatgttgc agaatttagt gagttaaaag      4449
cagccataga cttcctgccc agtgctaaac agacttttca ctctgctgca ggctagtcct      4509
cagaggactc tgctcccagg ttgtgttggt ggtaggcctt ggtctcctgt tttctgtagc      4569
ctttgttgcc cctgtgaag agaaacctcc atgtttaggt ggtatttaca ggcagagacc      4629
tccatcttca tcaaagacgc cttcctaggc tttccatatg taatgcctgt agtgagatgg      4689
ctcagaccta ttcttcgtga ggttgtccag ttaaggacca ctgttggcat agtagctcca      4749
gtagagactc taaagctatg ttgttattgt ggtgaggatt gcagtaccaa ggggctggct      4809
ctgagagtag gtccgtggca cctaagaatt gtctgcacat gtccctcaag gattcctttt      4869
ngctggccca cagtgagaga gcagcagaaa gcatgcgcct ggatctaaga aaggttaatg      4929
aaaccatggt acctatggga gctttacaac ctgggcttct gtctccggta gccatttcta      4989
aaaganatta tgaaattgtg gtagattgaa agatgttcct tactattcct ttacatcctg      5049
aggatcacga aagatttgct ttcagtattc ctactattaa ttttaaagaa cctatgaaaa      5109
gatatcaatg gacagttctt ccacaaggca tggctaataa tcctacctta tgtcaaantt      5169
gtggcacaac cattcacctg tgagacacaa tgactatgac tactcntcnt gatgatgatg      5229
angatgatga gatgatgatg atgatgatga tgacacacan gatagagatg attctaangc      5289
ggaaanatcc cgactgcttt ncttaaaatt accnncctnc gaaaagatta aacccgaaag      5349
gtcaccgatc tatatttngt ttaantnata ccgtttccca aaattttncg gacctnaant      5409
ttnatcaatt ttgtntatgn tcccc                                           5434
```

<210> SEQ ID NO 2
<211> LENGTH: 131
<212> TYPE: PRT
<213> ORGANISM: Mus musculus

<400> SEQUENCE: 2

Met Ala Gly Val Ala Thr Pro Cys Ala Asn Gly Cys Gly Pro Gly Ala
 1               5                  10                  15

Pro Ser Glu Ala Glu Val Leu His Leu Cys Arg Ser Leu Glu Val Gly
                20                  25                  30

Thr Val Met Thr Leu Phe Tyr Ser Lys Lys Ser Gln Arg Pro Glu Arg
            35                  40                  45

```
Lys Thr Phe Gln Val Lys Leu Glu Thr Arg Gln Ile Thr Trp Ser Arg
     50                  55                  60

Gly Ala Asp Lys Ile Glu Gly Ser Ser Lys Cys Ala Pro Leu Arg Pro
 65                  70                  75                  80

Ala Ser Arg Leu Pro Ala Ser Gln Thr Leu Gly Gln Thr Phe Gly Pro
                 85                  90                  95

Arg Ala Trp Arg Pro Val Ser Ala Gln Ser Leu Val Val Thr Leu Gly
            100                 105                 110

Arg Val Glu Gly Gly Ile Arg Val Leu Asp His Leu Ile Gly His Pro
        115                 120                 125

Leu Pro Gln
    130

<210> SEQ ID NO 3
<211> LENGTH: 6960
<212> TYPE: DNA
<213> ORGANISM: Mus musculus
<220> FEATURE:
<221> NAME/KEY: CDS
<222> LOCATION: (333)..(6794)

<400> SEQUENCE: 3
cctgcgtcct tcctccttttt cctccttccc tcctccctcc cgggtaattt atttctagct      60
tccaggcaag ggccacacaa ggaaggaaat ccacagggga ttagatgccg ggtggtaac      120 tccaccaggc taggttggac tctgcagcca acttcctatc agatcaccct gcacctattt    180
ccgacccgac cggaatgcga ctggcttgag gtccagccct ttcgcctggg cgggagcaga    240
gccgcggaaa ctgcttggag ttggatgggg gtaggaaggg gctggagcgg gaatcctacg   300
```

| | | | | | | |
|---|---|---|---|---|---|---|
| atgcaactgg cctgggccta aggttgggca ta atg gag ttg cag agg aca tcc | | | | | | 353 |
| Met Glu Leu Gln Arg Thr Ser | | | | | | |
| 1 5 | | | | | | |

```
agc gtt tca ggg ccg ctg tcg ccg gcc tac acc ggg cag gtg cct tac     401
Ser Val Ser Gly Pro Leu Ser Pro Ala Tyr Thr Gly Gln Val Pro Tyr
     10                  15                  20 aac tac aac caa ctg gag gga aga ttc aaa cag ctc caa gat gag cgt     449
Asn Tyr Asn Gln Leu Glu Gly Arg Phe Lys Gln Leu Gln Asp Glu Arg
 25                  30                  35 gaa gct gta cag aag aag acc ttc acc aag tgg gtc aat tcc cac ctt     497
Glu Ala Val Gln Lys Lys Thr Phe Thr Lys Trp Val Asn Ser His Leu
 40                  45                  50                  55 gca aga gtg tcc tgc cga atc aca gac ctg tac acg gac ctt cga gat     545
Ala Arg Val Ser Cys Arg Ile Thr Asp Leu Tyr Thr Asp Leu Arg Asp
                 60                  65                  70 gga cgg atg ctc atc aag cta ctg gag gtc ctc tct gga gag agg ctg     593
Gly Arg Met Leu Ile Lys Leu Leu Glu Val Leu Ser Gly Glu Arg Leu
            75                  80                  85 cct aaa ccc act aag gga cgg atg cgg atc cac tgt ctg gag aat gtc     641
Pro Lys Pro Thr Lys Gly Arg Met Arg Ile His Cys Leu Glu Asn Val
         90                  95                 100 gac aag gct ctt caa ttc ctg aaa gag cag aga gtc cat ctt gag aac     689
Asp Lys Ala Leu Gln Phe Leu Lys Glu Gln Arg Val His Leu Glu Asn
105                 110                 115 atg ggc tcc cat gac att gtg gat gga aac cac cgg ctg acc ctc ggc    737
Met Gly Ser His Asp Ile Val Asp Gly Asn His Arg Leu Thr Leu Gly
120                 125                 130                 135 ctc atc tgg aca att att ctg cgc ttc cag atc cag gat att agt gtg    785
Leu Ile Trp Thr Ile Ile Leu Arg Phe Gln Ile Gln Asp Ile Ser Val
                140                 145                 150
```

```
gag act gaa gat aac aaa gag aaa aag tct gct aag gat gca ttg ctg      833
Glu Thr Glu Asp Asn Lys Glu Lys Lys Ser Ala Lys Asp Ala Leu Leu
            155                 160                 165 ctg tgg tgc cag atg aag aca gct ggg tac ccc aat gtc aac att cac      881
Leu Trp Cys Gln Met Lys Thr Ala Gly Tyr Pro Asn Val Asn Ile His
        170                 175                 180 aat ttc acc act agc tgg agg gat ggc atg gcc ttc aat gca ctg ata      929
Asn Phe Thr Thr Ser Trp Arg Asp Gly Met Ala Phe Asn Ala Leu Ile
    185                 190                 195 cat aaa cat cgg cct gac ctg ata gat ttt gat aaa ctg aag aaa tct      977
His Lys His Arg Pro Asp Leu Ile Asp Phe Asp Lys Leu Lys Lys Ser
200                 205                 210                 215 aat gca cac tac aat ctg cag aat gca ttt aac ctg gca gag cag cac     1025
Asn Ala His Tyr Asn Leu Gln Asn Ala Phe Asn Leu Ala Glu Gln His
                220                 225                 230 ctt ggc ctc act aaa ctg tta gac cct gaa gat atc agt gtg gac cac     1073
Leu Gly Leu Thr Lys Leu Leu Asp Pro Glu Asp Ile Ser Val Asp His
            235                 240                 245 cct gat gag aag tct atc atc aca tac gtg gtg act tac tac cac tac     1121
Pro Asp Glu Lys Ser Ile Ile Thr Tyr Val Val Thr Tyr Tyr His Tyr
        250                 255                 260 ttc tcc aag atg aag gcc ttg gct gtc gaa gga aag cgc att gga aag     1169
Phe Ser Lys Met Lys Ala Leu Ala Val Glu Gly Lys Arg Ile Gly Lys
    265                 270                 275 gtg ctt gat aat gct ata gaa aca gag aaa atg att gag aag tac gag     1217
Val Leu Asp Asn Ala Ile Glu Thr Glu Lys Met Ile Glu Lys Tyr Glu
280                 285                 290                 295 aca ctt gct tct gac ctt ctg gag tgg att gaa caa acc atc atc atc     1265
Thr Leu Ala Ser Asp Leu Leu Glu Trp Ile Glu Gln Thr Ile Ile Ile
                300                 305                 310 cta aac aac cgc aaa ttt gct aat tca ctg gtt ggg gtc caa cag cag     1313
Leu Asn Asn Arg Lys Phe Ala Asn Ser Leu Val Gly Val Gln Gln Gln
            315                 320                 325 ctc caa gca ttc aac acg tac cgc aca gtg gag aaa cca cct aag ttt     1361
Leu Gln Ala Phe Asn Thr Tyr Arg Thr Val Glu Lys Pro Pro Lys Phe
        330                 335                 340 act gag aag ggg aat ttg gag gtg ctc ctt ttc gcg att cag agc aag     1409
Thr Glu Lys Gly Asn Leu Glu Val Leu Leu Phe Ala Ile Gln Ser Lys
    345                 350                 355 atg cga gcg aat aat cag aag gtc tac atg ccc cgc gag ggg aag ctc     1457
Met Arg Ala Asn Asn Gln Lys Val Tyr Met Pro Arg Glu Gly Lys Leu
360                 365                 370                 375 atc tct gac atc aac aag gcc tgg gaa aga ctg gaa aaa gca gaa cat     1505
Ile Ser Asp Ile Asn Lys Ala Trp Glu Arg Leu Glu Lys Ala Glu His
                380                 385                 390 gag aga gaa ctg gct ctg cgg aat gag ctc ata cgg cag gaa aaa ctg     1553
Glu Arg Glu Leu Ala Leu Arg Asn Glu Leu Ile Arg Gln Glu Lys Leu
            395                 400                 405 gaa caa ctc gcc cga aga ttt gat cgc aag gca gct atg agg gag aca     1601
Glu Gln Leu Ala Arg Arg Phe Asp Arg Lys Ala Ala Met Arg Glu Thr
        410                 415                 420 tgg ctg agt gaa aac cag cgt ctt gtg tct cag gac aac ttt gga ttt     1649
Trp Leu Ser Glu Asn Gln Arg Leu Val Ser Gln Asp Asn Phe Gly Phe
    425                 430                 435 gac ctt ccc gct gtt gag gct gct acc aaa aaa cac gag gcc att gag     1697
Asp Leu Pro Ala Val Glu Ala Ala Thr Lys Lys His Glu Ala Ile Glu
440                 445                 450                 455 aca gac atc gct gca tat gaa gaa cga gtt cag gcc gtg gtg gct gtg     1745
Thr Asp Ile Ala Ala Tyr Glu Glu Arg Val Gln Ala Val Val Ala Val
                460                 465                 470
```

-continued

| | |
|---|---|
| gcc agg gaa ctt gaa gcc gag aac tac cat gac atc aag cgc atc aca<br>Ala Arg Glu Leu Glu Ala Glu Asn Tyr His Asp Ile Lys Arg Ile Thr<br>475           480              485 | 1793 |
| gcg agg aag gac aat gtc atc cgg ctc tgg gaa tac ttg ctg gaa ctg<br>Ala Arg Lys Asp Asn Val Ile Arg Leu Trp Glu Tyr Leu Leu Glu Leu<br>490           495              500 | 1841 |
| ctc agg gcc agg agg cag cgt ctt gag atg aac ctg gga ttg caa aag<br>Leu Arg Ala Arg Arg Gln Arg Leu Glu Met Asn Leu Gly Leu Gln Lys<br>505           510              515 | 1889 |
| ata ttc cag gaa atg ctt tat att atg gac tgg atg gat gaa atg aag<br>Ile Phe Gln Glu Met Leu Tyr Ile Met Asp Trp Met Asp Glu Met Lys<br>520           525              530              535 | 1937 |
| gtg cta ttg ctg tct caa gac tat ggc aaa cac tta ctt ggt gtt gaa<br>Val Leu Leu Leu Ser Gln Asp Tyr Gly Lys His Leu Leu Gly Val Glu<br>540           545              550 | 1985 |
| gac ctg tta cag aag cat gcc ctg gtt gaa gca gac att gca atc caa<br>Asp Leu Leu Gln Lys His Ala Leu Val Glu Ala Asp Ile Ala Ile Gln<br>555           560              565 | 2033 |
| gca gag cgt gta aga ggt gtg aat gcc tct gcc cag aag ttt gca aca<br>Ala Glu Arg Val Arg Gly Val Asn Ala Ser Ala Gln Lys Phe Ala Thr<br>570           575              580 | 2081 |
| gat ggg gaa ggc tac aag cca tgt gac ccc cag gta att cga gac cgt<br>Asp Gly Glu Gly Tyr Lys Pro Cys Asp Pro Gln Val Ile Arg Asp Arg<br>585           590              595 | 2129 |
| gtt gcc cac atg gag ttc tgc tat caa gag ctt tgt cag ctg gct gcc<br>Val Ala His Met Glu Phe Cys Tyr Gln Glu Leu Cys Gln Leu Ala Ala<br>600           605              610              615 | 2177 |
| gag cgt agg gct cgc ctg gaa gag tcc cgt cgc ctc tgg aag ttc ttc<br>Glu Arg Arg Ala Arg Leu Glu Glu Ser Arg Arg Leu Trp Lys Phe Phe<br>620           625              630 | 2225 |
| tgg gag atg gca gaa gag gaa ggc tgg ata cga gag aag gaa aag atc<br>Trp Glu Met Ala Glu Glu Glu Gly Trp Ile Arg Glu Lys Glu Lys Ile<br>635           640              645 | 2273 |
| ctg tcc tct gat gat tac ggg aaa gac ttg acc agt gtc atg cgc ctg<br>Leu Ser Ser Asp Asp Tyr Gly Lys Asp Leu Thr Ser Val Met Arg Leu<br>650           655              660 | 2321 |
| ctg agc aag cac cgg gca ttt gag gat gag atg agt ggc cgt agt ggc<br>Leu Ser Lys His Arg Ala Phe Glu Asp Glu Met Ser Gly Arg Ser Gly<br>665           670              675 | 2369 |
| cat ttt gag cag gcc att aaa gaa ggt gaa gac atg att gca gag gaa<br>His Phe Glu Gln Ala Ile Lys Glu Gly Glu Asp Met Ile Ala Glu Glu<br>680           685              690              695 | 2417 |
| cac ttt gga tcg gaa aag atc cgt gag aga atc att tat atc cgg gag<br>His Phe Gly Ser Glu Lys Ile Arg Glu Arg Ile Ile Tyr Ile Arg Glu<br>700           705              710 | 2465 |
| cag tgg gcc aac ctg gaa cag ctc tca gcc att agg aag aag cgc cta<br>Gln Trp Ala Asn Leu Glu Gln Leu Ser Ala Ile Arg Lys Lys Arg Leu<br>715           720              725 | 2513 |
| gag gaa gcc tca tta ctg cac cag ttc cag gct gat gct gat gat att<br>Glu Glu Ala Ser Leu Leu His Gln Phe Gln Ala Asp Ala Asp Asp Ile<br>730           735              740 | 2561 |
| gat gct tgg atg tta gat ata ctc aag att gtc tcc agc aat gat gtg<br>Asp Ala Trp Met Leu Asp Ile Leu Lys Ile Val Ser Ser Asn Asp Val<br>745           750              755 | 2609 |
| ggc cat gat gag tac tcc acg cag tct ctg gtc aag aag cat aaa gat<br>Gly His Asp Glu Tyr Ser Thr Gln Ser Leu Val Lys Lys His Lys Asp<br>760           765              770              775 | 2657 |
| gta gca gaa gag atc acc aac tgc agg ccc act att gac aca ctg cat<br>Val Ala Glu Glu Ile Thr Asn Cys Arg Pro Thr Ile Asp Thr Leu His<br>780           785              790 | 2705 |

-continued

| | | |
|---|---|---|
| gag caa gcc agt gcc ctt cca caa gca cat gca gag tct cca gat gtg<br>Glu Gln Ala Ser Ala Leu Pro Gln Ala His Ala Glu Ser Pro Asp Val<br>795 800 805 | 2753 | |
| aag ggc cgg ctg gca gga att gag gag cgc tgc aag gag atg gca gag<br>Lys Gly Arg Leu Ala Gly Ile Glu Glu Arg Cys Lys Glu Met Ala Glu<br>810 815 820 | 2801 | |
| tta aca cgg cta agg aag cag gct ctg cag gac acc ctg gcc ctg tac<br>Leu Thr Arg Leu Arg Lys Gln Ala Leu Gln Asp Thr Leu Ala Leu Tyr<br>825 830 835 | 2849 | |
| aag atg ttc agt gag gct gat gcc tgt gag ctc tgg att gac gag aag<br>Lys Met Phe Ser Glu Ala Asp Ala Cys Glu Leu Trp Ile Asp Glu Lys<br>840 845 850 855 | 2897 | |
| gag cag tgg ctc aac aac atg cag atc cca gag aag ctg gag gac ctg<br>Glu Gln Trp Leu Asn Asn Met Gln Ile Pro Glu Lys Leu Glu Asp Leu<br>860 865 870 | 2945 | |
| gaa gtc atc cag cac aga ttt gag agc cta gaa cca gaa atg aac aac<br>Glu Val Ile Gln His Arg Phe Glu Ser Leu Glu Pro Glu Met Asn Asn<br>875 880 885 | 2993 | |
| cag gct tcc cgg gtt gct gtg gtg aac cag att gca cgg cag ctg atg<br>Gln Ala Ser Arg Val Ala Val Val Asn Gln Ile Ala Arg Gln Leu Met<br>890 895 900 | 3041 | |
| cac aat ggc cac ccc agt gaa aag gaa atc aga gct cag caa gac aaa<br>His Asn Gly His Pro Ser Glu Lys Glu Ile Arg Ala Gln Gln Asp Lys<br>905 910 915 | 3089 | |
| ctc aac acg agg tgg agt cag ttc aga gaa ctg gtg gac agg aaa aag<br>Leu Asn Thr Arg Trp Ser Gln Phe Arg Glu Leu Val Asp Arg Lys Lys<br>920 925 930 935 | 3137 | |
| gat gct ctt ctg tct gcc ctg agc atc cag aac tac cac ctc gag tgc<br>Asp Ala Leu Leu Ser Ala Leu Ser Ile Gln Asn Tyr His Leu Glu Cys<br>940 945 950 | 3185 | |
| aat gaa acc aaa tcc tgc atc cgg gag aag acc aag gtc atc gag tct<br>Asn Glu Thr Lys Ser Cys Ile Arg Glu Lys Thr Lys Val Ile Glu Ser<br>955 960 965 | 3233 | |
| acc caa gac ctt ggc aat gac ctg gca ggt gtc atg gcc ctg cag tgc<br>Thr Gln Asp Leu Gly Asn Asp Leu Ala Gly Val Met Ala Leu Gln Cys<br>970 975 980 | 3281 | |
| aag ctg act ggc atg gaa cga gac ttg gta gcc att gag gcg aag ctg<br>Lys Leu Thr Gly Met Glu Arg Asp Leu Val Ala Ile Glu Ala Lys Leu<br>985 990 995 | 3329 | |
| agt gac ctg cag aaa gaa gct gag aag ctg gag tcc gag cac cct gac<br>Ser Asp Leu Gln Lys Glu Ala Glu Lys Leu Glu Ser Glu His Pro Asp<br>1000 1005 1010 1015 | 3377 | |
| cag gct caa gct atc ctg tct cgg ctg gcc gag atc agt gat gtg tgg<br>Gln Ala Gln Ala Ile Leu Ser Arg Leu Ala Glu Ile Ser Asp Val Trp<br>1020 1025 1030 | 3425 | |
| gag gaa atg aag aca acc ctg aag aac cga gag gcc tcc ctg gga gag<br>Glu Glu Met Lys Thr Thr Leu Lys Asn Arg Glu Ala Ser Leu Gly Glu<br>1035 1040 1045 | 3473 | |
| gcc agc aag ctg cag cag ttt ctg cgg gac ttg gac gac ttc cag tct<br>Ala Ser Lys Leu Gln Gln Phe Leu Arg Asp Leu Asp Asp Phe Gln Ser<br>1050 1055 1060 | 3521 | |
| tgg ctc tcc agg acc cag act gct atc gcc tca gag gac atg ccc aat<br>Trp Leu Ser Arg Thr Gln Thr Ala Ile Ala Ser Glu Asp Met Pro Asn<br>1065 1070 1075 | 3569 | |
| acc ctc act gag gca gag aag ctt ctc aca cag cac gag aat atc aaa<br>Thr Leu Thr Glu Ala Glu Lys Leu Leu Thr Gln His Glu Asn Ile Lys<br>1080 1085 1090 1095 | 3617 | |
| aat gag atc gac aat tat gag gaa gac tac cag aag atg cgg gac atg<br>Asn Glu Ile Asp Asn Tyr Glu Glu Asp Tyr Gln Lys Met Arg Asp Met<br>1100 1105 1110 | 3665 | |

-continued

| | |
|---|---|
| ggc gag atg gtc acc cag ggg cag act gat gcc cag tat atg ttt ctg<br>Gly Glu Met Val Thr Gln Gly Gln Thr Asp Ala Gln Tyr Met Phe Leu<br>    1115                 1120                 1125 | 3713 |
| cgg cag cgg ctg cag gcc tta gac act ggc tgg aat gag ctc cac aaa<br>Arg Gln Arg Leu Gln Ala Leu Asp Thr Gly Trp Asn Glu Leu His Lys<br>1130                 1135                 1140 | 3761 |
| atg tgg gag aac agg caa aac ctc ctc tcc cag tcc cat gcc tac cag<br>Met Trp Glu Asn Arg Gln Asn Leu Leu Ser Gln Ser His Ala Tyr Gln<br>    1145                 1150                 1155 | 3809 |
| cag ttc ctt agg gac acc aaa caa gct gaa gct ttt ctt aat aac cag<br>Gln Phe Leu Arg Asp Thr Lys Gln Ala Glu Ala Phe Leu Asn Asn Gln<br>1160                 1165                 1170                 1175 | 3857 |
| gag tat gtt ttg gct cat act gaa atg ccc acc acc ctg gaa gga gct<br>Glu Tyr Val Leu Ala His Thr Glu Met Pro Thr Thr Leu Glu Gly Ala<br>        1180                 1185                 1190 | 3905 |
| gaa gca gcc att aaa aag cag gag gac ttc atg acc acc atg gat gcc<br>Glu Ala Ala Ile Lys Lys Gln Glu Asp Phe Met Thr Thr Met Asp Ala<br>    1195                 1200                 1205 | 3953 |
| aac gag gag aag atc aat gct gtt gtg gag act ggc cga aga ctg gtg<br>Asn Glu Glu Lys Ile Asn Ala Val Val Glu Thr Gly Arg Arg Leu Val<br>1210                 1215                 1220 | 4001 |
| agc gat ggg aac atc aac tcc gac cgc atc cag gag aag gtg gac tct<br>Ser Asp Gly Asn Ile Asn Ser Asp Arg Ile Gln Glu Lys Val Asp Ser<br>    1225                 1230                 1235 | 4049 |
| att gac gac aga cac agg aag aat cga gaa gca gcc agt gaa ctt ctg<br>Ile Asp Asp Arg His Arg Lys Asn Arg Glu Ala Ala Ser Glu Leu Leu<br>1240                 1245                 1250                 1255 | 4097 |
| atg agg tta aag gac aac cgt gat cta cag aag ttc ctg caa gat tgt<br>Met Arg Leu Lys Asp Asn Arg Asp Leu Gln Lys Phe Leu Gln Asp Cys<br>        1260                 1265                 1270 | 4145 |
| caa gag ctg tcc ctc tgg atc aat gaa aag atg ctt aca gct caa gac<br>Gln Glu Leu Ser Leu Trp Ile Asn Glu Lys Met Leu Thr Ala Gln Asp<br>    1275                 1280                 1285 | 4193 |
| atg tct tat gat gaa gcc aga aat ctg cac agt aaa tgg tta aag cat<br>Met Ser Tyr Asp Glu Ala Arg Asn Leu His Ser Lys Trp Leu Lys His<br>        1290                 1295                 1300 | 4241 |
| caa gca ttt atg gcg gaa ctt gca tcc aac aaa gaa tgg ctt gac aaa<br>Gln Ala Phe Met Ala Glu Leu Ala Ser Asn Lys Glu Trp Leu Asp Lys<br>    1305                 1310                 1315 | 4289 |
| att gag aag gaa gga atg cag ctt att tca gaa aag cca gaa aca gaa<br>Ile Glu Lys Glu Gly Met Gln Leu Ile Ser Glu Lys Pro Glu Thr Glu<br>1320                 1325                 1330                 1335 | 4337 |
| gct gtg gta aag gaa aaa ctc act ggt tta cat aaa atg tgg gaa gtc<br>Ala Val Val Lys Glu Lys Leu Thr Gly Leu His Lys Met Trp Glu Val<br>        1340                 1345                 1350 | 4385 |
| ctt gaa tcc aca acc cag acc aag gcc cag cgg ctc ttt gat gca aat<br>Leu Glu Ser Thr Thr Gln Thr Lys Ala Gln Arg Leu Phe Asp Ala Asn<br>    1355                 1360                 1365 | 4433 |
| aag gct gag ctt ttc aca caa agc tgc gca gat ctt gac aaa tgg cta<br>Lys Ala Glu Leu Phe Thr Gln Ser Cys Ala Asp Leu Asp Lys Trp Leu<br>    1370                 1375                 1380 | 4481 |
| cat ggc ctg gag agc cag att caa tct gac gac tat ggc aaa gac ctt<br>His Gly Leu Glu Ser Gln Ile Gln Ser Asp Asp Tyr Gly Lys Asp Leu<br>    1385                 1390                 1395 | 4529 |
| acc agt gtc aat att ctt ctg aaa aag caa cag atg ctg gag aat cag<br>Thr Ser Val Asn Ile Leu Leu Lys Lys Gln Gln Met Leu Glu Asn Gln<br>1400                 1405                 1410                 1415 | 4577 |
| atg gaa gtt cgg aag aaa gag atc gag gaa ctg cag agc caa gcc cag<br>Met Glu Val Arg Lys Lys Glu Ile Glu Glu Leu Gln Ser Gln Ala Gln<br>        1420                 1425                 1430 | 4625 |

-continued

| | |
|---|---|
| gcg ctg agt cag gag ggg aag agc aca gat gag gtg gac agc aaa cgc<br>Ala Leu Ser Gln Glu Gly Lys Ser Thr Asp Glu Val Asp Ser Lys Arg<br>1435                        1440                       1445 | 4673 |
| ctt act gtg cag acc aag ttc atg gag ctt ctg gag ccc ttg agt gag<br>Leu Thr Val Gln Thr Lys Phe Met Glu Leu Leu Glu Pro Leu Ser Glu<br>1450                        1455                       1460 | 4721 |
| agg aag cat aac ctg tta gct tcc aag gag atc cat cag ttc aac agg<br>Arg Lys His Asn Leu Leu Ala Ser Lys Glu Ile His Gln Phe Asn Arg<br>1465                        1470                       1475 | 4769 |
| gat gtg gag gac gaa atc cta tgg gtt ggc gag agg atg cct ttg gca<br>Asp Val Glu Asp Glu Ile Leu Trp Val Gly Glu Arg Met Pro Leu Ala<br>1480                        1485                       1490                       1495 | 4817 |
| act tcc aca gat cat ggc cat aac ctt caa act gtg cag ctg tta ata<br>Thr Ser Thr Asp His Gly His Asn Leu Gln Thr Val Gln Leu Leu Ile<br>1500                        1505                       1510 | 4865 |
| aag aaa aac cag acc ctc cag aaa gaa atc cag gga cac cag cct cgt<br>Lys Lys Asn Gln Thr Leu Gln Lys Glu Ile Gln Gly His Gln Pro Arg<br>1515                        1520                       1525 | 4913 |
| att gat gac atc ttt gag agg agt caa aac atc atc aca gat agc agc<br>Ile Asp Asp Ile Phe Glu Arg Ser Gln Asn Ile Ile Thr Asp Ser Ser<br>1530                        1535                       1540 | 4961 |
| agc ctc aat gcc gag gct atc agg cag agg ctc gct gac ctg aag cag<br>Ser Leu Asn Ala Glu Ala Ile Arg Gln Arg Leu Ala Asp Leu Lys Gln<br>1545                        1550                       1555 | 5009 |
| ctg tgg ggg ctc ctc att gag gaa act gag aaa cgc cat aga cgg ctg<br>Leu Trp Gly Leu Leu Ile Glu Glu Thr Glu Lys Arg His Arg Arg Leu<br>1560                        1565                       1570                       1575 | 5057 |
| gag gag gca cac aag gcg cag cag tac tac ttt gat gca gct gaa gcc<br>Glu Glu Ala His Lys Ala Gln Gln Tyr Tyr Phe Asp Ala Ala Glu Ala<br>1580                        1585                       1590 | 5105 |
| gag gca tgg atg agt gaa cag gag ttg tac atg atg tct gag gaa aag<br>Glu Ala Trp Met Ser Glu Gln Glu Leu Tyr Met Met Ser Glu Glu Lys<br>1595                        1600                       1605 | 5153 |
| gcc aag gat gag cag agt gct gtc tct atg ttg aaa aag cac cag att<br>Ala Lys Asp Glu Gln Ser Ala Val Ser Met Leu Lys Lys His Gln Ile<br>1610                        1615                       1620 | 5201 |
| tta gag caa gct gtt gag gac tat gca gag aca gta cac cag ctc tcc<br>Leu Glu Gln Ala Val Glu Asp Tyr Ala Glu Thr Val His Gln Leu Ser<br>1625                        1630                       1635 | 5249 |
| aag act agc cgg gcg ctg gtg gct gac agc cat ccc gaa agt gag cgt<br>Lys Thr Ser Arg Ala Leu Val Ala Asp Ser His Pro Glu Ser Glu Arg<br>1640                        1645                       1650                       1655 | 5297 |
| att agc atg cgg cag tca aag gtc gac aag ctg tat gct ggc ctg aag<br>Ile Ser Met Arg Gln Ser Lys Val Asp Lys Leu Tyr Ala Gly Leu Lys<br>1660                        1665                       1670 | 5345 |
| gac ctt gct gag gag agg aga gga aaa ctt gat gag agg cac agg ctg<br>Asp Leu Ala Glu Glu Arg Arg Gly Lys Leu Asp Glu Arg His Arg Leu<br>1675                        1680                       1685 | 5393 |
| ttc cag ctc aac aga gag gtg gat gac ctg gaa cag tgg atc gct gag<br>Phe Gln Leu Asn Arg Glu Val Asp Asp Leu Glu Gln Trp Ile Ala Glu<br>1690                        1695                       1700 | 5441 |
| agg gaa gtg gtc gca ggc tcc cat gag ttg gga cag gac tat gag cat<br>Arg Glu Val Val Ala Gly Ser His Glu Leu Gly Gln Asp Tyr Glu His<br>1705                        1710                       1715 | 5489 |
| gtc acg atg tta caa gaa cgg ttc cga gaa ttt gct cga gac aca gga<br>Val Thr Met Leu Gln Glu Arg Phe Arg Glu Phe Ala Arg Asp Thr Gly<br>1720                        1725                       1730                       1735 | 5537 |
| aac att ggg cag gag cgt gtg gat aca gtt aat aac atg gca gat gaa<br>Asn Ile Gly Gln Glu Arg Val Asp Thr Val Asn Asn Met Ala Asp Glu<br>1740                        1745                       1750 | 5585 |

```
ctc atc aac tct gga cat tca gat gct gcc acc att gct gag tgg aaa    5633
Leu Ile Asn Ser Gly His Ser Asp Ala Ala Thr Ile Ala Glu Trp Lys
        1755                1760                1765 gat ggt ctc aat gaa gcc tgg gct gac ctc ctg gag ctc att gac aca    5681
Asp Gly Leu Asn Glu Ala Trp Ala Asp Leu Leu Glu Leu Ile Asp Thr
1770                1775                1780 aga aca cag att ctt gct gcc tca tat gaa ctt cat aag ttt tac cat    5729
Arg Thr Gln Ile Leu Ala Ala Ser Tyr Glu Leu His Lys Phe Tyr His
    1785                1790                1795 gat gcc aag gag atc ttt ggc cga atc cag gac aaa cac aag aaa ctc    5777
Asp Ala Lys Glu Ile Phe Gly Arg Ile Gln Asp Lys His Lys Lys Leu
1800                1805                1810                1815 cct gag gag ctt gga aga gat caa aac act gtg gaa act tta cag aga    5825
Pro Glu Glu Leu Gly Arg Asp Gln Asn Thr Val Glu Thr Leu Gln Arg
        1820                1825                1830 atg cac acc acc ttt gag cac gac atc caa gct ctg ggc act cag gtg    5873
Met His Thr Thr Phe Glu His Asp Ile Gln Ala Leu Gly Thr Gln Val
            1835                1840                1845 agg cag ctg cag gag gat gca gct cgc ctc cag gca gcc tat gca ggg    5921
Arg Gln Leu Gln Glu Asp Ala Ala Arg Leu Gln Ala Ala Tyr Ala Gly
        1850                1855                1860 gac aag gct gat gac atc cag aag cgt gag aat gag gtc ctg gaa gcc    5969
Asp Lys Ala Asp Asp Ile Gln Lys Arg Glu Asn Glu Val Leu Glu Ala
    1865                1870                1875 tgg aag tcc ctg ctg gat gct tgt gag ggt cgc agg gtg cgg ctg gta    6017
Trp Lys Ser Leu Leu Asp Ala Cys Glu Gly Arg Arg Val Arg Leu Val
1880                1885                1890                1895 gac aca gga gac aag ttc cgc ttc ttc agc atg gtg cgt gac ctc atg    6065
Asp Thr Gly Asp Lys Phe Arg Phe Phe Ser Met Val Arg Asp Leu Met
        1900                1905                1910 ctc tgg atg gaa gat gtc atc cgg cag atc gag gcc cag gag aaa cca    6113
Leu Trp Met Glu Asp Val Ile Arg Gln Ile Glu Ala Gln Glu Lys Pro
            1915                1920                1925 cgg gat gtg tca tct gtt gaa ctg tta atg aat aat cat caa ggt atc    6161
Arg Asp Val Ser Ser Val Glu Leu Leu Met Asn Asn His Gln Gly Ile
        1930                1935                1940 aaa gct gaa att gat gct cgt aat gac agc ttt aca gcc tgc att gag    6209
Lys Ala Glu Ile Asp Ala Arg Asn Asp Ser Phe Thr Ala Cys Ile Glu
    1945                1950                1955 ctt ggg aaa tcc ctg ctg gca cgg aaa cac tat gct tct gag gag atc    6257
Leu Gly Lys Ser Leu Leu Ala Arg Lys His Tyr Ala Ser Glu Glu Ile
1960                1965                1970                1975 aag gaa aag tta ctg cag ctg aca gag aaa aga aaa gaa atg att gac    6305
Lys Glu Lys Leu Leu Gln Leu Thr Glu Lys Arg Lys Glu Met Ile Asp
        1980                1985                1990 aag tgg gaa gac cgg tgg gag tgg tta aga ctg att ttg gag gtc cat    6353
Lys Trp Glu Asp Arg Trp Glu Trp Leu Arg Leu Ile Leu Glu Val His
            1995                2000                2005 cag ttc tca agg gat gcc agt gtg gca gag gct tgg ctg ctt gga cag    6401
Gln Phe Ser Arg Asp Ala Ser Val Ala Glu Ala Trp Leu Leu Gly Gln
        2010                2015                2020 gaa cca tac cta tcc agc cgt gaa att ggc cag agt gta gac gaa gtg    6449
Glu Pro Tyr Leu Ser Ser Arg Glu Ile Gly Gln Ser Val Asp Glu Val
    2025                2030                2035 gag aag ctt att aag cgc cat gag gcg ttt gaa aag tct gca gcg acc    6497
Glu Lys Leu Ile Lys Arg His Glu Ala Phe Glu Lys Ser Ala Ala Thr
2040                2045                2050                2055 tgg gat gag aga ttc tct gct ctg gaa agg ctg aca acg ttg gag cta    6545
Trp Asp Glu Arg Phe Ser Ala Leu Glu Arg Leu Thr Thr Leu Glu Leu
        2060                2065                2070
```

```
ctg gaa gtg cgc aga cag caa gag gaa gaa aga aag agg cgg cca        6593
Leu Glu Val Arg Arg Gln Gln Glu Glu Glu Arg Lys Arg Arg Pro
         2075                2080                2085 cct tct ccg gac cca aac acg aag gtt tca gag gag gct gag tcc cag    6641
Pro Ser Pro Asp Pro Asn Thr Lys Val Ser Glu Glu Ala Glu Ser Gln
    2090                2095                2100 caa tgg gat act tca aaa gga gac caa gtt tcc cag aat ggt ttg ccg    6689
Gln Trp Asp Thr Ser Lys Gly Asp Gln Val Ser Gln Asn Gly Leu Pro
2105                2110                2115 gct gag cag gga tct cca cgg gtt agt tac cgc tct caa acg tac caa    6737
Ala Glu Gln Gly Ser Pro Arg Val Ser Tyr Arg Ser Gln Thr Tyr Gln
2120                2125                2130                2135 aac tac aaa aac ttt aat agc aga cgg aca gcc agt gac cat tca tgg    6785
Asn Tyr Lys Asn Phe Asn Ser Arg Arg Thr Ala Ser Asp His Ser Trp
                2140                2145                2150 tct gga atg tgaagttcac taccatttgt caagaaccac tctgtccaca            6834
Ser Gly Met tcctttgacc ttttggcttc cacgtcaccc agagtgttaa aattttact taattcatag   6894 ctgtccttga tttcatattt gtttgcattt aatttatgtt tctttggatc ctcattgcct  6954
caaagc                                                             6960

<210> SEQ ID NO 4
<211> LENGTH: 2154
<212> TYPE: PRT
<213> ORGANISM: Mus musculus

<400> SEQUENCE: 4

Met Glu Leu Gln Arg Thr Ser Ser Val Ser Gly Pro Leu Ser Pro Ala
1               5                   10                  15

Tyr Thr Gly Gln Val Pro Tyr Asn Tyr Asn Gln Leu Glu Gly Arg Phe
            20                  25                  30

Lys Gln Leu Gln Asp Glu Arg Glu Ala Val Gln Lys Lys Thr Phe Thr
        35                  40                  45

Lys Trp Val Asn Ser His Leu Ala Arg Val Ser Cys Arg Ile Thr Asp
    50                  55                  60

Leu Tyr Thr Asp Leu Arg Asp Gly Arg Met Leu Ile Lys Leu Leu Glu
65                  70                  75                  80

Val Leu Ser Gly Glu Arg Leu Pro Lys Pro Thr Lys Gly Arg Met Arg
                85                  90                  95

Ile His Cys Leu Glu Asn Val Ser Lys Ala Leu Gln Phe Leu Lys Glu
            100                 105                 110

Gln Arg Val His Leu Glu Asn Met Gly Ser His Asp Ile Val Asp Gly
        115                 120                 125

Asn His Arg Leu Thr Leu Gly Leu Ile Trp Thr Ile Ile Leu Arg Phe
    130                 135                 140

Gln Ile Gln Asp Ile Ser Val Glu Thr Glu Asp Asn Lys Glu Lys Lys
145                 150                 155                 160

Ser Ala Lys Asp Ala Leu Leu Leu Trp Cys Gln Met Lys Thr Ala Gly
                165                 170                 175

Tyr Pro Asn Val Asn Ile His Asn Phe Thr Thr Ser Trp Arg Asp Gly
            180                 185                 190

Met Ala Phe Asn Ala Leu Ile His Lys His Arg Pro Asp Leu Ile Asp
        195                 200                 205

Phe Asp Lys Leu Lys Lys Ser Asn Ala His Tyr Asn Leu Gln Asn Ala
    210                 215                 220

Phe Asn Leu Ala Glu Gln His Leu Gly Leu Thr Lys Leu Leu Asp Pro
```

```
              225                 230                 235                 240
Glu Asp Ile Ser Val Asp His Pro Asp Glu Lys Ser Ile Ile Thr Tyr
                245                 250                 255
Val Val Thr Tyr Tyr His Tyr Phe Ser Lys Met Lys Ala Leu Ala Val
                260                 265                 270
Glu Gly Lys Arg Ile Gly Lys Val Leu Asp Asn Ala Ile Glu Thr Glu
                275                 280                 285
Lys Met Ile Glu Lys Tyr Glu Thr Leu Ala Ser Asp Leu Leu Glu Trp
                290                 295                 300
Ile Glu Gln Thr Ile Ile Ile Leu Asn Asn Arg Lys Phe Ala Asn Ser
305                 310                 315                 320
Leu Val Gly Val Gln Gln Gln Leu Gln Ala Phe Asn Thr Tyr Arg Thr
                325                 330                 335
Val Glu Lys Pro Pro Lys Phe Thr Glu Lys Gly Asn Leu Glu Val Leu
                340                 345                 350
Leu Phe Ala Ile Gln Ser Lys Met Arg Ala Asn Asn Gln Lys Val Tyr
                355                 360                 365
Met Pro Arg Glu Gly Lys Leu Ile Ser Asp Ile Asn Lys Ala Trp Glu
                370                 375                 380
Arg Leu Glu Lys Ala Glu His Glu Arg Glu Leu Ala Leu Arg Asn Glu
385                 390                 395                 400
Leu Ile Arg Gln Glu Lys Leu Glu Gln Leu Ala Arg Arg Phe Asp Arg
                405                 410                 415
Lys Ala Ala Met Arg Glu Thr Trp Leu Ser Glu Asn Gln Arg Leu Val
                420                 425                 430
Ser Gln Asp Asn Phe Gly Phe Asp Leu Pro Ala Val Glu Ala Ala Thr
                435                 440                 445
Lys Lys His Glu Ala Ile Glu Thr Asp Ile Ala Ala Tyr Glu Glu Arg
                450                 455                 460
Val Gln Ala Val Val Ala Val Ala Arg Glu Leu Glu Ala Glu Asn Tyr
465                 470                 475                 480
His Asp Ile Lys Arg Ile Thr Ala Arg Lys Asp Asn Val Ile Arg Leu
                485                 490                 495
Trp Glu Tyr Leu Leu Glu Leu Leu Arg Ala Arg Arg Gln Arg Leu Glu
                500                 505                 510
Met Asn Leu Gly Leu Gln Lys Ile Phe Gln Glu Met Leu Tyr Ile Met
                515                 520                 525
Asp Trp Met Asp Glu Met Lys Val Leu Leu Leu Ser Gln Asp Tyr Gly
                530                 535                 540
Lys His Leu Leu Gly Val Glu Asp Leu Leu Gln Lys His Ala Leu Val
545                 550                 555                 560
Glu Ala Asp Ile Ala Ile Gln Ala Glu Arg Val Arg Gly Val Asn Ala
                565                 570                 575
Ser Ala Gln Lys Phe Ala Thr Asp Gly Glu Gly Tyr Lys Pro Cys Asp
                580                 585                 590
Pro Gln Val Ile Arg Asp Arg Val Ala His Met Glu Phe Cys Tyr Gln
                595                 600                 605
Glu Leu Cys Gln Leu Ala Ala Glu Arg Arg Ala Arg Leu Glu Glu Ser
                610                 615                 620
Arg Arg Leu Trp Lys Phe Phe Trp Glu Met Ala Glu Glu Glu Gly Trp
625                 630                 635                 640
Ile Arg Glu Lys Glu Lys Ile Leu Ser Ser Asp Asp Tyr Gly Lys Asp
                645                 650                 655
```

-continued

```
Leu Thr Ser Val Met Arg Leu Leu Ser Lys His Arg Ala Phe Glu Asp
            660                 665                 670

Glu Met Ser Gly Arg Ser Gly His Phe Glu Gln Ala Ile Lys Glu Gly
            675                 680                 685

Glu Asp Met Ile Ala Glu His Phe Gly Ser Glu Lys Ile Arg Glu
        690                 695                 700

Arg Ile Ile Tyr Ile Arg Glu Gln Trp Ala Asn Leu Glu Gln Leu Ser
705                 710                 715                 720

Ala Ile Arg Lys Lys Arg Leu Glu Glu Ala Ser Leu Leu His Gln Phe
                725                 730                 735

Gln Ala Asp Ala Asp Ile Asp Ala Trp Met Leu Asp Ile Leu Lys
            740                 745                 750

Ile Val Ser Ser Asn Asp Val Gly His Asp Glu Tyr Ser Thr Gln Ser
        755                 760                 765

Leu Val Lys Lys His Lys Asp Val Ala Glu Ile Thr Asn Cys Arg
770                 775                 780

Pro Thr Ile Asp Thr Leu His Glu Gln Ala Ser Ala Leu Pro Gln Ala
785                 790                 795                 800

His Ala Glu Ser Pro Asp Val Lys Gly Arg Leu Ala Gly Ile Glu Glu
                805                 810                 815

Arg Cys Lys Glu Met Ala Glu Leu Thr Arg Leu Arg Lys Gln Ala Leu
                820                 825                 830

Gln Asp Thr Leu Ala Leu Tyr Lys Met Phe Ser Glu Ala Asp Ala Cys
        835                 840                 845

Glu Leu Trp Ile Asp Glu Lys Glu Gln Trp Leu Asn Asn Met Gln Ile
850                 855                 860

Pro Glu Lys Leu Glu Asp Leu Glu Val Ile Gln His Arg Phe Glu Ser
865                 870                 875                 880

Leu Glu Pro Glu Met Asn Asn Gln Ala Ser Arg Val Ala Val Val Asn
                885                 890                 895

Gln Ile Ala Arg Gln Leu Met His Asn Gly His Pro Ser Glu Lys Glu
        900                 905                 910

Ile Arg Ala Gln Gln Asp Lys Leu Asn Thr Arg Trp Ser Gln Phe Arg
        915                 920                 925

Glu Leu Val Asp Arg Lys Lys Asp Ala Leu Leu Ser Ala Leu Ser Ile
        930                 935                 940

Gln Asn Tyr His Leu Glu Cys Asn Glu Thr Lys Ser Cys Ile Arg Glu
945                 950                 955                 960

Lys Thr Lys Val Ile Glu Ser Thr Gln Asp Leu Gly Asn Asp Leu Ala
                965                 970                 975

Gly Val Met Ala Leu Gln Cys Lys Leu Thr Gly Met Glu Arg Asp Leu
        980                 985                 990

Val Ala Ile Glu Ala Lys Leu Ser Asp Leu Gln Lys Glu Ala Glu Lys
        995                 1000                1005

Leu Glu Ser Glu His Pro Asp Gln Ala Gln Ala Ile Leu Ser Arg Leu
    1010                1015                1020

Ala Glu Ile Ser Asp Val Trp Glu Glu Met Lys Thr Thr Leu Lys Asn
025                 1030                1035                1040

Arg Glu Ala Ser Leu Gly Glu Ala Ser Lys Leu Gln Gln Phe Leu Arg
                1045                1050                1055

Asp Leu Asp Asp Phe Gln Ser Trp Leu Ser Arg Thr Gln Thr Ala Ile
            1060                1065                1070

Ala Ser Glu Asp Met Pro Asn Thr Leu Thr Glu Ala Glu Lys Leu Leu
        1075                1080                1085
```

Thr Gln His Glu Asn Ile Lys Asn Glu Ile Asp Asn Tyr Glu Glu Asp
    1090                1095                1100

Tyr Gln Lys Met Arg Asp Met Gly Glu Met Val Thr Gln Gly Gln Thr
105                 1110                1115                1120

Asp Ala Gln Tyr Met Phe Leu Arg Gln Arg Leu Gln Ala Leu Asp Thr
            1125                1130                1135

Gly Trp Asn Glu Leu His Lys Met Trp Glu Asn Arg Gln Asn Leu Leu
        1140                1145                1150

Ser Gln Ser His Ala Tyr Gln Gln Phe Leu Arg Asp Thr Lys Gln Ala
        1155                1160                1165

Glu Ala Phe Leu Asn Asn Gln Glu Tyr Val Leu Ala His Thr Glu Met
    1170                1175                1180

Pro Thr Thr Leu Glu Gly Ala Glu Ala Ala Ile Lys Lys Gln Glu Asp
185                 1190                1195                1200

Phe Met Thr Thr Met Asp Ala Asn Glu Glu Lys Ile Asn Ala Val Val
            1205                1210                1215

Glu Thr Gly Arg Arg Leu Val Ser Asp Gly Asn Ile Asn Ser Asp Arg
        1220                1225                1230

Ile Gln Glu Lys Val Asp Ser Ile Asp Asp Arg His Arg Lys Asn Arg
        1235                1240                1245

Glu Ala Ala Ser Glu Leu Leu Met Arg Leu Lys Asp Asn Arg Asp Leu
    1250                1255                1260

Gln Lys Phe Leu Gln Asp Cys Gln Glu Leu Ser Leu Trp Ile Asn Glu
265                 1270                1275                1280

Lys Met Leu Thr Ala Gln Asp Met Ser Tyr Asp Glu Ala Arg Asn Leu
            1285                1290                1295

His Ser Lys Trp Leu Lys His Gln Ala Phe Met Ala Glu Leu Ala Ser
        1300                1305                1310

Asn Lys Glu Trp Leu Asp Lys Ile Glu Lys Glu Gly Met Gln Leu Ile
        1315                1320                1325

Ser Glu Lys Pro Glu Thr Glu Ala Val Val Lys Glu Lys Leu Thr Gly
    1330                1335                1340

Leu His Lys Met Trp Glu Val Leu Glu Ser Thr Thr Gln Thr Lys Ala
345                 1350                1355                1360

Gln Arg Leu Phe Asp Ala Asn Lys Ala Glu Leu Phe Thr Gln Ser Cys
            1365                1370                1375

Ala Asp Leu Asp Lys Trp Leu His Gly Leu Glu Ser Gln Ile Gln Ser
        1380                1385                1390

Asp Asp Tyr Gly Lys Asp Leu Thr Ser Val Asn Ile Leu Leu Lys Lys
        1395                1400                1405

Gln Gln Met Leu Glu Asn Gln Met Glu Val Arg Lys Lys Glu Ile Glu
    1410                1415                1420

Glu Leu Gln Ser Gln Ala Gln Ala Leu Ser Gln Glu Gly Lys Ser Thr
425                 1430                1435                1440

Asp Glu Val Asp Ser Lys Arg Leu Thr Val Gln Thr Lys Phe Met Glu
            1445                1450                1455

Leu Leu Glu Pro Leu Ser Glu Arg Lys His Asn Leu Leu Ala Ser Lys
        1460                1465                1470

Glu Ile His Gln Phe Asn Arg Asp Val Glu Asp Glu Ile Leu Trp Val
        1475                1480                1485

Gly Glu Arg Met Pro Leu Ala Thr Ser Thr Asp His Gly His Asn Leu
    1490                1495                1500

Gln Thr Val Gln Leu Leu Ile Lys Lys Asn Gln Thr Leu Gln Lys Glu

```
    1505                1510                1515                1520
Ile Gln Gly His Gln Pro Arg Ile Asp Asp Ile Phe Glu Arg Ser Gln
            1525                1530                1535

Asn Ile Ile Thr Asp Ser Ser Ser Leu Asn Ala Glu Ala Ile Arg Gln
        1540                1545                1550

Arg Leu Ala Asp Leu Lys Gln Leu Trp Gly Leu Leu Ile Glu Glu Thr
        1555                1560                1565

Glu Lys Arg His Arg Arg Leu Glu Glu Ala His Lys Ala Gln Gln Tyr
        1570                1575                1580

Tyr Phe Asp Ala Ala Glu Ala Glu Ala Trp Met Ser Glu Gln Glu Leu
1585                1590                1595                1600

Tyr Met Met Ser Glu Glu Lys Ala Lys Asp Glu Gln Ser Ala Val Ser
            1605                1610                1615

Met Leu Lys Lys His Gln Ile Leu Glu Gln Ala Val Glu Asp Tyr Ala
        1620                1625                1630

Glu Thr Val His Gln Leu Ser Lys Thr Ser Arg Ala Leu Val Ala Asp
        1635                1640                1645

Ser His Pro Glu Ser Glu Arg Ile Ser Met Arg Gln Ser Lys Val Asp
        1650                1655                1660

Lys Leu Tyr Ala Gly Leu Lys Asp Leu Ala Glu Glu Arg Arg Gly Lys
1665                1670                1675                1680

Leu Asp Glu Arg His Arg Leu Phe Gln Leu Asn Arg Glu Val Asp Asp
            1685                1690                1695

Leu Glu Gln Trp Ile Ala Glu Arg Glu Val Val Ala Gly Ser His Glu
        1700                1705                1710

Leu Gly Gln Asp Tyr Glu His Val Thr Met Leu Gln Glu Arg Phe Arg
        1715                1720                1725

Glu Phe Ala Arg Asp Thr Gly Asn Ile Gly Gln Glu Arg Val Asp Thr
        1730                1735                1740

Val Asn Asn Met Ala Asp Glu Leu Ile Asn Ser Gly His Ser Asp Ala
1745                1750                1755                1760

Ala Thr Ile Ala Glu Trp Lys Asp Gly Leu Asn Glu Ala Trp Ala Asp
            1765                1770                1775

Leu Leu Glu Leu Ile Asp Thr Arg Thr Gln Ile Leu Ala Ala Ser Tyr
        1780                1785                1790

Glu Leu His Lys Phe Tyr His Asp Ala Lys Glu Ile Phe Gly Arg Ile
        1795                1800                1805

Gln Asp Lys His Lys Lys Leu Pro Glu Glu Leu Gly Arg Asp Gln Asn
        1810                1815                1820

Thr Val Glu Thr Leu Gln Arg Met His Thr Thr Phe Glu His Asp Ile
1825                1830                1835                1840

Gln Ala Leu Gly Thr Gln Val Arg Gln Leu Gln Glu Asp Ala Ala Arg
            1845                1850                1855

Leu Gln Ala Ala Tyr Ala Gly Asp Lys Ala Asp Asp Ile Gln Lys Arg
        1860                1865                1870

Glu Asn Glu Val Leu Glu Ala Trp Lys Ser Leu Leu Asp Ala Cys Glu
        1875                1880                1885

Gly Arg Arg Val Arg Leu Val Asp Thr Gly Asp Lys Phe Arg Phe Phe
        1890                1895                1900

Ser Met Val Arg Asp Leu Met Leu Trp Met Glu Asp Val Ile Arg Gln
1905                1910                1915                1920

Ile Glu Ala Gln Glu Lys Pro Arg Asp Val Ser Ser Val Glu Leu Leu
            1925                1930                1935
```

| Met | Asn | Asn | His | Gln | Gly | Ile | Lys | Ala | Glu | Ile | Asp | Ala | Arg | Asn | Asp |
|---|---|---|---|---|---|---|---|---|---|---|---|---|---|---|---|
| | 1940 | | | | 1945 | | | | | 1950 | | | | | |

| Ser | Phe | Thr | Ala | Cys | Ile | Glu | Leu | Gly | Lys | Ser | Leu | Leu | Ala | Arg | Lys |
|---|---|---|---|---|---|---|---|---|---|---|---|---|---|---|---|
| | 1955 | | | | 1960 | | | | 1965 | | | | | | |

| His | Tyr | Ala | Ser | Glu | Glu | Ile | Lys | Glu | Lys | Leu | Leu | Gln | Leu | Thr | Glu |
|---|---|---|---|---|---|---|---|---|---|---|---|---|---|---|---|
| | 1970 | | | | 1975 | | | | 1980 | | | | | | |

| Lys | Arg | Lys | Glu | Met | Ile | Asp | Lys | Trp | Glu | Asp | Arg | Trp | Glu | Trp | Leu |
|---|---|---|---|---|---|---|---|---|---|---|---|---|---|---|---|
| 985 | | | | 1990 | | | | 1995 | | | | 2000 | | | |

| Arg | Leu | Ile | Leu | Glu | Val | His | Gln | Phe | Ser | Arg | Asp | Ala | Ser | Val | Ala |
|---|---|---|---|---|---|---|---|---|---|---|---|---|---|---|---|
| | | 2005 | | | | 2010 | | | | 2015 | | | | | |

| Glu | Ala | Trp | Leu | Leu | Gly | Gln | Glu | Pro | Tyr | Leu | Ser | Ser | Arg | Glu | Ile |
|---|---|---|---|---|---|---|---|---|---|---|---|---|---|---|---|
| | | 2020 | | | | 2025 | | | | 2030 | | | | | |

| Gly | Gln | Ser | Val | Asp | Glu | Val | Glu | Lys | Leu | Ile | Lys | Arg | His | Glu | Ala |
|---|---|---|---|---|---|---|---|---|---|---|---|---|---|---|---|
| | | 2035 | | | | 2040 | | | | 2045 | | | | | |

| Phe | Glu | Lys | Ser | Ala | Ala | Thr | Trp | Asp | Glu | Arg | Phe | Ser | Ala | Leu | Glu |
|---|---|---|---|---|---|---|---|---|---|---|---|---|---|---|---|
| | | 2050 | | | | 2055 | | | | 2060 | | | | | |

| Arg | Leu | Thr | Thr | Leu | Glu | Leu | Leu | Glu | Val | Arg | Arg | Gln | Gln | Glu | Glu |
|---|---|---|---|---|---|---|---|---|---|---|---|---|---|---|---|
| 065 | | | 2070 | | | | 2075 | | | | 2080 | | | | |

| Glu | Glu | Arg | Lys | Arg | Arg | Pro | Pro | Ser | Pro | Asp | Pro | Asn | Thr | Lys | Val |
|---|---|---|---|---|---|---|---|---|---|---|---|---|---|---|---|
| | | | 2085 | | | | 2090 | | | | | 2095 | | | |

| Ser | Glu | Glu | Ala | Glu | Ser | Gln | Gln | Trp | Asp | Thr | Ser | Lys | Gly | Asp | Gln |
|---|---|---|---|---|---|---|---|---|---|---|---|---|---|---|---|
| | | | 2100 | | | | 2105 | | | | 2110 | | | | |

| Val | Ser | Gln | Asn | Gly | Leu | Pro | Ala | Glu | Gln | Gly | Ser | Pro | Arg | Val | Ser |
|---|---|---|---|---|---|---|---|---|---|---|---|---|---|---|---|
| | | 2115 | | | | 2120 | | | | 2125 | | | | | |

| Tyr | Arg | Ser | Gln | Thr | Tyr | Gln | Asn | Tyr | Lys | Asn | Phe | Asn | Ser | Arg | Arg |
|---|---|---|---|---|---|---|---|---|---|---|---|---|---|---|---|
| | 2130 | | | | 2135 | | | | 2140 | | | | | | |

| Thr | Ala | Ser | Asp | His | Ser | Trp | Ser | Gly | Met |
|---|---|---|---|---|---|---|---|---|---|
| 145 | | | | | 2150 | | | | |

```
<210> SEQ ID NO 5
<211> LENGTH: 8176
<212> TYPE: DNA
<213> ORGANISM: Mus musculus

<400> SEQUENCE: 5
cctgcgtcct tcctccttt cctccttccc tcctccctcc cgggtaattt atttctagct      60
tccaggcaag ggccacacaa ggaaggaaat ccacagggga ttagatgccg gggtggtaac    120
tccaccaggc taggttggac tctgcagcca acttcctatc agatcaccct gcacctattt    180
ccgacccgac cggaatgcga ctggcttgag gtccagccct ttcgcctggg cgggagcaga    240
gccgcggaag ctgcttggag ttggatgggg gtaggaaggg gctggagcgg gaatcctacg    300
atgcaactgg cctgggccta aggttgggca taatggagtt gcagaggaca tccagcgttt    360
cagggccgct gtcgccggcc tacaccgggc aggtgcctta caactacaac caactggagg    420
gaagattcaa acagctccaa gatgagcgtg aagctgtaca agaagacc ttcaccaagt     480
gggtcaattc ccaccttgca agagtgtcct gccgaatcac agacctgtac acggaccttc   540
gagatggacg gatgctcatc aagctactgg aggtcctctc tggagagagg ctgcctaaac   600
ccactaaggg acggatgcgg atccactgtc tggagaatgt cgacaaggct cttcaattcc   660
tgaaagagca gagagtccat cttgagaaca tgggctccca tgcattgtg gatggaaacc    720
accggctgac cctcggcctc atctggacaa ttattctgcg cttccagatc caggatatta    780
gtgtggagac tgaagataac aaagagaaaa agtctgctaa ggatgcattg ctgctgtggt   840
gccagatgaa gacagctggg tacccccaatg tcaacattca caatttcacc actagctgga    900
```

```
gggatggcat ggccttcaat gcactgatac ataaacatcg gcctgacctg atagattttg    960
ataaactgaa gaaatctaat gcacactaca atctgcagaa tgcatttaac ctggcagagc   1020
agcaccttgg cctcactaaa ctgttagacc ctgaagatat cagtgtggac cacccctgatg  1080 agaagtctat catcacatac gtggtgactt actaccacta cttctccaag atgaaggcct   1140
tggctgtcga aggaaagcgc attggaaagg tgcttgataa tgctatagaa acagagaaaa   1200
tgattgagaa gtacgagaca cttgcttctg accttctgga gtggattgaa caaaccatca   1260
tcatcctaaa caaccgcaaa tttgctaatt cactggttgg ggtccaacag cagctccaag   1320
cattcaacac gtaccgcaca gtggagaaac cacctaagtt tactgagaag gggaatttgg   1380
aggtgctcct tttcgcgatt cagagcaaga tgcgagcgaa taatcagaag gtctacatgc   1440
cccgcgaggg gaagctcatc tctgacatca acaaggcctg ggaaagactg gaaaaagcag   1500
aacatgagag agaactggct ctgcggaatg agctcatacg gcaggaaaaa ctggaacaac   1560
tcgcccgaag atttgatcgc aaggcagcta tgagggagac atggctgagt gaaaaccagc   1620
gtcttgtgtc tcaggacaac tttggatttg accttcccgc tgttgaggct gctaccaaaa   1680
aacacgaggc cattgagaca gacatcgctg catatgaaga acgagttcag gccgtggtgg   1740
ctgtggccag ggaacttgaa gccgagaact accatgacat caagcgcatc acagcgagga   1800
aggacaatgt catccggctc tgggaatact gctggaact gctcagggcc aggaggcagc    1860
gtcttgagat gaacctggga ttgcaaaaga tattccagga aatgctttat attatggact   1920
ggatggatga aatgaaggtg ctattgctgt ctcaagacta tggcaaacac ttacttggtg   1980
ttgaagacct gttacagaag catgccctgg ttgaagcaga cattgcaatc caagcagagc   2040
gtgtaagagg tgtgaatgcc tctgcccaga gtttgcaac agatggggaa ggctacaagc    2100
catgtgaccc ccaggtaatt cgagaccgtg ttgcccacat ggagttctgc tatcaagagc   2160
tttgtcagct ggctgccgag cgtagggctc gcctggaaga gtcccgtcgc ctctggaagt   2220
tcttctggga gatggcagaa gaggaaggct ggatacgaga gaaggaaaag atcctgtcct   2280
ctgatgatta cgggaaagac ttgaccagtg tcatgcgcct gctgagcaag caccgggcat   2340
ttgaggatga gatgagtggc cgtagtggcc attttgagca ggccattaaa gaaggtgaag   2400
acatgattgc agaggaacac tttggatcgg aaaagatccg tgagagaatc atttatatcc   2460
gggagcagtg ggccaacctg gaacagctct cagccattag gaagaagcgc ctagaggaag   2520
cctcattact gcaccagttc caggctgatg ctgatgatat tgatgcttgg atgttagata   2580
tactcaagat tgtctccagc aatgatgtgg gccatgatga gtactccacg cagtctctgg   2640
tcaagaagca taaagatgta gcagaagaga tcaccaactg caggcccact attgacacac   2700
tgcatgagca agccagtgcc cttccacaag cacatgcaga gtctccagat gtgaagggcc   2760
ggctggcagg aattgaggag cgctgcaagg agatggcaga gttaacacgg ctaaggaagc   2820
aggctctgca ggacaccctg gccctgtaca agatgttcag tgaggctgat gcctgtgagc   2880
tctggattga cgagaaggag cagtggctca caacatgca gatcccagag aagctggagg    2940
acctggaagt catccagcac agatttgaga gcctagaacc agaaatgaac aaccaggctt   3000
cccgggttgc tgtggtgaac cagattgcac ggcagctgat gcacaatggc cacccccagtg  3060 aaaaggaaat cagagctcag caagacaaac tcaacacgag gtggagtcag ttcagagaac   3120
tggtggacag gaaaaaggat gctcttctgt ctgccctgag catccagaac taccacctcg   3180
agtgcaatga aaccaaatcc tgcatccggg agaagaccaa ggtcatcgag tctacccaag   3240
accttggcaa tgacctggca ggtgtcatgg ccctgcagtg caagctgact ggcatggaac   3300
```

```
gagacttggt agccattgag gcgaagctga gtgacctgca gaaagaagct gagaagctgg    3360
agtccgagca ccctgaccag gctcaagcta tcctgtctcg gctggccgag atcagtgatg    3420
tgtgggagga aatgaagaca accctgaaga accgagaggc ctccctggga gaggccagca    3480
agctgcagca gtttctgcgg gacttggacg acttccagtc ttggctctcc aggacccaga    3540
ctgctatcgc ctcagaggac atgcccaata ccctcactga ggcagagaag cttctcacac    3600
agcacgagaa tatcaaaaat gagatcgaca attatgagga agactaccag aagatgcggg    3660
acatgggcga gatggtcacc caggggcaga ctgatgccca gtatatgttt ctgcggcagc    3720
ggctgcaggc cttagacact ggctggaatg agctccacaa aatgtgggag aacaggcaaa    3780
acctcctctc ccagtcccat gcctaccagc agttccttag ggacaccaaa caagctgaag    3840
cttttcttaa taaccaggag tatgttttgg ctcatactga aatgcccacc accctggaag    3900
gagctgaagc agccattaaa aagcaggagg acttcatgac caccatggat gccaacgagg    3960
agaagatcaa tgctgttgtg gagactggcc gaagactggt gagcgatggg aacatcaact    4020
ccgaccgcat ccaggagaag gtggactcta ttgacgacag acacaggaag aatcgagaag    4080
cagccagtga acttctgatg aggttaaagg acaaccgtga tctacagaag ttcctgcaag    4140
attgtcaaga gctgtccctc tggatcaatg aaaagatgct tacagctcaa gacatgtctt    4200
atgatgaagc cagaaatctg cacagtaaat ggttaaagca tcaagcattt atggcggaac    4260
ttgcatccaa caaagaatgg cttgacaaaa ttgagaagga aggaatgcag cttatttcag    4320
aaaagccaga aacagaagct gtggtaaagg aaaaactcac tggtttacat aaaatgtggg    4380
aagtccttga atccacaacc cagaccaagg cccagcggct ctttgatgca ataaggctg     4440 agcttttcac acaaagctgc gcagatcttg acaaatggct acatggcctg gagagccaga    4500
ttcaatctga cgactatggc aaagacctta ccagtgtcaa tattcttctg aaaaagcaac    4560
agatgctgga gaatcagatg gaagttcgga agaaagagat cgaggaactg cagagccaag    4620
cccaggcgct gagtcaggag gggaagagca cagatgaggt ggacagcaaa cgccttactg    4680
tgcagaccaa gttcatggag cttctggagc ccttgagtga gaggaagcat aacctgttag    4740
cttccaagga gatccatcag ttcaacaggg atgtggagga cgaaatccta tgggttggcg    4800
agaggatgcc tttggcaact tccacagatc atggccataa ccttcaaact gtgcagctgt    4860
taataaagaa aaaccagacc ctccagaaag aaatccaggg acaccagcct cgtattgatg    4920
acatctttga gaggagtcaa aacatcatca cagatagcag cagcctcaat gccgaggcta    4980
tcaggcagag gctcgctgac ctgaagcagc tgtgggggct cctcattgag gaaactgaga    5040
aacgccatag acggctggag gaggcacaca aggcgcagca gtactacttt gatgcagctg    5100
aagccgaggc atggatgagt gaacaggagt tgtacatgat gtctgaggaa aaggccaagg    5160
atgagcagag tgctgtctct atgttgaaaa agcaccagat tttagagcaa gctgttgagg    5220
actatgcaga gacagtacac cagctctcca agactagccg ggcgctggtg gctgacagcc    5280
atcccgaaag tgagcgtatt agcatgcggc agtcaaaggt cgacaagctg tatgctggcc    5340
tgaaggacct tgctgaggag aggagaggaa aacttgatga gaggcacagg ctgttccagc    5400
tcaacagaga ggtggatgac ctggaacagt ggatcgctga gagggaagtg gtcgcaggct    5460
cccatgagtt gggacaggac tatgagcatg tcacgatgtt acaagaacgg ttccgagaat    5520 tgctcgaga cacaggaaac attgggcagg agcgtgtgga tacagttaat aacatggcag    5580
atgaactcat caactctgga cattcagatg ctgccaccat tgctgagtgg aaagatggtc    5640
tcaatgaagc ctgggctgac ctcctggagc tcattgacac aagaacacag attcttgctg    5700
```

```
cctcatatga acttcataag ttttaccatg atgccaagga gatctttggc cgaatccagg    5760
acaaacacaa gaaactccct gaggagcttg gaagagatca aaacactgtg gaaactttac    5820
agagaatgca caccacctttt gagcacgaca tccaagctct gggcactcag gtgaggcagc    5880
tgcaggagga tgcagctcgc ctccaggcag cctatgcagg ggacaaggct gatgacatcc    5940
agaagcgtga gaatgaggtc ctggaagcct ggaagtccct gctggatgct tgtgagggtc    6000
gcagggtgcg gctggtagac acaggagaca agttccgctt cttcagcatg gtgcgtgacc    6060
tcatgctctg gatggaagat gtcatccggc agatcgaggc ccaggagaaa ccacgggatg    6120
tgtcatctgt tgaactgtta atgaataatc atcaaggtat caaagctgaa attgatgctc    6180
gtaatgacag ctttacagcc tgcattgagc ttgggaaatc cctgctggca cggaaacact    6240
atgcttctga ggagatcaag gaaaagttac tgcagctgac agagaaaaga aaagaaatga    6300
ttgacaagtg ggaagaccgg tgggagtggt taagactgat tttggaggtc catcagttct    6360
caagggatgc cagtgtggca gaggcttggc tgcttggaca ggaaccatac ctatccagcc    6420
gtgaaattgg ccagagtgta gacgaagtgg agaagcttat taagcgccat gaggcgtttg    6480
aaaagtctgc agcgacctgg gatgagagat tctctgctct ggaaaggctg acaacgttgg    6540
agctactgga agtgcgcaga cagcaagagg aagaagaaag aaagaggcgg ccaccttctc    6600
cggacccaaa cacgaaggtt tcagaggagg ctgagtccca gcaatgggat acttcaaaag    6660
gagaccaagt ttcccagaat ggtttgccgg ctgagcaggg atctccacgg gttagttacc    6720
gctctcaaac gtaccaaaac tacaaaaact ttaatagcag acggacagcc agtgaccatt    6780
catggtctgg aatgtgaagt tcactaccat ttgtcaagaa ccactctgtc cacatccttt    6840
gaccttttgg cttccacgtc acccagagtg ttaaaatttt tacttaattc atagctgtcc    6900
ttgatttcat atttgtttgc atttaattta tgtttctttg gatcctcatt gcctcaaagc    6960
agcatactta attttttgttt atttattgtg agcttttttac tttaagattt tacatgagta    7020
atcaaaatta aattatagca taatgaaatt agactcttaa caggtacggc acacacaagt    7080
taatagtact ctgctatagg tgctatgtta cttacaagta ttattaacct attggcttcc    7140
attgtatagt agttagtaac tatgaaaact ggtttgtaag gaaggaaacg tttactacta    7200
aggttaggcc tgcagttgct ctggaacatt ccatggagaa tgcattcatc aaacggcccg    7260
aaagaagcta cattttgttg ggaagctgga taagttttag gtgcaggacc ccaaatgttc    7320
tgagaccttt ggggccattt attactttgt acaagcccaa taatcctctc ttttctgcca    7380
agtcctcaac ccagaaatgt aggcttctgt gcaccacacg gcacagccca ctgattgctg    7440
ccaccggctc tgtcttggtc agtgttacca ctgccagcac tcaggctgtg gcagatgcca    7500
gcagctctta ccatcagtca gagtcttcag ggtgtcaagc tgttttcatt ttttaggcaa    7560
atagaacaaa agccatttttg gttcatcctg atcacttgaa tgatagactc aatgccctgt    7620
gcctggcagg gagcgcttgc agaggtgtcc tagccttaga gggctacttc agtgtctcta    7680
ctgacagaaa ctcctgtatc tcaaatggat ctcgaagttc tctagtaagg agtcctaagg    7740
atgacatgta ttgggccact agcagggatt gaaaacattt taaagaaat cctttttctt    7800 aggagtaaaa gctggtaaaa ggggtgactt cctggttctg atcaaaacca gaccaaaccc    7860
tcatttcagc aaagccttgc aagacactcc cttgctcatt tgccatattt agatgtctta    7920
gtggagtcag agccctgttt ggtatgtgtt tttcatgcta agtctaaatt gtcttttcat    7980
ttcatgatgc attttttctc ttttgtcagg ataacatcat atagcatctt gtttgttttt    8040
cctaatctct atgaacatat ctatctacct gtaaccgtag ataggtatct agatagatac    8100
```

```
                                               -continued caagctttta agctctgggc cactatgcat cattattggg tctctgcctt aaaacacatc    8160
caaatttata ttaaaa                                                    8176

<210> SEQ ID NO 6
<211> LENGTH: 1312
<212> TYPE: DNA
<213> ORGANISM: Mus musculus
<220> FEATURE:
<221> NAME/KEY: CDS
<222> LOCATION: (402)..(1061)

<400> SEQUENCE: 6
gcgctgctct gtgagctgga gcacagcgtg cttagagttg gccatattta aaatattttc     60
caataggatc ctgcgtcctt cctccttttc ctccttccct cctccctccc gggtaattta    120
tttctagctt ccaggcaagg gccacacaag gaaggaaatc cacaggggat tagatgccgg    180
ggtggtaact ccaccaggct aggttggact ctgcagccaa cttcctatca gatcaccctg    240
cacctatttc cgacccgacc ggaatgcgac tggcttgagg tccagccctt tcgcctgggc    300
gggagcagag ccgcggaagc tgcttggagt tggatggggg taggaagggg ctggagcggg    360
aatcctacgg tgcaactggc ctgggcctaa ggttgggcat a atg gag ttg cag agg    416
                                              Met Glu Leu Gln Arg
                                                1               5 aca tcc agc att tca ggg ccg ctg tcg ccg gcc tac acc ggg cag gtg      464
Thr Ser Ser Ile Ser Gly Pro Leu Ser Pro Ala Tyr Thr Gly Gln Val
            10                  15                  20 cct tac aac tac aac caa ctg gaa gga aga ttc aaa cag ctc caa gat      512
Pro Tyr Asn Tyr Asn Gln Leu Glu Gly Arg Phe Lys Gln Leu Gln Asp
        25                  30                  35 gag cgt gaa gct gta cag aag aag acc ttc acc aag tgg gtc aat tcc      560
Glu Arg Glu Ala Val Gln Lys Lys Thr Phe Thr Lys Trp Val Asn Ser
    40                  45                  50 cac ctt gcg aga gtg tcc tgc cga atc aca gac ctg tac acg gac ctt      608
His Leu Ala Arg Val Ser Cys Arg Ile Thr Asp Leu Tyr Thr Asp Leu
55                  60                  65 cga gat gga cgg atg ctc atc aag cta ctg gag gtc ctc tct gga gag      656
Arg Asp Gly Arg Met Leu Ile Lys Leu Leu Glu Val Leu Ser Gly Glu
            70                  75                  80                  85 agg ctg cct aaa ccc act aag gga cgg atg cgg atc cac tgt ctg gag      704
Arg Leu Pro Lys Pro Thr Lys Gly Arg Met Arg Ile His Cys Leu Glu
                90                  95                  100 aat gtc gac aag gct ctt caa ttc ctg aaa gag cag aga gtc cat ctt      752
Asn Val Asp Lys Ala Leu Gln Phe Leu Lys Glu Gln Arg Val His Leu
            105                 110                 115 gag aac atg ggc tcc cat gac att gtg gat gga aac cac cgg ctg aca      800
Glu Asn Met Gly Ser His Asp Ile Val Asp Gly Asn His Arg Leu Thr
        120                 125                 130 acg ttg gag cta ctg gaa gtg cgc aga cag caa gag gaa gaa gaa aga      848
Thr Leu Glu Leu Leu Glu Val Arg Arg Gln Gln Glu Glu Glu Glu Arg
    135                 140                 145 aag agg cgg cca cct tct ccg gac cca aac acg aag gtt tca gag gag      896
Lys Arg Arg Pro Pro Ser Pro Asp Pro Asn Thr Lys Val Ser Glu Glu
150                 155                 160                 165 gct gag tcc cag caa tgg gat act tca aaa gga gac caa gtt tcc cag      944
Ala Glu Ser Gln Gln Trp Asp Thr Ser Lys Gly Asp Gln Val Ser Gln
            170                 175                 180 aat ggt ttg ccg gct gag cag gga tct cca cgg gtt agt tac cgc tct      992
Asn Gly Leu Pro Ala Glu Gln Gly Ser Pro Arg Val Ser Tyr Arg Ser
        185                 190                 195 caa acg tac caa aac tac aaa aac ttt aat agc aga cgg aca gcc agt     1040
```

| | | | | | | | | | | | |
|---|---|---|---|---|---|---|---|---|---|---|---|
|Gln|Thr|Tyr|Gln|Asn|Tyr|Lys|Asn|Phe|Asn|Ser|Arg|Arg|Thr|Ala|Ser|
| |200| | | |205| | | |210| | |

```
gac cat tca tgg tct gga atg tgaagttcac taccatttgt caagaaccac         1091
Asp His Ser Trp Ser Gly Met
    215                 220 tctgtccaca tcctttgacc ttttggcttc cacgtcaccc agagtgttaa aattttttact   1151 taattcatag ctgtccttga tttcatattt gtttgcattt aatttatgtt tctttggatc    1211
ctcattgcct caaagcagca tacttaattt ttgtttattt attgtgagct ttttacttta    1271
agattttaca tgagtaatca aaattaaatt atagcataat g                        1312

<210> SEQ ID NO 7
<211> LENGTH: 220
<212> TYPE: PRT
<213> ORGANISM: Mus musculus

<400> SEQUENCE: 7

Met Glu Leu Gln Arg Thr Ser Ser Ile Ser Gly Pro Leu Ser Pro Ala
  1               5                  10                  15

Tyr Thr Gly Gln Val Pro Tyr Asn Tyr Asn Gln Leu Glu Gly Arg Phe
             20                  25                  30

Lys Gln Leu Gln Asp Glu Arg Glu Ala Val Gln Lys Lys Thr Phe Thr
         35                  40                  45

Lys Trp Val Asn Ser His Leu Ala Arg Val Ser Cys Arg Ile Thr Asp
     50                  55                  60

Leu Tyr Thr Asp Leu Arg Asp Gly Arg Met Leu Ile Lys Leu Leu Glu
 65                  70                  75                  80

Val Leu Ser Gly Glu Arg Leu Pro Lys Pro Thr Lys Gly Arg Met Arg
                 85                  90                  95

Ile His Cys Leu Glu Asn Val Asp Lys Ala Leu Gln Phe Leu Lys Glu
            100                 105                 110

Gln Arg Val His Leu Glu Asn Met Gly Ser His Asp Ile Val Asp Gly
        115                 120                 125

Asn His Arg Leu Thr Thr Leu Glu Leu Leu Glu Val Arg Arg Gln Gln
    130                 135                 140

Glu Glu Glu Glu Arg Lys Arg Arg Pro Pro Ser Pro Asp Pro Asn Thr
145                 150                 155                 160

Lys Val Ser Glu Glu Ala Glu Ser Gln Gln Trp Asp Thr Ser Lys Gly
                165                 170                 175

Asp Gln Val Ser Gln Asn Gly Leu Pro Ala Glu Gln Gly Ser Pro Arg
            180                 185                 190

Val Ser Tyr Arg Ser Gln Thr Tyr Gln Asn Tyr Lys Asn Phe Asn Ser
        195                 200                 205

Arg Arg Thr Ala Ser Asp His Ser Trp Ser Gly Met
    210                 215                 220

<210> SEQ ID NO 8
<211> LENGTH: 1964
<212> TYPE: DNA
<213> ORGANISM: Mus musculus
<220> FEATURE:
<221> NAME/KEY: CDS
<222> LOCATION: (322)..(1509)

<400> SEQUENCE: 8
ttggaacagt tacttcagtg gaggcagcag aaatgaggct agtccagact cacaggaata    60
gggttccatt ctcaagaaga tgatttaaag taattatcct ttacgcatag ttatcatcac   120
```

-continued

```
cacaaaaaaa gattccaacc ttttccacag aactattatg atttatttt atatgaatgt      180 atgtatttat tattatatga actcctataa tgatcacctt tacatattca cattttctta    240
ataattagtt tagccgcgtc cggaggtccg acagctctgc agctccgagc gcgcgactag    300
ccagaaagtt tcaggccatc c atg agc cac cag gaa agg att gcc agc cag      351
                         Met Ser His Gln Glu Arg Ile Ala Ser Gln
                          1               5                  10 agg agg aca aca gcc gaa gtc cca atg cac aga tca act gcc aat caa      399
Arg Arg Thr Thr Ala Glu Val Pro Met His Arg Ser Thr Ala Asn Gln
                 15                  20                  25 agc aag agg agc cgg tca cca ttt gcc agc aca cgt cgt cgc tgg gat      447
Ser Lys Arg Ser Arg Ser Pro Phe Ala Ser Thr Arg Arg Arg Trp Asp
             30                  35                  40 gac agc gag agc tcg gga gcc agc ctg gct gtt gag agt gag gat tat      495
Asp Ser Glu Ser Ser Gly Ala Ser Leu Ala Val Glu Ser Glu Asp Tyr
         45                  50                  55 tcc agg tgg cgg gat gct gcc gat gct gag gag gct cat gcc gag ggc      543
Ser Arg Trp Arg Asp Ala Ala Asp Ala Glu Glu Ala His Ala Glu Gly
     60                  65                  70 cta gcc aga aga ggc cga ggt gag gct gcc agc agc tca gag cca agg      591
Leu Ala Arg Arg Gly Arg Gly Glu Ala Ala Ser Ser Ser Glu Pro Arg
 75                  80                  85                  90 tat gct gaa gac cag gat gcc agg agt gaa caa gcg aag gca gac aaa      639
Tyr Ala Glu Asp Gln Asp Ala Arg Ser Glu Gln Ala Lys Ala Asp Lys
                 95                 100                 105 gtg cca aga cgg cgg cga acc atg gca gac cct gac ttc tgg gca tac      687
Val Pro Arg Arg Arg Arg Thr Met Ala Asp Pro Asp Phe Trp Ala Tyr
             110                 115                 120 acc gac gat tac tac cga tac tac gag gaa gat tct gac agc gac aaa      735
Thr Asp Asp Tyr Tyr Arg Tyr Tyr Glu Glu Asp Ser Asp Ser Asp Lys
         125                 130                 135 gag tgg atg gct gcc ctg cgc agg aag tac cga agc cga gag caa ccc      783
Glu Trp Met Ala Ala Leu Arg Arg Lys Tyr Arg Ser Arg Glu Gln Pro
     140                 145                 150 cag tcc tcc agc gga gaa agc tgg gag ctt ctg cca gga aag gaa gaa      831
Gln Ser Ser Ser Gly Glu Ser Trp Glu Leu Leu Pro Gly Lys Glu Glu
155                 160                 165                 170 ctg gaa cgt cag caa gcc gga gct ggc agc ctc gcc agt gct ggc agc      879
Leu Glu Arg Gln Gln Ala Gly Ala Gly Ser Leu Ala Ser Ala Gly Ser
                 175                 180                 185 aat ggc agt ggt tat cct gaa gaa gta caa gac cca tct ctt cag gag      927
Asn Gly Ser Gly Tyr Pro Glu Glu Val Gln Asp Pro Ser Leu Gln Glu
             190                 195                 200 gaa gaa cag gcc tct ctg gaa gaa gga gaa atc cct tgg ctt cgc tac      975
Glu Glu Gln Ala Ser Leu Glu Glu Gly Glu Ile Pro Trp Leu Arg Tyr
         205                 210                 215 aat gag aat gaa agc agc agc gag ggt gat aat gag tct acc cat gag     1023
Asn Glu Asn Glu Ser Ser Ser Glu Gly Asp Asn Glu Ser Thr His Glu
     220                 225                 230 ctc ata cag cct ggg atg ttc atg ctg gat gga aac aac aac ctg gaa     1071
Leu Ile Gln Pro Gly Met Phe Met Leu Asp Gly Asn Asn Asn Leu Glu
235                 240                 245                 250 gat gac tcc agc gtg agc gaa gac ctc gaa gtg gac tgg agc ctg ttt     1119
Asp Asp Ser Ser Val Ser Glu Asp Leu Glu Val Asp Trp Ser Leu Phe
                 255                 260                 265 gat ggg ttt gcc gat ggc ttg gga gtg gcc gaa gcc atc tcc tac gtg     1167
Asp Gly Phe Ala Asp Gly Leu Gly Val Ala Glu Ala Ile Ser Tyr Val
             270                 275                 280 gat cct cag ttc ctc acc tac atg gct ctg gaa gag cgt ctg gcc cag     1215
Asp Pro Gln Phe Leu Thr Tyr Met Ala Leu Glu Glu Arg Leu Ala Gln
```

|     |     |     |     |     |     |     |     |     |     |     |     |     |     |     |     | |
|---|---|---|---|---|---|---|---|---|---|---|---|---|---|---|---|---|
|     |     |     | 285 |     |     |     | 290 |     |     |     | 295 |     |     |     |     | |
| gca | atg | gag | acg | gcc | ctg | gca | cac | ttg | gag | tct | ctc | gcc | gtt | gat | gtc | 1263 |
| Ala | Met | Glu | Thr | Ala | Leu | Ala | His | Leu | Glu | Ser | Leu | Ala | Val | Asp | Val |     |
|     | 300 |     |     |     | 305 |     |     |     | 310 |     |     |     |     |     |     |     |
| gaa | gtg | gcc | aac | cca | cca | gca | agc | aag | gag | agc | att | gat | gcc | ctt | cct | 1311 |
| Glu | Val | Ala | Asn | Pro | Pro | Ala | Ser | Lys | Glu | Ser | Ile | Asp | Ala | Leu | Pro |     |
| 315 |     |     |     | 320 |     |     |     | 325 |     |     |     |     | 330 |     |     |     |
| gag | atc | ctg | gtc | acc | gaa | gat | cat | ggt | gca | gtg | ggc | cag | gaa | atg | tgc | 1359 |
| Glu | Ile | Leu | Val | Thr | Glu | Asp | His | Gly | Ala | Val | Gly | Gln | Glu | Met | Cys |     |
|     |     |     | 335 |     |     |     | 340 |     |     |     | 345 |     |     |     |     |     |
| tgt | cct | atc | tgc | tgc | agc | gaa | tat | gtg | aag | ggg | gag | gtg | gca | act | gag | 1407 |
| Cys | Pro | Ile | Cys | Cys | Ser | Glu | Tyr | Val | Lys | Gly | Glu | Val | Ala | Thr | Glu |     |
|     | 350 |     |     |     | 355 |     |     |     | 360 |     |     |     |     |     |     |     |
| cta | cca | tgc | cac | cac | tat | ttc | cac | aag | ccc | tgc | gtg | tcc | atc | tgg | ctt | 1455 |
| Leu | Pro | Cys | His | His | Tyr | Phe | His | Lys | Pro | Cys | Val | Ser | Ile | Trp | Leu |     |
| 365 |     |     |     | 370 |     |     |     | 375 |     |     |     |     |     |     |     |     |
| cag | aag | tct | ggc | acc | tgc | cca | gtg | tgc | cgc | tgc | atg | ttc | cct | ccc | ccg | 1503 |
| Gln | Lys | Ser | Gly | Thr | Cys | Pro | Val | Cys | Arg | Cys | Met | Phe | Pro | Pro | Pro |     |
| 380 |     |     |     | 385 |     |     |     | 390 |     |     |     |     |     |     |     |     |
| ctc | taa | aagccaaggc | tcgtcgtaac | agtcagcctg | gttacattcc | ctgtccgaaa |     |     |     |     |     |     |     |     |     | 1559 |
| Leu |     |     |     |     |     |     |     |     |     |     |     |     |     |     |     |     |
| 395 |     |     |     |     |     |     |     |     |     |     |     |     |     |     |     |     |

```
cccacaatac tacaggagcc cttgttctaa acttacaatg aaaccagtca gtcaattaga    1619
ctaaagttgt tgattccttg tgattatttc catgtgaaaa tggttgtgta caatgacatt    1679
taaaaaaaat catcctctcg tttagaaggt agaaagggg aaaggaaact ttctaaatgc     1739
tgcttgagat tgcagtaaga acatacattt tctaacctga agttgaaac aaatcccact     1799 tgttctgtag actgtgtctc tcttacctgt tgctgtcagg gttacctatc tgctaaacta    1859
tgtcggaaag acaaaattac ttttgttgca tgtcatgggt taatgttcct gtatttgcag    1919
tggtgtaaaa gcttattaaa gttcttcttt tgctttgacc ccgaa                    1964

<210> SEQ ID NO 9
<211> LENGTH: 395
<212> TYPE: PRT
<213> ORGANISM: Mus musculus

<400> SEQUENCE: 9
```

| Met | Ser | His | Gln | Glu | Arg | Ile | Ala | Ser | Gln | Arg | Thr | Thr | Ala | Glu |
|---|---|---|---|---|---|---|---|---|---|---|---|---|---|---|
| 1 |     |     |     | 5 |     |     |     |     | 10 |     |     |     |     | 15 |

| Val | Pro | Met | His | Arg | Ser | Thr | Ala | Asn | Gln | Ser | Lys | Arg | Ser | Arg | Ser |
|---|---|---|---|---|---|---|---|---|---|---|---|---|---|---|---|
|     |     |     | 20 |     |     |     |     | 25 |     |     |     |     | 30 |     |     |

| Pro | Phe | Ala | Ser | Thr | Arg | Arg | Arg | Trp | Asp | Asp | Ser | Glu | Ser | Ser | Gly |
|---|---|---|---|---|---|---|---|---|---|---|---|---|---|---|---|
|     |     | 35 |     |     |     |     | 40 |     |     |     |     | 45 |     |     |     |

| Ala | Ser | Leu | Ala | Val | Glu | Ser | Glu | Asp | Tyr | Ser | Arg | Trp | Arg | Asp | Ala |
|---|---|---|---|---|---|---|---|---|---|---|---|---|---|---|---|
|     | 50 |     |     |     |     | 55 |     |     |     |     | 60 |     |     |     |     |

| Ala | Asp | Ala | Glu | Glu | Ala | His | Ala | Glu | Gly | Leu | Ala | Arg | Arg | Gly | Arg |
|---|---|---|---|---|---|---|---|---|---|---|---|---|---|---|---|
| 65 |     |     |     |     | 70 |     |     |     |     | 75 |     |     |     |     | 80 |

| Gly | Glu | Ala | Ala | Ser | Ser | Glu | Pro | Arg | Tyr | Ala | Glu | Asp | Gln | Asp |
|---|---|---|---|---|---|---|---|---|---|---|---|---|---|---|
|     |     |     |     | 85 |     |     |     |     | 90 |     |     |     |     | 95 |

| Ala | Arg | Ser | Glu | Gln | Ala | Lys | Ala | Asp | Lys | Val | Pro | Arg | Arg | Arg |
|---|---|---|---|---|---|---|---|---|---|---|---|---|---|---|
|     |     |     |     | 100 |     |     |     |     | 105 |     |     |     |     | 110 |

| Thr | Met | Ala | Asp | Pro | Asp | Phe | Trp | Ala | Tyr | Thr | Asp | Tyr | Tyr | Arg |
|---|---|---|---|---|---|---|---|---|---|---|---|---|---|---|
|     |     |     | 115 |     |     |     |     | 120 |     |     |     |     | 125 |     |

| Tyr | Tyr | Glu | Glu | Asp | Ser | Asp | Ser | Asp | Lys | Glu | Trp | Met | Ala | Ala | Leu |
|---|---|---|---|---|---|---|---|---|---|---|---|---|---|---|---|
|     |     |     | 130 |     |     |     |     | 135 |     |     |     |     | 140 |     |     |

Arg Arg Lys Tyr Arg Ser Arg Glu Gln Pro Gln Ser Ser Ser Gly Glu

```
                145                 150                 155                 160
Ser Trp Glu Leu Leu Pro Gly Lys Glu Glu Leu Glu Arg Gln Gln Ala
                    165                 170                 175

Gly Ala Gly Ser Leu Ala Ser Ala Gly Ser Asn Gly Ser Gly Tyr Pro
                180                 185                 190

Glu Glu Val Gln Asp Pro Ser Leu Gln Glu Glu Gln Ala Ser Leu
            195                 200                 205

Glu Glu Gly Glu Ile Pro Trp Leu Arg Tyr Asn Glu Asn Glu Ser Ser
            210                 215                 220

Ser Glu Gly Asp Asn Glu Ser Thr His Glu Leu Ile Gln Pro Gly Met
225                 230                 235                 240

Phe Met Leu Asp Gly Asn Asn Asn Leu Glu Asp Asp Ser Ser Val Ser
                245                 250                 255

Glu Asp Leu Glu Val Asp Trp Ser Leu Phe Asp Gly Phe Ala Asp Gly
            260                 265                 270

Leu Gly Val Ala Glu Ala Ile Ser Tyr Val Asp Pro Gln Phe Leu Thr
            275                 280                 285

Tyr Met Ala Leu Glu Glu Arg Leu Ala Gln Ala Met Glu Thr Ala Leu
            290                 295                 300

Ala His Leu Glu Ser Leu Ala Val Asp Val Glu Val Ala Asn Pro Pro
305                 310                 315                 320

Ala Ser Lys Glu Ser Ile Asp Ala Leu Pro Glu Ile Leu Val Thr Glu
                325                 330                 335

Asp His Gly Ala Val Gly Gln Glu Met Cys Cys Pro Ile Cys Cys Ser
            340                 345                 350

Glu Tyr Val Lys Gly Glu Val Ala Thr Glu Leu Pro Cys His His Tyr
            355                 360                 365

Phe His Lys Pro Cys Val Ser Ile Trp Leu Gln Lys Ser Gly Thr Cys
        370                 375                 380

Pro Val Cys Arg Cys Met Phe Pro Pro Leu
385                 390                 395

<210> SEQ ID NO 10
<211> LENGTH: 2992
<212> TYPE: DNA
<213> ORGANISM: Mus musculus

<400> SEQUENCE: 10
gggcaactga aggcagatga agagccctgc ccctgcccac atgtggaacc ttgtgctgtt      60
cttgccttca ctgttggctg tgcttccgac cactactgcc gagaagaatg gcatcgatat     120
ctacagcctc acgtggact cccgggtctc ttcccgattt gcccatactg ttgtcaccag     180
ccgggtggtc aacagagccg atgctgttca agaagcgacc ttccaagtag agctacccag     240
gaaagccttc atcaccaact tctccatgat catcgatggc gtgacctacc aggggttgt      300 caaagagaag gccgaagccc agaaacaata cagtgccgcc gtgggcaggg agagagtgc      360 tggcatcgtc aagaccactg ggaggcagac agagaagttt gaagtgtcag tcaacgtggc     420
ccctggttcc aagattacct cgaactcat ataccaggaa ctgctccaaa ggcgactggg      480
aatgtatgag ctactcctca agtgaggcc tcagcagctg gtgaagcacc ttcagatgga      540
catctacatc tttgagcctc agggtattag catcctggag acagagagca ccctcatgac     600
cccggagctg gcaaatgccc ttaccacttc acagaacaag accaaggctc atatccggtt     660
caagccgacg ctctcccagc aacagaagtc tcagagtgag caggacacgg tgctgaatgg     720
ggacttcatc gtccgctatg atgtcaaccg gtctgactct gggggctcca ttcagattga     780
```

```
ggaaggctac tttgtgcacc actttgctcc agagaacctt cctacaatgt ccaagaatgt    840
gatctttgtc attgataaaa gcggatctat gtcaggcaag aaaatccagc agacccgaga    900
agccctagtc aagatcttga aagacctcag cccccaagac cagttcaacc tcattgagtt    960
cagtggggaa gcaaaccaat ggaagcagtc actggtgcaa gcgacagaag agaatttgaa   1020
caaggctgta aactatgctt ccaggatccg ggctcacgga gggaccaaca tcaataatgc   1080
agtgctgttg gctgtggagc tgctggacag aagcaaccaa gctgagctac tgccctcgaa   1140
gagcgtctcc cttatcatcc tgctcacgga cggtgacccc actgtgggag aaaccaaccc   1200
cacgattatc cagaacaacg tgcgggaagc catcaatggg cagtatagcc tcttctgcct   1260 gggggttcggc tttgatgtga actatccttt cctggagaag atggcactgg acaatggtgg   1320
cctggccagg cgcatctatg aggattcaga ctctgcactg cagcttcagg atttctacca   1380
cgaagtagcc aatccactgc tctcatcagt ggccttcgaa taccccagtg atgctgtgga   1440
ggaagtcact cggtacaagt tccaacacca ctttaagggc tcagagatgg tggtggctgg   1500
gaagctccag gaccagggtc ctgatgtcct cttagccaaa gtcagtgggc agatgcacat   1560
gcagaacatc actttccaaa cggaggccag cgtagcccaa caagagaagg agtttaagag   1620
ccccaagtac atctttcaca actttatgga gagactgtgg gcactgctga ctatacagca   1680
acagctggag cagaggattt cagcgtcagg tgccgaatta gaggccctcg aggcccaagt   1740
tctgaacttg tcactcaagt acaattttgt caccctctc acgcacatgg tggtcaccaa   1800
acctgaaggt caagaacaat tccaagttgc tgagaagcct gtggaagtcg gtgatggcat   1860
gcagagactc cccttagcag ctcaagccca ccccttcagg cctcctgtca gaggatctaa   1920
actgatgacc gtgctgaaag aagcaggtc ccagataccc agacgcggtg atgccgttag   1980
ggcatctagg caatacattc ctcccggatt cccggacct cctggacctc cggatttcc   2040 tgcaccccct ggacctcctg gatttcctgc accccctgga cctcctcttg cttctggctc   2100
tgacttcagc cttcagcctt cctatgaaag gatgctaagc ctgccctccg ttgcagcaca   2160
atatcctgct gacccacatc tggttgtgac ggaaaaaagt aaagaaagca ccataccaga   2220
ggaatcccca aacccagacc accccaggt tcctactatt accttgccgc ttccgggatc   2280
cagtgtggac cagctctgtg tggatatctt acattctgag aagcccatga agctgttcgt   2340
agaccccagt cagggtctgg aggtgactgg taagtatgag aatactgggt tctcgtggct   2400
cgaagtgacc atccagaagc ctcacctgca ggtccatgca acccctgaac gactggtggt   2460
gacacgaggc agaaaaaaca ctgaatacaa gtggaagaag acgctgttct ctgtgttacc   2520
tggcttgaag atgaccatga atatgatggg actcctacag ctcagtggcc cagacaaagt   2580
caccatcggc ctcctgtccc tggatgaccc tcagagagga ctaatgctgc ttttgaatga   2640
cacccagcac ttctccaaca cgttaaaagg ggagcttggt cagttttacc gggacatcgt   2700
ctgggagcca cccgtcgagc cagataatac aaaacggaca gtcaaagttc aaggagttga   2760
ctacctggct accagagagc tcaagttgag ttaccaagaa gggttcccag agcagagat   2820 ttcctgctgg acagtggaga tatagaactg ttaggagcgc cgctccctgc catgttgtcc   2880
tcgtacgcag gcagatgaca cccttatgcca acagggacgc ctgtgaggcc gagaccttga   2940
tgggaagagg atgctcccctt gttacaaata agaagggca gtgtgaaccc ga            2992
```

<210> SEQ ID NO 11
<211> LENGTH: 1177
<212> TYPE: DNA
<213> ORGANISM: Mus musculus
<220> FEATURE:
<223> OTHER INFORMATION: For all n's in this sequence, n=(a or g or c or t)

<400> SEQUENCE: 11

| | | | | | |
|---|---|---|---|---|---|
| ggtggccaag | agcagttcac | ctgctctggg | gcaagccttg | cttgtgtttt | agtgagtcag | 60 |
| ggcctcccca | ggcagtaaga | tgttgagtgt | ggaggcccag | gccgctgacc | tgcagccctg | 120 |
| tcccccacag | gcaggctgca | tgctcttccc | ccacatttct | ccttgcgagg | tgcgcgtgct | 180 |
| catgctcctg | tactcgtcta | agaagaagat | cttcatgggc | ctcatcccct | acgaccagag | 240 |
| cggnttcgtc | aacgccatac | gacaggtcat | caccacccgc | aaacaggtgt | gccagctgag | 300 |
| ggtagnctgc | tcctgctcct | acccttggta | gacccactgn | ctcccactgg | tgtggaatgt | 360 |
| ggcatcaagg | ctgagtcggc | gnctgggag | gagctgtgac | gangcagtgc | catacccaaa | 420 |
| tgggctcgag | ggaaacntag | ctttataggc | ttcagagggg | cagaactaga | gggtggggcc | 480 |
| tgggtgtaga | ggcagggcag | gagtggggtg | gcaggtttgg | caagaggccc | agagtctctg | 540 |
| gagggtcaca | gtgttgatga | catctttctn | agaancctgc | tactngctta | gncagctgtg | 600 |
| gtcctctctn | ccacctgggg | gataccttggc | nacaggcngt | gggcnncggg | ggtgaanact | 660 |
| ctggacctgt | tnagantgtc | aacaacaaat | tcttgacatg | gagtggtgtc | atggagtggn | 720 |
| aggaggtgan | ctgccgggga | ctgtgtggac | tgttgnccct | aagctgccct | ccctgaagt | 780 |
| gccttctcgc | tctgccccaa | aacccagacc | tgagcccaac | agccggtcca | agaggtggct | 840 |
| gccatcccac | gtctatgtga | accaagggga | gatcctgtga | ttccgggtac | cccgggtgg | 900 |
| ccccattgac | agtgccgccc | cctgggggga | ggacttctga | ctgataccttc | ctgtcttgtg | 960 |
| tggcaggaga | acagaccagt | ggcctcggag | gctcttcatg | cagctcattc | cccagcagtt | 1020 |
| gctggtgagg | ggtcagggga | ttccaggctg | ggggtgggcc | aaagaccctg | tggtgggctg | 1080 |
| gttcagaggc | ctgcctggct | tccccagcaa | gctagggttc | cataaagaag | ccctcggcct | 1140 |
| tcccccagac | caccctcgtg | ccactgttcc | ggaattc | | | 1177 |

<210> SEQ ID NO 12
<211> LENGTH: 2998
<212> TYPE: DNA
<213> ORGANISM: Mus musculus
<220> FEATURE:
<223> OTHER INFORMATION: For all n's in this sequence, n=(a or g or c or t)

<400> SEQUENCE: 12

| | | | | | |
|---|---|---|---|---|---|
| ggcacgagct | taactgtgct | aacttctgtg | atgatcatgt | gtgatgagta | tgtgctctca | 60 |
| tttgatttgt | gggaaaaaac | aaaacaaaaa | aatccgaagg | acacaaagag | gactaatctt | 120 |
| aaaccagata | tctagtagtc | accaaagcca | cactttgaat | tcgaaaagct | tagcactgta | 180 |
| gcttagctca | tgctatcttt | taagagaga | atttaattat | ttaatatatg | gaaggacatt | 240 |
| aggctagtgt | gtctggcaca | tggtataaac | tcaataaatg | gtggacgtta | tcagtgctac | 300 |
| tataatgagt | ttaataattt | ggtttcatct | cctttaatca | gaccagtgtt | cactactagc | 360 |
| tgggtctctg | gaataggcac | agatatattc | atctggagtg | tcacacatac | tctgtgcgcg | 420 |
| aaagagttca | gaatagccct | tcaataagcc | aattactctt | gctgtcatcc | ttatttctta | 480 |
| actttccctt | agcgttgctt | ttatgtatca | aacttttctt | ccttatttta | cgtaatactt | 540 |
| ttaatgacaa | ctttctagaa | ataagaacta | taccctaaaa | gattgaaata | ttcttagttt | 600 |
| tcttatcta | catcagaaat | tgtttagctg | atacaacata | cttatattgt | ttaaggaatt | 660 |
| ctgtttaata | ccttggtatt | tataattttc | ataagtttat | ttgtattaat | aggaactctt | 720 |

-continued

```
acaaagaatg tatagaaaat aagccccatc atttgtcagt gtgacaattt tcccagtgtt      780
taaattgttt aagctgtttg taccctata taagctctgt tccttctttg gccctttccc      840
ccttagccta aatctccatt ttgcctgacg atctcttccc tgacaaaatg cctgcttctg      900
cgcactgagt cacagtctac taaaatgcat tccattgtgc ccatgtccct cttaatgtga      960 tgacccaga catgaccagg gcagagcaca gagggagcat cactttcttt gaccagagca     1020
tctatttcca gcaatgcagc ctaaggtcac attagcattt ttggcagcaa aatacaccct     1080
tggctcatgc tgttatgctg tcaaccaaat cctccatgac tttttcacat gaactcccat     1140
taaataaggc ttcccacatc cggtacgaat atagacagta atgtgcagtc tggtgaagtt     1200
atttacataa gttcctatta aacatcagct aatctatatt tattatttta gaatattgag     1260
acagatttct attcccagct atatagatat ggttttagaa tactttatta ttattttttt     1320
aatgtgtctt ctctgaaccc gataagaaca tagtcccaga caatctttaa gttcagagtc     1380
ttacagtttg tatagagacc tagaggctag ctatatttct ttagacatca acacatcatc     1440
agataggatc cacccaaggg ccttacaaat cctgtatact gaaatgcctt ttcctgacga     1500
tattctggag actgttaagt gaatgcgcag atctgaaccg agccgagcct gtagtgggga     1560
agagctaaag catggcagtt gtcttcatca atgatggagt cttcattat gttgtctcaa     1620 aagacacatg cttcagccct gggtctcaaa actctcatgc ttcggccctg ggtctcacac     1680
tcctggcttc ccgagtggtc atagctaaga ccttctcaca ctaaatccca ggatgagctc     1740
atgttgatgt tcctgcttgc ttctctgaaa ttggcagttc tcgtgggaaa aaaaatctac     1800
ttatacttgt gtgcttcata aagcaactcg gtagcagggc ttaggggtgc ttcgagtgtg     1860
gcagtgatag agaagaccga taaagcgaaa tctatgatat ctcatacatc attttaatta     1920
tttaaattac ttttgttagt acacaaaagt attttgttag tacaccctgt ttatctatgt     1980
gtatactcta cctttcgcat acactgactt catttctttt tctcctcacc catcctgatg     2040
agctgctctc ctcccagaca agctctggca gttttaaagt cacgtgtgta tcttttaact     2100
ctagcttctg cctattagac aaaacaagat acttgtcttt ctccccatct ccctcctttt     2160
gtttaattct cctccagccc tacatggatc ccccttgacc tcgtgtcata tatctaaatc     2220
tgtataaata aagagatgat ttaatctacg ttctatgtac aaaagagaat ataaatgctc     2280
gtctttctga atctgtctta tttggtttca cacaatatct gctctctttt accgcaaatg     2340
gtatcatctc gttcccttta cacgttgaag aaaatttcat tttgtgtgtg tgtgtgtgtg     2400
tgtgtgtgtg aactatatat ttttacgcta tctggtgagg aacatcaagg ccaagatatg     2460
gatcttggct attgtaaaga gtgtagtaag aaacacaacc gtataatcat ctctgttgca     2520
tgctggcatg ctggctacaa tcctcacctg tgtacccaga gtgagagctg gaccacatgg     2580
taatgcaacc tgtagttatt atttaatgtg tacttcttgt ttaatgttta aagatactac     2640
ttattttaat gttatgtgta tggatgtttt atctatgtgt ttgtctgtat atagtgggca     2700
cgtactggtc tcagagccag aggaaggcat cagagtccct gggggttggaa ttaaagatgt     2760 ttgtgagtac ctgcgtgtat cctggacttc aaacccgggt cttcttcaag agcagccagt     2820
gctcttaacc actgaggatc tctccagcct catcgctgat ttaggaagga cttttactga     2880
tttggagtag ctgtaggcaa tgcagtctat gacgatttcc ttttagcagt tcttgtttgt     2940
tttcttaatg atagccatac tgattgctga gatttacagc agcactagca agctggaa      2998
```

<210> SEQ ID NO 13
<211> LENGTH: 1121

<212> TYPE: DNA
<213> ORGANISM: Mus musculus
<220> FEATURE:
<223> OTHER INFORMATION: For all n's in this sequence, n=(a or g or c or t)

<400> SEQUENCE: 13

```
ctcgagtttt ttttttttttt ttttggagaa gggnaacatt tattcattca acaaatnttg      60
atgacctgat ggggnagata actgagctag tcagcgcgta ggtagcaaac ataaggntat     120
agtaccccag ntaatggtct ncccacatgt cactgaagga gtgtcagttc tcagcatttt     180
acctttaatt ttaattttta cctctaaatg cgctttagga ggctacccac agttgatgac     240
aaacagtgta gccaggcatg ccagaactgt taccagcaga acttttggcc gactgtagct     300
ggcagtgttc tcagtagtgc agttcatgcc tggtgggtgt aactagggta caacgaagtc     360
actttgaact cttttgctaa ctaaataagc caaataaaca aatcatgaaa tactgattag     420
caatgcaata tttcatggca tgggaagagc ttcgacttct ccatcggtga caaggagcag     480
cttctggaag gaaggtctgg agaaaacaac tgacggggag ctccgaggag ccctgaacac     540
gtcactcaac agcactggcg ttgacacagc tgctgtggtc cagcagtcac tcagtggaga     600
gtgccaaagg gtgggcagac agncagncct acttcttcat ctccaggatg gcacttccag     660
gcccacggtt cttagcacta cagatgttgc agtattgtgc aggagcattc atgctcggca     720
taggcaggca ctccttgtgg aacatgtgcc ggcagtggaa gaccaccacg ctgaagggct     780
tcnctgcatc tgttgggagg atgggagaaa ggcatgattc acagatattc tcttcatcaa     840
ccagaacgcc tttcatttgg gttcggngca ttttttcaca caccaacgac aatgagtcag     900
ctacgaggat tttcttgcag ccttcccgaa gcagaatctt caagttataa tcttgcagaa     960
ttttaaccaa ggaatctctc aaattgggaa tctccattcc ttccttaatt cggtggataa    1020
gtagaatcgg gtccacatgt gtgccaatgt tgttcaacaa gccagtgata aatggtggtt    1080
tgtcgatgga gtatagaatc agatcttctc gtgccgaatt c                        1121
```

<210> SEQ ID NO 14
<211> LENGTH: 779
<212> TYPE: DNA
<213> ORGANISM: Mus musculus

<400> SEQUENCE: 14

```
ctcgagagat gccccacagt ccctcaggac ccgagtcagg taatctgcct ttggccttag      60
tgacctcctt ttctgggcga gtataccatc cactttcctc cctgacaggc agttcagtaa     120
cccaacccctt tcattcctcc ttcagttgtc aaagacaact taacatccaa gactaacaag     180
caagatgact caggagcatg gnctctgggt tcccctggca ccatgcatgg tgatgctagt     240
taaggctgac ttagctctta gcaaccttgg ttgggatagc ttaagctcat ctccactttc     300
ctaccaaaca gaaaagaatt tgagtcctct tgctatgagg ctctcgctcc catctcaggc     360
gagcttcctg cccctcaccc aagcttggga ggtagagtta tggagagggc aaggaagcag     420
gactggaaag atagacttat ggatccacca ctcataaagt cacaaagtcc cctcacacct     480
gctagactta gactctaaat cattacgttg tcaccaacag aggtgactcc tcaaccacaa     540
gagcctgtag tgagcttcaa gagagaagag gacaagncag acctggactg catgaccttg     600
cacctgtgat gaagtcacag caataggtga tgctcaaaaa gccccaataa aatgcaagac     660
agncaaacag aagccctgtc tgtccccatt ggtgggtaat gtagctgatg tggctggttc     720
tccttccttg acttcacccct gactatggga attgtccttc agtgcctcgt gccgaattc     779
```

-continued

<210> SEQ ID NO 15
<211> LENGTH: 981
<212> TYPE: DNA
<213> ORGANISM: Mus musculus
<220> FEATURE:
<223> OTHER INFORMATION: For all n's in this sequence, n=(a or g or c or t)

<400> SEQUENCE: 15

| | | | | | | |
|---|---|---|---|---|---|---|
| ctcgagaggt | gaaggcagaa | gtatcacaag | ttcaagttca | aggncagcct | gggcttcaca | 60 |
| agacccaaaa | aaataaatat | gaggncagtc | caggctggga | ctcaggtcac | tgctgtgctg | 120 |
| agccatcgtc | agagaagttt | cttctttnnt | tttgatagga | gctaacacag | cgacccacan | 180 |
| ctggacagnc | tgcagtgagt | gagtgagtaa | gtgacctaaa | agtgatgtct | tcattaatct | 240 |
| cccctcccca | ggcntcaggg | agctctgagg | aagaggaggc | agaaagatgg | tgagagccag | 300 |
| cagggatgga | ggacaccaag | gaagcagtgt | cttccgacac | aacaggactg | gcatttagga | 360 |
| agtcacagag | gctgtggctg | cccagggcct | gcacggtcca | agctggctga | gattccagtg | 420 |
| ctgagagaga | caattcaaca | cggnctccca | cccctagnca | agaagttatc | tccaactgat | 480 |
| atccacttgc | aaaggaaaaa | attaggggn | tagagagatg | gctcagtggn | taagagcact | 540 |
| gacttanaaa | atagaaatng | canattngnt | nngangttng | cnaaatngct | gagaaatggc | 600 |
| caattggctg | gaaaacttgc | aacattgcct | ggagaactgc | caaattgcct | ggagagctgc | 660 |
| caaattggcc | tggagagctg | cctacatggc | ctggagagct | gcccacatgg | cctggagaac | 720 |
| tggctacatg | tcctggagag | ctgccaacat | gtcctggaga | tctgcctaca | tggcctggag | 780 |
| aactgcctac | atgacctgga | gagctggcca | catggcctgg | agagctggct | acatgacctg | 840 |
| gagagctgnc | tacatggcct | ggagagctgg | ctacatggcc | tggagagctg | gctacatggc | 900 |
| ctggagagct | ggctacatgg | cctggagagc | tggctacatg | gcctggagag | cctcccagca | 960 |
| aggcctctct | aagccgaatt | c | | | | 981 |

<210> SEQ ID NO 16
<211> LENGTH: 685
<212> TYPE: DNA
<213> ORGANISM: Mus musculus
<220> FEATURE:
<223> OTHER INFORMATION: For all n's in this sequence, n=(a or g or c or t)

<400> SEQUENCE: 16

| | | | | | | |
|---|---|---|---|---|---|---|
| ctcgagatgc | attaaagctt | tgntgcagaa | ggatccgagt | gtgtcctgtg | tgtgtgtcct | 60 |
| cactggcgag | acccttatc | acacagggac | acccccttagg | ttggagtttt | ccttgtaatg | 120 |
| tccactatac | gtctgcttta | tacaataata | ttgnttaaat | ttgnctctat | catgaaatac | 180 |
| ctcactttcc | ttatctgtat | tgattgaaag | ttttggtgga | tgtaatagtt | tgggcttgga | 240 |
| tctgaagtct | tttagagttt | attggacatg | tgcctngatt | cattggnttn | aaaatcntcc | 300 |
| acnacttggg | ggtgtaaagg | ttacccacnc | nattantgga | ggttcttctg | agttccagag | 360 |
| anaangantg | agccaccngg | aattctccct | aaacacactt | tgatcatttc | ctgcctaacc | 420 |
| ctgcagagga | aatattaata | ccctgtagta | ccaaaggaaa | caaataagaa | ggaagactgn | 480 |
| tctctcatgt | ctggaggaag | tttggtgaag | gagtcttctg | tttgctcaca | taggagagat | 540 |
| ctaatacagc | cactatccat | aattaaaaat | ctctgtgaga | gaggcatgac | gaggttctcc | 600 |
| cagtctgtca | agggatgtga | atatgtgttn | ccctgtcatc | ctgtcatgaa | gcctctcttt | 660 |
| ctctctctct | cctcgtgccg | aattc | | | | 685 |

<210> SEQ ID NO 17
<211> LENGTH: 471
<212> TYPE: DNA
<213> ORGANISM: Mus musculus
<220> FEATURE:
<223> OTHER INFORMATION: For all n's in this sequence, n=(a or g or
      c or t)

<400> SEQUENCE: 17
gaattcngcn ttggggtaca tggaccngga gagcttggnt acatggcctg gagagctggn    60
tacatggccc ggngagctgg tttnataaac ctggggangt tgggttnaat ggccccgggg   120
angtnggttn aatanaccng gggaggtgtc tgaaaanagt ggncacgtac tgttctcaga   180
cccagnggaa gncatcagag tcccctgggg ttggaattaa agatgtttgt gagtcnctgc   240
gtgtatcctg gacttcaaac ccgggtcttc ttcaagagca gccagtgctc ttaaccactg   300
agggatctct ccagcctcat cgctgattta ggaaggactt ttactgattt ggagtanctg   360
tagccaatnc agtctatgac gatttccttt tagcagttct tgtttgtttt cttaatgata   420
gccatactga ttgctgagat ttacagcagc actagcaagc tggaactcga g            471

<210> SEQ ID NO 18
<211> LENGTH: 467
<212> TYPE: DNA
<213> ORGANISM: Mus musculus
<220> FEATURE:
<223> OTHER INFORMATION: For all n's in this sequence, n=(a or g or
      c or t)

<400> SEQUENCE: 18
ctcgagnttt ttttttttt ttttttttt ttttttttt ttttttttt ttttttttt        60 tttttnnnnn aanaaanttt taaagttttt ttttttttat naaaannttt ccaaggggg   120 ganggttag aaganagcca nagcctggnc ccccctgcca gaaaaaacca gaggggggtt    180
gatgtcccca agtccagttg tcaccctgaa gaagttcccc acgatttccc tggtggcccc   240
ccgggagtac gtccagagtg tcacccttc catttgggag ctgtgggaag ggntgggnt    300 ccctcccagn ggggccccaa accttctcc tgaacagntc ctgatttctg accatctttc    360
caattccacg gattcaaaga gcatgaccct aggtaagcaa gccaggtcaa gagcattgct   420
tgtctgnagg aaaaggaagg gtccctcctg gcctcgtgcc gaattcc                 467